US006541503B2

(12) United States Patent
Davis et al.

(10) Patent No.: US 6,541,503 B2
(45) Date of Patent: Apr. 1, 2003

(54) SUBSTITUTED OXINDOLE DERIVATIVES AS PROTEIN TYROSINE KINASE AND AS PROTEIN SERINE/THREONINE KINASE INHIBITORS

(75) Inventors: Stephen Thomas Davis, Durham, NC (US); Scott Howard Dickerson, Chapel Hill, NC (US); Stephen Vernon Frye, Durham, NC (US); Philip Anthony Harris, Raleigh, NC (US); Robert Neil Hunter, III, Raleigh, NC (US); Lee Frederick Kuyper, Durham, NC (US); Karen Elizabeth Lackey, Hillsborough, NC (US); Michael Joseph Luzzio, Groton, CT (US); James Marvin Veal, Apex, NC (US); Duncan Herrick Walker, Summit, NJ (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/924,431

(22) Filed: Aug. 8, 2001

(65) Prior Publication Data

US 2003/0004351 A1 Jan. 2, 2003

Related U.S. Application Data

(62) Division of application No. 09/486,960, filed as application No. PCT/EP98/05559 on Sep. 3, 1998.

(30) Foreign Application Priority Data

Sep. 5, 1997 (GB) ............................... 9718913

(51) Int. Cl.$^7$ ....................... A61K 31/429; A61P 39/00; C07D 513/04; C07D 471/04; C07D 487/04
(52) U.S. Cl. ....................... 514/414; 514/419; 514/426; 548/452; 548/483; 548/484; 546/277.1; 546/278.1; 544/111
(58) Field of Search ................................ 514/412, 415, 514/417, 414, 418, 419, 426; 546/277.1, 278.1; 548/452, 454, 465, 483, 484; 544/111

(56) References Cited

U.S. PATENT DOCUMENTS

| 5,051,417 A | 9/1991 | Nadler et al. |
| 5,057,538 A | 10/1991 | Shiraishi et al. |
| 5,089,516 A | 2/1992 | Shiraishi et al. |
| 5,124,342 A | 6/1992 | Kerdesky et al. |
| 5,202,341 A | 4/1993 | Shiraishi et al. |
| 5,374,652 A | 12/1994 | Buzzetti et al. |
| 5,441,880 A | 8/1995 | Beach et al. |
| 5,443,962 A | 8/1995 | Draetta et al. |
| 5,449,755 A | 9/1995 | Roberts et al. |
| 5,488,057 A | 1/1996 | Buzzetti et al. |
| 5,627,207 A | 5/1997 | Buzzetti et al. |
| 5,672,508 A | 9/1997 | Gyuris et al. |
| 5,756,335 A | 5/1998 | Beach et al. |
| 5,770,423 A | 6/1998 | Beach et al. |

FOREIGN PATENT DOCUMENTS

| EP | 0 436 333 A2 | 12/1990 |
| EP | 0 503 49 A1 | 2/1992 |
| EP | 0 503 349 B1 | 2/1992 |
| EP | 0 788 890 A1 | 2/1996 |
| WO | 93/01182 | 7/1992 |
| WO | 92/20796 A2 | 11/1992 |
| WO | 93/10242 | 11/1992 |
| WO | 94/28914 | 6/1993 |
| WO | 93/24514 | 12/1993 |
| WO | 94/23029 | 3/1994 |
| WO | 95/01349 | 5/1994 |
| WO | 96/00226 | 6/1994 |
| WO | 96/16964 | 10/1995 |
| WO | 96/22976 | 12/1995 |
| WO | 96/32380 | 3/1996 |
| WO | 96/40116 | 6/1996 |
| WO | 97/25986 | 1/1997 |
| WO | 97/36867 | 2/1997 |
| WO | 98/07695 | 8/1997 |
| WO | 98/07835 | 8/1997 |
| WO | 98/50356 | * 11/1998 |

OTHER PUBLICATIONS

English Abstract, Caplus DN 133:177082, Massoud Mohamed, Synthetic Studies of . . . 2000.*
Rozengurt, Current Opinion in Cell Biology, 1992, 4, pp. 161–165.
Wilks, Progress in Growth Factor Research, 1990, 2, pp. 97–111.
Hanks et al., Science, 1988, 241, pp. 42–52.
Crews and Erikson, Cell, 1993, 74, pp. 215–217.
Ihle et al., Trends in Biochemical Sciences, 1994, 19, pp. 222–227.

(List continued on next page.)

Primary Examiner—Alan L. Rotman
Assistant Examiner—Rita Desai
(74) Attorney, Agent, or Firm—John L. Lemanowicz

(57) ABSTRACT

Compounds of formula (I): wherein X is N, CH, CCF$_3$, or C(C$_{1-12}$ aliphatic); R$^4$ is sulfonic acid, C$_{1-12}$ aliphatic-sulfonyl, sulfonyl-C$_{1-12}$ aliphatic, C$_{1-12}$ aliphatic-sulfonyl-C$_{1-6}$ aliphatic, C$_{1-6}$ aliphatic-amino, R$^7$-sulfonyl, R$^7$ sulfonyl-C$_{1-12}$ aliphatic, R$^7$-aminosulfonyl, R$^7$-aminosulfonyl-C$_{1-12}$ aliphatic, R$^7$-sulfonylamino, R$^7$-sulfonylamino-C$_{1-12}$ aliphatic, aminosulfonylamino, di-C$_{1-12}$ aliphatic amino, di-C$_{1-12}$ aliphatic aminocarbonyl, di-C$_{1-12}$ aliphatic aminosulfonyl, di-C$_{1-12}$ aliphatic amino, di-C$_{1-12}$ aliphatic aminocarbonyl, di-C$_{1-12}$ aliphatic aminosulfonyl-C$_{1-12}$ aliphatic, (R$^8$)$_{1-3}$-Arylamino, (R$^8$)$_{1-3}$-Arylsulfonyl, (R$^8$)$_{1-3}$-Aryl-aminosulfonyl, (R$^8$)$_{1-3}$-Aryl-sulfonylamino, Het-amino, Het-sulfonyl, Het-aminosulfonyl, aminoiminoamino, or aminoiminoaminosulfonyl, R$^5$ is hydrogen; and further wherein R$^4$ and R$^5$ are optionally joined to form a fused ring, pharmaceutical formulations comprising them and their use in therapy, especially in the treatment of diseases mediated by CDK2 activity, such as alopecia induced by cancer chemotherapy or radiotherapy.

17 Claims, No Drawings

OTHER PUBLICATIONS

Pelech and Sanghera, Trends in Biochemical Sciences, 1992, 17, pp. 233–238.
Massague and Roberts, Current Opinion in Cell Biology, 1995, 7, pp. 769–772.
Myerson et al., EMBO Journal, 1992, 11, pp. 2909–2917.
Draetta, Trends in Cell Biology, 1993, 3, pp. 287–289.
Murray and Kirschner, Nature, 1989, 339, pp. 275–280.
Solomon et al., Molecular Biology of the Cell, 1992, 3, pp. 13–27.
Ducommun et al., EMBO Journal, 1991, 10, pp. 3311–3319.
Gautier et al., Nature, 1989, 339, pp. 626–629.
Gould and Nurse, Nature, 1989, 342, pp. 39–45.
Krek and Nigg, EMBO Journal, 1991, 10, pp. 3331–3341.
Solomon et al., Cell, 1990, 63, pp. 1013–1024.
Pines, Trends in Biochemical Sciences, 1993, 18, pp. 195–197.
Sherr, Cell, 1993, 73, pp. 1059–1065.
Matsushime et al., Molecular & Cellular Biology, 1994, 14, pp. 2066–2076.
Ohtsubo and Roberts, Science, 1993, 259, pp. 1908–1912.
Quelle et al., Genes & Development, 1993, 7, pp. 1559–1571.
Resnitzky et al., Molecular & Cellular Biology, 1994, 14, pp. 1669–1679.
Girard et al., Cell, 1991, 67, pp. 1169–1179.
Pagano et al., EMBO Journal, 1992, 11, pp. 961–971.
Rosenblatt et al., Proceedings of the National Academy of Science USA, 1992, 89, pp. 2824–2828.
Walker and Maller, Nature, 1991, 354, pp. 314–317.
Zindy et al., Biochemical & Biophysical Research Communications, 1992, 182, pp. 1144–1154.
Pines, Current Opinion in Cell Biology, 1992, 4, pp. 144–148.
Lees, Current Opinion in Cell Biology, 1995, 7, pp. 773–780.
Hunter and Pines, Cell, 1994, 79, pp. 573–582.
Brickell, Critical Reviews in Oncogensis, 1992, 3, pp. 401–446.
Courtneidge, Seminars in Cancer Biology, 1994, 5, pp. 239–246.
Powis, Pharmacology & Therapeutics, 1994, 62, pp. 57–95.
Buchdunger et al., Proc. Nat. Acad. Sci. USA, vol. 92, 1995, pp. 2258–2262.
Hosoi et al., Journal of Biochemistry (Tokyo), 1995, 117, pp. 741–749.
Aplin et al., Journal of Neurochemistry, 1996, 67, pp. 699–707.
Tanaka et al., Nature, 1996, 383, pp. 528–531.
Borthwick et al., Biochemical & Biophysical Researc Communications, 1995, 210, pp. 738–745.
Badger et al., The Journal of Pharmacology and Experimental Therapeutics, 1996, 279, pp. 1453–1461.
Shawyer et al., Drug Discovery Today, 1997, 2, pp. 50–63.
He et al., Journal of Virology, 1997, 71, pp. 405–411.
Myers et al., Bioorganic & Medicinal Chemistry Letters, 1997, 7, pp. 421–424.
Vousden, FASEB Journal, 1993, 7, pp. 872–879.
Stone et al., Cancer Research, 1996, 56, pp. 440–452.
Perkins et al., Science, 1997, 275, pp. 523–527.
Baeuerle and Henkel, Annual Review of Immunology, 1994, 12, pp. 141–179.
Beg and Baltimore, Science, 1996, 274, pp. 782–784.
Wang et al., Science, 1996, 274, pp. 784–787.
Van Antwerp et al., Science, 1996, 274, pp. 787–789.
Armstrong, Clinical Infectious Diseases, 1993, 16, pp. 1–7.
Osmani et al., EMBO Journal, 1991, 10, pp. 2669–2679.
Kohn et al., Journal of Cellular Biochemistry, 54, 1994, pp. 440–452.
Osmani et al., Cell, vol. 67, Oct. 18, 1991, pp. 283–291.
Mohammed Kamel, et al., "Monoazo Metal Complex Forming Dyes Part v Dyes Derived from Isatin", J Chem. U. A. R. 9, No. 2, 139–144 (1966).
Vishnu J. Ram, et al., "Pesticidal mannich Bases Derived from Isatinimines", J Heterocycle Chem., pp. 1367–1369, vol. 23, Sep.–Oct. 1986.
Xiaoyun Wu, et al., "Chemical Constituents of Isatis Indigotica", Planta Medica, pp. 55–57, 1997.

* cited by examiner

SUBSTITUTED OXINDOLE DERIVATIVES AS PROTEIN TYROSINE KINASE AND AS PROTEIN SERINE/THREONINE KINASE INHIBITORS

This is a Divisional Application of prior U.S. application Ser. No. 09/486,960 filed Jun. 6, 2000 which was filed under 35 U.S.C. §371 as a United States National Phase Application of International Application No. PCT/EP98/05559 filed Sep. 3, 1998, which claims priority from GB 971891.8 filed Sep. 5, 1997.

The present invention provides novel compounds, novel compositions, method of their use and methods of their manufacture, such compounds generally useful pharmacologically as agents in those disease states alleviated by the alteration of mitogen activated signalling pathways in general, and in particular in the inhibition or antagonism of protein kinases, which pathologically involve aberrant cellular proliferation, such disease states including tumor growth, restenosis, atherosclerosis, and thrombosis. In particular, the present invention relates to a series of substituted oxindole compounds, which exhibit protein tyrosine kinase and protein serine/threonine kinase inhibition, and which are useful in protecting a patient undergoing chemotherapy from chemotherapy-induced alopecia.

BACKGROUND OF THE INVENTION

Cell growth, differentiation, metabolism and function are extremely tightly controlled in higher eukaryotes. The ability of a cell to rapidly and appropriately respond to the array of external and internal signals it continually receives is of critical importance in maintaining a balance between these processes (Rozengurt, Current Opinion in Cell Biology 1992, 4, 161–5; Wilks, Progress in Growth Factor Research 1990, 2, 97–111). The loss of control over cellular regulation can often lead to aberrant cell function or death, often resulting in a disease state in the parent organism.

The protein kinases represent a large family of proteins which play a central role in the regulation of a wide variety of cellular processes and maintaining control over cellular function (Hanks, et al., Science 1988, 241, 42–52). A partial list of such kinases includes ab1, ATK, bcr-ab1, Blk, Brk, Btk, c-kit, c-met, c-src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK4, flt-1, Fps, Frk, Fyn, Hck, IGF-1R, INS-R, Jak, KDR, Lck, Lyn, MEK, p38, PDGFR, PIK, PKC, PYK2, ros, $tie_1$, $tie_2$, TRK, Yes, and Zap70.

One of the most commonly studied pathways involving kinase regulation is cellular signalling from receptors at the cell surface to the nucleus (Crews and Erikson, Cell 1993, 74, 215–7). One example of this pathway includes a cascade of kinases in which members of the Growth Factor receptor Tyrosine Kinases (such as EGF-R, PDGF-R, VEGF-R, IGF1-R, the Insulin receptor), deliver signals through phosphorylation to other kinases such as Src Tyrosine kinase, and the Raf, Mek and Erk serine/threonine kinase families (Crews and Erikson, Cell 1993, 74, 215–7; Ihle, et al., Trends in Biochemical Sciences 1994, 19, 222–7). Each of these kinases is represented by several family members (Pelech and Sanghera, Trends in Biochemical Sciences 1992, 17, 233–8) which play related, but functionally distinct roles. The loss of regulation of the growth factor signalling pathway is a frequent occurence in cancer as well as other disease states.

The signals mediated by kinases have also been shown to control growth, death and differentiation in the cell by regulating the processes of the cell cycle (Massague and Roberts, Current Opinion in Cell Biology 1995, 7, 769–72). Progression through the eukaryotic cell cycle is controlled by a family of kinases called cyclin dependent kinases (CDKs) (Myerson, et al., EMBO Journal 1992, 11, 2909–17). The regulation of CDK activation is complex, but requires the association of the CDK with a member of the cyclin family of regulatory subunits (Draetta, Trends in Cell Biology 1993, 3, 287–9; Murray and Kirschner, Nature 1989, 339, 275–80; Solomon, et al., Molecular Biology of the Cell. 1992, 3, 13–27). A further level of regulation occurs through both activating and inactivating phosphorylations of the CDK subunit (Draetta, Trends in Cell Biology 1993, 3, 287–9; Murray and Kirschner, Nature 1989, 339, 275–80; Solomon, et al., Molecular Biology of the Cell. 1992, 3, 13–27; Ducommun, et al., EMBO Journal 1991, 10, 3311–9; Gautier, et al., Nature 1989, 339, 626–9; Gould and Nurse, Nature 1989, 342, 39–45; Krek and Nigg, EMBO Journal 1991, 10, 3331–41; Solomon, et al., Cell 1990, 63, 1013–24). The coordinate activation and inactivation of different cyclin/CDK complexes is necessary for normal progression through the cell cycle (Pines, Trends in Biochemical Sciences 1993, 18, 195–7; Sherr, Cell 1993, 73, 1059–65). Both the critical G1-S and G2-M transitions are controlled by the activation of different cyclin/CDK activities. In G1, both cyclin D/CDK4 and cyclin E/CDK2 are thought to mediate the onset of S-phase (Matsushime, et al., Molecular & Cellular Biology 1994, 14, 2066–76; Ohtsubo and Roberts, Science 1993, 259, 1908–12; Quelle, et al., Genes & Development 1993, 7, 1559–71; Resnitzky, et al., Molecular & Cellular Biology 1994, 14, 1669–79). Progression through S-phase requires the activity of cyclin A/CDK2 (Girard, et al., Cell 1991, 67, 1169–79; Pagano, et al., EMBO Journal 1992, 11, 961–71; Rosenblatt, et al., Proceedings of the National Academy of Science USA 1992, 89, 2824–8; Walker and Maller, Nature 1991, 354, 314–7; Zindy, et al., Biochemical & Biophysical Research Communications 1992, 182, 1144–54) whereas the activation of cydin A/cdc2 (CDK1) and cyclin B/cdc2 are required for the onset of metaphase (Draetta, Trends in Cell Biology 1993, 3, 287–9; Murray and Kirschner, Nature 1989, 339, 275–80; Solomon, et al., Molecular Biology of the Cell. 1992, 3, 13–27; Girard, et al., Cell 1991, 67, 1169–79; Pagano, et al., EMBO Journal 1992, 11, 961–71; Rosenblatt, et al., Proceedings of the National Academy of Science USA 1992, 89, 2824–8; Walker and Maller, Nature 1991, 354, 314–7; Zindy, et al., Biochemical & Biophysical Research Communications 1992, 182, 1144–54). It is not surprising, therefore, that the loss of control of CDK regulation is a frequent event in hyperproliferative diseases and cancer. (Pines, Current Opinion in Cell Biology 1992, 4, 144–8; Lees, Current Opinion in Cell Biology 1995, 7, 773–80; Hunter and Pines, Cell 1994, 79, 573–82). The selective inhibition of CDKs is therefore an object of the present invention.

The compounds of the present invention are additionally useful in the treatment of one or more diseases afflicting mammals which are characterized by cellular proliferation in the areas of blood vessel proliferative disorders, fibrotic disorders, mesangial cell proliferative disorders and metabolic diseases. Blood vessel proliferative disorders include arthritis and restenosis. Fibrotic disorders include hepatic cirrhosis and atherosclerosis. Mesangial cell proliferative disorders include glomerulonephritis, diabetic nephropathy, malignant nephrosclerosis, thrombotic microangiopathy syndromes, organ transplant rejection and glomerulopathies. Metabolic disorders include psoriasis, diabetes mellitus, chronic wound healing, inflammation, neurodegenerative diseases, macular degeneration, and diabetic retinopathy.

Inhibitors of kinases involved in mediating or maintaining these disease states represent novel therapies for these disorders. Examples of such kinases include, but are not limited to: (1) inhibition of c-Src (Brickell, Critical Reviews in Oncogenesis 1992, 3, 401–46; Courtneidge, Seminars in Cancer Biology 1994, 5, 239–46), raf (Powis, Pharmacology & Therapeutics 1994, 62, 57–95) and the cyclin-dependent kinases (CDKs) 1, 2 and 4 in cancer (Pines, Current Opinion in Cell Biology 1992, 4, 144–8; Lees, Current Opinion in Cell Biology 1995, 7, 773–80; Hunter and Pines, Cell 1994, 79, 573–82), (2) inhibition of CDK2 or PDGF-R kinase in restenosis (Buchdunger, et al., Proceedings of the National Academy of Science USA 1995, 92, 2258–62), (3) inhibition of CDK5 and GSK3 kinases in Alzheimers (Hosoi, et al., Journal of Biochemistry (Tokyo) 1995, 117, 741–9; Aplin, et al., Journal of Neurochemistry 1996, 67, 699–707), (4) inhibition of c-Src kinase in osteoporosis (Tanaka, et al., Nature 1996, 383, 528–31), (5) inhibition of GSK-3 kinase in type-2 diabetes (Borthwick, et al., Biochemical & Biophysical Research Communications 1995, 210, 738–45); (6) inhibition of the p38 kinase in inflammation (Badger, et al., The Journal of Pharmacology and Experimental Therapeutics 1996, 279, 1453–61); (7) inhibition of VEGF-R 1–3 and TIE-1 and -2 kinases in diseases which involve angiogenesis (Shawver, et al., Drug Discovery Today 1997, 2, 50–63); (8) inhibition of UL97 kinase in viral infections (He, et al., Journal of Virology 1997, 71, 405–11); (9) inhibition of CSF-1 R kinase in bone and hematopoetic diseases (Myers, et al., Bioorganic & Medicinal Chemistry Letters 1997, 7, 421–4), and (10) inhibition of Lck kinase in autoimmune diseases and transplant rejection (Myers, et al., Bioorganic & Medicinal Chemistry Letters 1997, 7,417–20).

It is additionally possible that inhibitors of certain kinases may have utility in the treatment of diseases when the kinase is not misregulated, but is nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle (Vousden; FASEB Journal 1993, 7, 872–9). Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents (Stone, et al., Cancer Research 1996, 56, 3199–202; Kohn, et al., Journal of Cellular Biochemistry 1994, 54, 440–52). Inhibition of CDKs 2 or 4 will prevent progression into the cycle in normal cells and limit the toxicity of cytotoxics which act in S-phase, G2 or mitosis. Furthermore, CDK2/cyclin E activity has also been shown to regulate NF-kB: Inhibition of CDK2 activity stimulates NF-kB-dependent gene expression, an event mediated through interactions with the p300 coactivator (Perkins, et al., Science 1997, 275, 523–7). NF-kB regulates genes involved in inflammatory responses, (such as hematopoietic growth factors chemokines and leukocyte adhesion molecules) (Baeuerle and Henkel, Annual Review of Immunology 1994, 12, 141–79) and may be involved in the suppression of apoptotic signals within the cell (Beg and Baltimore, Science 1996, 274, 782–4; Wang, et al., Science 1996, 274, 784–7; Van Antwerp, et al., Science 1996, 274, 787–9). Thus, inhibition of CDK2 may suppress apoptosis induced by cytotoxic drugs via a mechanism which involves NF-kB. This therefore suggests that inhibition of CDK2 activity may also have utility in other cases where regulation of NF-kB plays a role in etiology of disease. A further example may be taken from fungal infections: Aspergillosis is a common infection in immune-compromised patients (Armstrong, Clinical Infectious Diseases 1993, 16, 1–7). Inhibition of the Aspergillus kinases Cdc2/CDC28 or Nim A (Osmani, et al., EMBO Journal 1991, 10, 2669–79; Osmani, et al., Cell 1991, 67, 283–91) may cause arrest or death in the fungi, improving the therapeutic outcome for patients with these infections.

SUMMARY OF THE INVENTION

In brief summary, the invention comprises compounds of the formula (I):

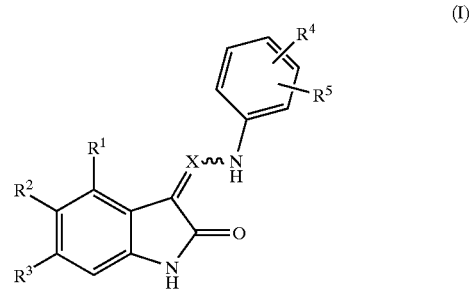

wherein
X is N, CH, CCF$_3$, or C(C$_{1-12}$ aliphatic);
R$^1$ is hydrogen, C$_{1-12}$ aliphatic, thiol, hydroxy, hydroxy-C$_{1-12}$ aliphatic, Aryl, Aryl-C$_{1-12}$ aliphatic, R$^6$-Aryl-C$_{1-12}$ aliphatic, Cyc, Cyc-C$_{1-6}$ aliphatic, Het, Het-C$_{1-12}$ aliphatic, C$_{1-12}$ alkoxy, Aryloxy, amino, C$_{1-12}$ aliphatic amino, di-C$_{1-12}$ aliphatic amino, di-C$_{1-12}$ aliphatic aminocarbonyl, di-C$_{1-12}$ aliphatic aminosulfonyl, C$_{1-12}$ alkoxycarbonyl, halogen, cyano, sulfonamide, or nitro, where R$^6$, Aryl, Cyc and Het are as defined below;
R$^2$ is hydrogen, C$_{1-12}$ aliphatic, N-hydroxyimino-C$_{1-12}$ aliphatic, C$_{1-12}$ alkoxy, hydroxy-C$_{1-12}$ aliphatic, C$_{1-12}$ alkoxycarbonyl, carboxyl C$_{1-12}$ aliphatic, Aryl, R$^6$-Aryl-oxycarbonyl, R$^6$-oxycarbonyl-Aryl, Het, aminocarbonyl, C$_{1-12}$ aliphatic-aminocarbonyl, Aryl-C$_{1-12}$ aliphatic-aminocarbonyl, R$^6$-Aryl-C$_{1-12}$ aliphatic-aminocarbonyl, Het-C$_{1-12}$ aliphatic-aminocarbonyl, hydroxy-C$_{1-12}$ aliphatic-aminocarbonyl, C$_{1-12}$-alkoxy-C$_{1-12}$ aliphatic-aminocarbonyl, C$_{1-12}$ alkoxy-C$_{1-12}$ aliphatic-amino, di-C$_{1-12}$ aliphatic amino, di-C$_{1-12}$ aliphatic aminocarbonyl, di-C$_{1-12}$ aliphatic aminosulfonyl, halogen, hydroxy, nitro, C-$_{1-12}$ aliphatic-sulfonyl, aminosulfonyl, or C$_{1-12}$ aliphatic-aminosulfonyl, where Aryl and Het are as defined below;
further wherein R$^1$ and R$^2$ are optionally joined to form a fused ring, said fused ring selected from the group as defined for Het below, or any of said fused rings optionally substituted by C$_{1-12}$ aliphatic, halogen, nitro, cyano, C$_{1-12}$ alkoxy, carbonyl-C$_{1-12}$ alkoxy or oxo;
R$^3$ is hydrogen, C$_{1-12}$ aliphatic, hydroxy, hydroxy C$_{1-12}$ aliphatic, di-C$_{1-12}$ aliphatic amino, di-C$_{1-12}$ aliphatic aminocarbonyl, di-C$_{1-12}$ aliphatic aminosulfonyl, C$_{1-12}$ alkoxy, Aryl, Aryloxy, hydroxy-Aryl, Het, hydroxy-Het, Het-oxy, or halogen, where Aryl and Het are as defined below;
further wherein R$^2$ and R$^3$ are optionally joined to form a fused ring, said fused ring selected from the group as defined for Het below, or any of said fused rings optionally substituted by $C_{1-6}$ aliphatic or $C_{1-6}$ aliphatic-carbonyl;

with the proviso that $R^1$, $R^2$, and $R^3$ cannot simultaneously be H;

$R^4$ is sulfonic acid, $C_{1-12}$ aliphatic-sulfonyl, sulfonyl-$C_{1-12}$ aliphatic, $C_{1-12}$ aliphatic-sulfonyl-$C_{1-6}$ aliphatic, $C_{1-6}$ aliphatic-amino, $R^7$-sulfonyl, $R^7$-sulfonyl -$C_{1-12}$ aliphatic, $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic amino, di-$C_{1-12}$ aliphatic aminocarbonyl, di-$C_{1-12}$ aliphatic aminosulfonyl, di-$C_{1-12}$ aliphatic amino, di-$C_{1-12}$ aliphatic aminocarbonyl, di-$C_{1-12}$ aliphatic aminosulfonyl-$C_{1-12}$ aliphatic, $(R^8)_{1-3}$-Arylamino, $(R^8)_{1-3}$-Arylsulfonyl, $(R^8)_{1-3}$-Aryl-aminosulfonyl, $(R^8)_{1-3}$-Aryl-sulfonylamino, Het-amino, Het-sulfonyl, Het-aminosulfonyl, aminoiminoamino, or aminoiminoaminosulfonyl, where $R^7$, $R^8$, Aryl and Het are as defined below;

$R^5$ is hydrogen;

and further wherein $R^4$ and $R^5$ are optionally joined to form a fused ring, said ring selected from the group as defined for Het below, or any of said used rings optionally substituted by $C_{1-12}$ aliphatic, oxo or dioxo;

$R^6$ is $C_{1-12}$ aliphatic, hydroxy, $C_{1-12}$ alkoxy, or halogen;

$R^7$ is hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxyalkoxyalkoxyaliphatic, or hydroxyl where Het and Aryl are as defined below;

$R^8$ is hydrogen, nitro, cyano, $C_{1-12}$ alkoxy, halo, carbonyl-$C_{1-12}$ alkoxy or halo-$C_{1-12}$ aliphatic;

Aryl is phenyl, naphthyl, phenanthryl or anthracenyl;

Cyc is cyclopropyl,cyclobutyl, cyclopentyl, cyclohexyl, cycloheptyl or cyclooctyl, any one of which may have one or more degrees of unsaturation;

Het is a saturated or unsaturated heteroatom ring system selected from the group consisting of benzimidazole, dihydrothiophene, dioxin, dioxane, dioxolane, dithiane, dithiazine, dithiazole, dithiolane, furan, imidazole, isoquinoline, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, quinoline, tetrahydrofuran, tetrazine, thidiazine, thiadiazole, thiatriazole, thiazine, thiazole, thiomorpholine, thiophene, thiopyran, triazine and triazole, with the proviso that when $R^2$ is thiadiazine, then $R^4$ cannot be methylsulfone;

and the pharmaceutically acceptable salts, biohydrolyzable esters, biohydrolyzable amides, biohydrolyzable carbamates solvates, hydrates, affinity reagents or prodrugs thereof in either crystalline or amorphous form.

A more preferred genus of compounds of the present invention includes compounds of formula (I), defined as follows:

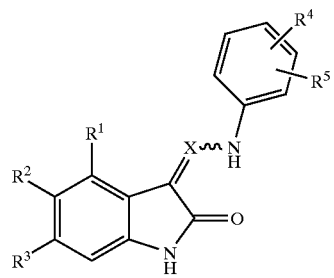

(I)

wherein

X is N, CH, or $C(C_{1-6}$ aliphatic);

$R^1$ is hydrogen, $C_{1-6}$ aliphatic, hydroxy-$C_{1-6}$ aliphatic, Aryl-$C_{1-6}$ aliphatic, $R^6$-Aryl-$C_{1-6}$ aliphatic, Cyc-$C_{1-6}$ aliphatic, Het-$C_{1-6}$ aliphatic, $C_{1-6}$ alkoxy, Aryloxy, aminocarbonyl, di-$C_{1-6}$ aliphatic amino, di-$C_{1-6}$ aliphatic aminocarbonyl, di-$C_{1-6}$ aliphatic aminosulfonyl, $C_{1-6}$ alkoxycarbonyl, halogen, or nitro, where $R^6$, Aryl, Cyc and Het are as defined below;

$R^2$ is hydrogen, $C_{1-6}$ aliphatic, $R^7$-$C_{1-6}$ aliphatic, $C_{1-6}$alkoxy, hydroxy-$C_{1-6}$ aliphatic, $C_{1-6}$ alkoxycarbonyl, carboxyl $C_{1-6}$ aliphatic, Aryl, $R^6$-Aryl-oxycarbonyl, $R^6$-oxycarbonyl-Aryl, Het, aminocarbonyl, $C_{1-6}$ aliphatic-aminocarbonyl, Aryl-$C_{1-6}$ aliphatic-aminocarbonyl, $R^6$-Aryl-$C_{1-6}$ aliphatic-aminocarbonyl, Het-$C_{1-6}$ aliphatic-aminocarbonyl, hydroxy-$C_{1-6}$ aliphatic-aminocarbonyl, $C_{1-6}$-alkoxy-$C_{1-6}$ aliphatic-aminocarbonyl, $C_{1-6}$ alkoxy-$C_{1-6}$ aliphatic-amino, di-$C_{1-6}$ aliphatic amino, di-$C_{1-6}$ aliphatic aminocarbonyl, di-$C_{1-6}$ aliphatic aminosulfonyl, halogen, hydroxy, nitro, sulfo, $C_{1-6}$ aliphatic-sulfonyl, aminosulfonyl, $C_{1-6}$ aliphatic-aminosulfonyl, or quaternary ammonium, where $R^7$, Aryl and Het are as defined below;

further wherein $R^1$ and $R^2$ are optionally joined to form a fused ring, said fused ring selected from the group as defined for Het above, or any of said fused rings optionally substituted by halogen or oxo;

$R^3$ is hydrogen, $C_{1-6}$ aliphatic, hydroxy, hydroxy $C_{1-6}$ aliphatic, di-$C_{1-6}$ aliphatic amino, di-$C_{1-6}$ aliphatic aminocarbonyl, di-$C_{1-6}$ aliphatic aminosulfonyl, $C_{1-6}$ alkoxy, Aryl, Aryloxy, hydroxy-Aryl, Het, hydroxy-Het, Het-oxy, or halogen, where Aryl and Het are as defined below;

further wherein $R^2$ and $R^3$ are optionally joined to form a fused ring, said fused ring selected from the group as defined for Het above, or any of said fused rings optionally substituted by $C_{1-6}$ aliphatic or $C_{1-6}$ aliphatic-carbonyl;

with the proviso that $R^1$, $R^2$ and $R^3$ cannot simultaneously be H;

$R^4$ is sulfonic acid, $C_{1-12}$ aliphatic-sulfonyl, sulfonyl-$C_{1-12}$ aliphatic, $C_{1-12}$ aliphatic-sulfonyl-$C_{1-6}$ aliphatic, $C_{1-6}$ aliphatic-amino, $R^7$-sulfonyl, $R^7$-sulfonyl-$C_{1-12}$ aliphatic, $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic amino, di-$C_{1-12}$ aliphatic aminocarbonyl, di-$C_{1-12}$ aliphatic aminosulfonyl, di-$C_{1-12}$ aliphatic amino, di-$C_{1-12}$ aliphatic aminocarbonyl, di-$C_{1-12}$ aliphatic aminosulfonyl-$C_{1-12}$ aliphatic, $(R^8)_{1-3}$-Arylamino, $(R^8)_{1-3}$-Arylsulfonyl, $(R^8)_{1-3}$-Aryl-aminosulfonyl, $(R^8)_{1-3}$-Aryl-sulfonylamino, Het-amino, Het-sulfonyl, Het-aminosulfonyl, aminoiminoamino, or aminoiminoaminosulfonyl, where $R^7$, $R^8$, Aryl and Het are as defined below;

$R^5$ is hydrogen;

and further wherein $R^4$ and $R^5$ are optionally joined to form a fused ring, said ring selected from the group as defined for Het above, or any of said used rings optionally substituted by oxo or dioxo;

$R^6$ is hydrogen, $C_{1-6}$ aliphatic, hydroxy, $C_{1-6}$ alkoxy, or halogen;

$R^7$ is hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxyalkoxyalkoxyaliphatic, or hydroxyl where Het and Aryl are as defined below;

$R^8$ is hydrogen or halo-$C_{1-6}$ aliphatic;

Aryl is phenyl, or naphthyl;

Cyc is cyclopropyl, cyclobutyl, cyclopentyl, cyclohexyl, cycloheptyl or cyclooctyl, any one of which may have one or more degrees of unsaturation;

Het is a saturated or unsaturated heteroatom ring system selected from the group consisting of benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine tetrahydrofuran, tetrazine, thiadiazine, thiadiazole, thiatriazole, thiazine, thiazole, thiomorpholine, thiophene, thiopyran, triazine and triazole with the proviso that when $R^2$ is thiadiazine, then $R^4$ cannot be methylsulfone; and the pharmaceutically acceptable salts, biohydrolyzable esters, biohydrolyzable amides, biohydrolyzable carbamates, solvates, hydrates, affinity reagents or prodrugs thereof in either crystalline or amorphous form.

A highly preferred genus of compounds of the present invention includes compounds of formula (I), defined as follows:

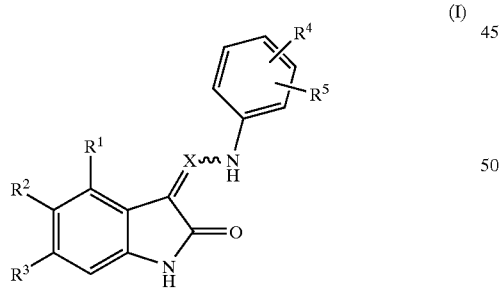

(I)

wherein

X is N, CH, or CCH$_3$;

$R^1$ is hydrogen, $C_{1-6}$ aliphatic, hydroxy-$C_{1-6}$ aliphatic, di-$C_{1-6}$ aliphatic amino, di-$C_{1-6}$ aliphatic aminocarbonyl, di-$C_{1-6}$ aliphatic aminosulfonyl, Aryl-$C_{1-6}$ aliphatic, $R^6$-Aryl-$C_{1-6}$ aliphatic, Cyc-$C_{1-6}$ aliphatic, Het-$C_{1-6}$ aliphatic, $C_{1-6}$ alkoxy, Aryloxy, aminocarbonyl, $C_{1-6}$ alkoxycarbonyl, halogen, or nitro, where $R^6$, Aryl, Cyc and Het are as defined below;

$R^2$ is hydrogen, $C_{1-6}$ aliphatic, N-hydroxyimino-$C_{1-6}$ aliphatic, $C_{1-6}$alkoxy, $C_{1-6}$ alkoxycarbonyl, Aryl, $R^6$-Aryloxycarbonyl, Het, aminocarbonyl, $C_{1-6}$ aliphatic aminocarbonyl, Ary-$C_{1-6}$ aliphatic aminocarbonyl, $R^6$-Aryl-$C_{1-6}$ aliphatic aminocarbonyl, Het-$C_{1-6}$ aliphatic aminocarbonyl, di-$C_{1-6}$ aliphatic amino, di-$C_{1-6}$ aliphatic aminocarbonyl, di-$C_{1-6}$ aliphatic aminosulfonyl, hydroxy-$C_{1-6}$ aliphatic aminocarbonyl, $C_{1-6}$-alkoxy-$C_{1-6}$ aliphatic aminocarbonyl, $C_{1-6}$ alkoxy-$C_{1-6}$ aliphatic amino, halogen, hydroxy, nitro, $C_{1-6}$ aliphatic sulfonyl, or aminosulfonyl, $C_{1-6}$ aliphatic aminosulfonyl, where Aryl and Het are as defined below;

further wherein $R^1$ and $R^2$ are optionally joined to form a fused ring, said fused ring selected from the group as defined for Het below, or any of said fused rings optionally substituted by halogen or oxo;

$R^3$ is hydrogen, $C_{1-6}$ aliphatic, hydroxy, hydroxy $C_{1-6}$ aliphatic, di-$C_{1-6}$ aliphatic amino, di-$C_{1-6}$ aliphatic aminocarbonyl, di-$C_{1-6}$ aliphatic aminosulfonyl $C_{1-6}$ alkoxy, Aryloxy, Het, or halogen, where Aryl and Het are as defined below;

further wherein $R^2$ and $R^3$ are optionally joined to form a fused ring, said fused ring selected from the group as defined for Het below, or any of said fused rings optionally substituted by $C_{1-6}$ alkyl or $C_{1-6}$ alkylcarbonyl;

with the proviso that $R^1$, $R^2$ and $R^3$ cannot simultaneously be H;

$R^4$ is $R^7$-sulfonyl, $R^7$-sulfonyl $C_{1-6}$-aliphatic, $C_{1-6}$ aliphatic sulfonyl-$C_{1-6}$ aliphatic, $R^7$-aminosulfonyl, di-$C_{1-6}$ aliphatic amino, di-$C_{1-6}$ aliphatic aminocarbonyl, di-$C_{1-6}$ aliphatic aminosulfonyl, di-$C_{1-6}$ aliphatic aminosulfonyl-$C_{1-6}$ aliphatic, $R^7$-aminosulfonyl $C_{1-6}$ aliphatic, aminosulfonylamino, $R^7$-$C_{1-6}$ aliphatic aminosulfonyl-$C_{1-6}$ aliphatic, Aryl, Het, $R^8$-Aryl-aminosulfonyl, Het-aminosulfonyl, or aminoiminoaminosulfonyl, where $R^7$, $R^8$, Aryl and Het are as defined below;

$R^5$ is hydrogen;

and further wherein $R^4$ and $R^5$ are optionally joined to form a fused ring, said ring selected from the group as defined for Het below, or any of said used rings optionally substituted by oxo or dioxo;

$R^6$ is hydroxy, $C_{1-6}$ alkoxy, or halogen;

$R^7$ is hydrogen, $C_{1-6}$ aliphatic, hydroxy $C_{1-6}$-alkoxy, hydroxy-$C_{1-6}$ aliphatic, $C_{1-6}$ aliphatic carbonyl, Aryl-carbonyl, $C_{1-12}$ alkoxyalkoxyalkoxyalkoxyalkyl, hydroxyl, Aryl, Aryl-$C_{1-6}$-alkoxy, Aryl-$C_{1-6}$-aliphatic, Het, Het-$C_{1-6}$-alkoxy, di-Het-$C_{1-6}$-alkoxy, Het-$C_{1-6}$-aliphatic, di-Het-$C_{1-6}$-aliphatic;

$R^8$ is trifluoromethyl;

Aryl is phenyl;

Cyc is cyclobutyl;

Het is a saturated or unsaturated heteroatom ring system selected from the group consisting of benzimidazole, dihydrothiophene, dioxolane, furan, imidazole, morpholine, oxazole, pyridine, pyrrole, pyrrolidine, thiadiazole, thiazole, thiophene, and triazole, with the proviso that when $R^2$ is thiadiazine, then $R^4$ cannot be methylsulfone;

and the pharmaceutically acceptable salts, biohydrolyzable esters, biohydrolyzable amides, biohydrolyzable carbamates, solvates, hydrates, affinity reagents or prodrugs thereof in either crystalline or amorphous form.

A preferred group of compounds of the present invention with respect to the substitutions at $R^4$ are compounds of formula (I):

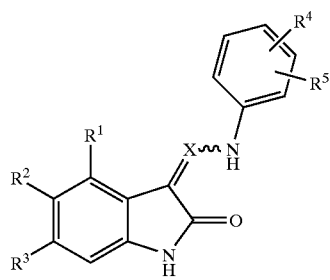

(I)

wherein

X is NH;

$R^1$ is hydrogen, $C_{1-12}$ aliphatic, thiol, hydroxy, hydroxy-$C_{1-12}$ aliphatic, Aryl, Aryl-$C_{1-12}$ aliphatic, $R^6$-Aryl-$C_{1-12}$ aliphatic, Cyc, Cyc-$C_{1-6}$ aliphatic, Het, Het-$C_{1-12}$ aliphatic, $C_{1-12}$ alkoxy, Aryloxy, amino, $C_{1-12}$ aliphatic amino, di-$C_{1-12}$ aliphatic amino, di-$C_{1-12}$ aliphatic aminocarbonyl, di-$C_{1-12}$ aliphatic aminosulfonyl, $C_{1-12}$ alkoxycarbonyl, halogen, cyano, sulfonamide, or nitro, where $R^6$, Aryl, Cyc and Het are as defined below;

$R^2$ is hydrogen, $C_{1-12}$ aliphatic, N-hydroxyimino-$C_{1-12}$ aliphatic, $C_{1-12}$ alkoxy, hydroxy-$C_{1-12}$ aliphatic, $C_{1-12}$ alkoxycarbonyl, carboxyl $C_{1-12}$ aliphatic, Aryl, $R^6$-Ary-oxycarbonyl, $R^6$-oxycarbonyl-Aryl, Het, aminocarbonyl, $C_{1-12}$ aliphatic-aminocarbonyl, Aryl-$C_{1-12}$ aliphatic-aminocarbonyl, $R^6$-Aryl-$C_{1-12}$ aliphatic-aminocarbonyl, Het-$C_{1-12}$ aliphatic-aminocarbonyl, hydroxy-$C_{1-12}$ aliphatic-aminocarbonyl, $C_{1-12}$-alkoxy-$C_{1-12}$ aliphatic-aminocarbonyl, $C_{1-12}$ alkoxy-$C_{1-12}$ aliphatic-amino, di-$C_{1-12}$ aliphatic amino, di-$C_{1-12}$ aliphatic aminocarbonyl, di-$C_{1-12}$ aliphatic aminosulfonyl, halogen, hydroxy, nitro, $C_{1-12}$ aliphatic-sulfonyl, aminosulfonyl, or $C_{1-12}$ aliphatic-aminosulfonyl, where Aryl and Het are as defined below;

further wherein $R^1$ and $R^2$ are optionally joined to form a fused ring, said fused ring selected from the group as defined for Het below, or any of said fused rings optionally substituted by halogen, nitro, cyano, $C_{1-12}$ alkoxy, carbonyl-$C_{1-12}$ alkoxy or oxo;

$R^3$ is hydrogen, $C_{1-12}$ aliphatic, hydroxy, hydroxy $C_{1-12}$ aliphatic, di-$C_{1-12}$ aliphatic amino, di-$C_{1-12}$ aliphatic aminocarbonyl, di-$C_{1-12}$ aliphatic aminosulfonyl, $C_{1-12}$ alkoxy, Aryl, Aryloxy, hydroxy-Aryl, Het, hydroxy-Het, Het-oxy, or halogen, where Aryl and Het are as defined below;

further wherein $R^2$ and $R^3$ are optionally joined to form a fused ring, said fused ring selected from the group as defined for Het below, or any of said fused rings optionally substituted by $C_{1-6}$ aliphatic or $C_{1-6}$ aliphatic-carbonyl;

with the proviso that $R^1$, $R^2$ and $R^3$ cannot simultaneously be H;

$R^4$ is $R^7$-aminosulfonyl, $R^7$-aminosulfonyl-$C_{1-12}$ aliphatic, $R^7$-sulfonylamino, $R^7$-sulfonylamino-$C_{1-12}$ aliphatic, aminosulfonylamino, di-$C_{1-12}$ aliphatic aminosulfonyl, di-$C_{1-12}$ aliphatic aminosulfonyl-$C_{1-12}$ aliphatic, $(R^8)_{1-3}$-Aryl-aminosulfonyl, $(R^8)_{1-3}$-Aryl-sulfonylamino, or aminoiminoaminosulfonyl, where $R^7$, $R^8$, Aryl and Het are as defined below;

$R^5$ is hydrogen;

$R^6$ is $C_{1-12}$ aliphatic, hydroxy, $C_{1-12}$ alkoxy, or halogen;

$R^7$ is hydrogen, $C_{1-12}$ aliphatic, $C_{1-12}$ alkoxy, hydroxy-$C_{1-12}$ alkoxy, hydroxy-$C_{1-12}$ aliphatic, carboxylic acid, $C_{1-12}$ aliphatic-carbonyl, Het, Het-$C_{1-12}$-aliphatic, Het-$C_{1-12}$-alkoxy, di-Het-$C_{1-12}$-alkoxy Aryl, Aryl-$C_{1-12}$-aliphatic, Aryl-$C_{1-12}$-alkoxy, Aryl-carbonyl, $C_{1-18}$ alkoxyalkoxyalkoxyalkoxyaliphatic, or hydroxyl where Het and Aryl are as defined below;

$R^8$ is hydrogen, nitro, cyano, $C_{1-12}$ alkoxy, halo, carbonyl-$C_{1-12}$ alkoxy or halo-$C_{1-12}$ aliphatic;

Aryl is phenyl, naphthyl, phenanthryl or anthracenyl;

Cyc is cyclopropyl, cyclobutyl, cyclopentyl, cyclohexyl, cycloheptyl or cyclooctyl, any one of which may have one or more degrees of unsaturation;

Het is a saturated or unsaturated heteroatom ring system selected from the group consisting of benzimidazole, dihydrothiophene, dioxin, dioxane, dioxolane, dithiane, dithiazine, dithiazole, dithiolane, furan, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine and triazole with the proviso that when $R^2$ is thiadiazine, then $R^4$ cannot be methylsulfone;

and the pharmaceutically acceptable salts, biohydrolyzable esters, biohydrolyzable amides, biohydrolyzable carbamates solvates, hydrates, affinity reagents or prodrugs thereof in either crystalline or amorphous form.

Due to the presence of an oxindole exocyclic double bond, also included in the compounds of the invention are their respective pure E and Z geometric isomers as well as mixtures of E and Z isomers. The invention as described and claimed does not set any limiting ratios on prevalence of Z to E isomers. Thus compound number 104 in the tables below is disclosed and claimed as the E geometric thereof, the Z geometric isomer thereof and a mixture of the E and Z geometric isomers thereof, but not limited by any given ratio(s).

Likewise, it is understood that compounds of formula (I) may exist in tautomeric forms other than that shown in the formula.

Certain of the compounds as described will contain one or more chiral, or asymmetric, centers and will therefore be capable of existing as optical isomers that are either dextrorotatory or levorotatory. Also included in the compounds of the invention are the respective dextrorotatory or levorotatory pure preparations, and mixtures thereof.

Certain compounds of formula (I) above may exist in stereoisomeric forms (e.g. they may contain one or more asymmetric carbon atoms or may exhibit cis-trans isomerism). The individual stereoisomers (enantiomers and diastereoisomers) and mixtures of these are included within the scope of the present invention. Likewise, it is understood that compounds of formula (I) may exist in tautomeric forms other than that shown in the formula and these are also included within the scope of the present invention.

The present invention also provides compound of formula (I) and pharmaceutically acceptable salts thereof (hereafter identified as the 'active compounds') for use in medical therapy, and particularly in the treatment of disorders mediated by CDK2 activity, such as alopecia induced by cancer chemotherapy.

A further aspect of the invention provides a method of treatment of the human or animal body suffering from a disorder mediated by a mitogen activated protein kinase which comprises administering an effective amount of an active compound of formula (I) to the human or animal patient.

Another aspect of the present invention provides the use of an active compound of formula (I), in the preparation of a medicament for the treatment of malignant tumors, or for the treatment of alopecia induced by cancer chemotherapy or induced by radiation therapy. Alternatively, compounds of formula (I) can be used in the preparation of a medicament for the treatment of a disease mediated by a kinase selected from the group consisting of abl, ATK, bcr-abl, Blk, Brk, Btk, c-kit, c-met, c-src, CDK1, CDK2, CDK4, CDK6, cRaf1, CSF1R, CSK, EGFR, ErbB2, ErbB3, ErbB4, ERK, Fak, fes, FGFR1, FGFR2, FGFR3, FGFR4, FGFR5, Fgr, FLK-4, flt-1, Fps, Frk, Fyn, Hck, IGF-1R, INS-R, Jak, KDR, Lck, Lyn, MEK, p38, PDGFR, PIK, PKC, PYK2, ros ,$tie_1$, $tie_2$, TRK, Yes, and Zap70. Additionally, compounds of formula (I) can be used in the preparation of a medicament for the treatment of organ transplant rejection, of inhibiting tumor growth, of treating chemotherapy-induced alopecia, chemotherapy-induced thrombocytopenia or chemotherapy-induced leukopenia, or of treating a disease state selected from the group consisting of mucocitis, restenosis, atherosclerosis, rheumatoid arthritis, angiogenesis, hepatic cirrhosis, glomerulonephritis, diabetic nephropathy, malignant nephrosclerosis, thrombotic microangiopathy, a glomerulopathy, psoriasis, diabetes mellitus, inflammation, a neurodegenerative disease, macular degeneration, actinic keratosis and hyperproliferative disorders.

Another aspect of the present invention provides the use of an active compound of formula (I), in coadministration with previously known anti-tumor therapies for more effective treatment of such tumors.

Another aspect of the present invention provides the use of an active compound of formula (I) in the preparation of a medicament for the treatment of viral or eukaryotic infections.

Other aspects of the present invention related to the inhibition-of mitogen-activated protein kinases are discussed in more detail below.

Compounds we have synthesized as part of the present invention which are currently preferred are listed in Tables 1 and 2 below. Compounds are identified by the numbers shown in the first column; variables below in the rest of the columns are with reference to the generic structure (I). Corresponding IUPAC nomenclature are disclosed in Table 2. Since all substituents at each point of substitution are capable of independent synthesis of each other, the tables are to be read as a matrix in which any combination of substituents is within the scope of the disclosure and claims of the invention.

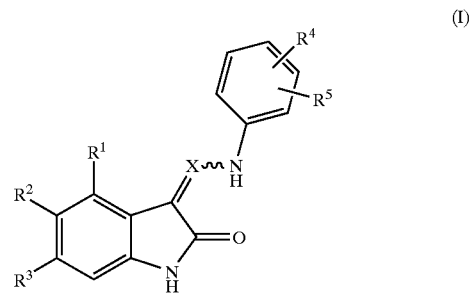
(I)

TABLE 1

(I)

| Example | $R^1$ | $R^2$ | $R^3$ | $R^4$ | $R^5$ | X |
|---|---|---|---|---|---|---|
| 1 | —$NO_2$ | H | H | 4'-$SO_2NH_2$ | H | N |
| 2 | —$CONH_2$ | H | H | 4'-$SO_2NH_2$ | H | N |
| 3 | —$CH(CH_3)_2$ | H | H | 4'-$SO_2NH_2$ | H | N |
| 4 | —$CH_2OH$ | H | H | 4'-$SO_2NHCH_3$ | H | CH |
| 5 | —$CH_2CH_2$-(pyridyl) | H | H | 4'-$SO_2NH_2$ | H | N |
| 6 | —$CO_2CH_2CH_3$ | H | H | 4'-$SO_2NH_2$ | H | CH |
| 7 | I | H | H | 4'-$SO_2NH_2$ | H | N |
| 8 | —$CH_2CH(CH_3)_2$ | H | H | 4'-$SO_2NH_2$ | H | N |
| 9 | —CH=$C(CH_3)_2$ | H | H | 4'-$SO_2NH_2$ | H | N |
| 10 | —CH=$C(CH_3)CH_2CH_3$ and —$CH_2C(CH_3)$=$CHCH_3$ | H | H | 4'-$SO_2NH_2$ | H | N |
| 11 | —$CH_2CH(CH_3)CH_2CH_3$ | H | H | 4'-$SO_2NH_2$ | H | N |

TABLE 1-continued

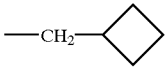

(I)

| Example | R¹ | R² | R³ | R⁴ | R⁵ | X |
|---|---|---|---|---|---|---|
| 12 | 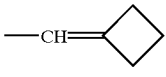 | H | H | 4'-SO₂NH₂ | H | N |
| 13 | 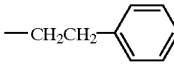 | H | H | 4'-SO₂NH₂ | H | N |
| 14 | 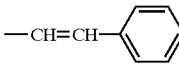 | H | H | 4'-SO₂NH₂ | H | N |
| 15 | 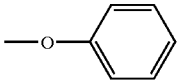 trans | H | H | 4'-SO₂NH₂ | H | N |
| 16 | 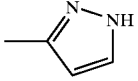 | H | H | 4'-SO₂NH₂ | H | N |
| 17 | OCH(CH₃)₂ | H | H | 4'-SO₂NH₂ | H | N |
| 18 | 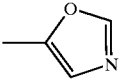 | H | H | 4'-SO₂NH₂ | H | N |
| 19 | H | 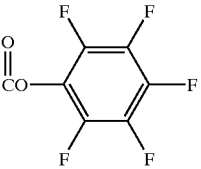 | H | 4'-SO₂NH₂ | H | CH |
| 20 | H |  | H | 4'-SO₂NH₂ | H | N |
| 21 | H | —NO₂ | H | 4'-SO₂NH₂ | H | N |
| 22 | H | —OH | H | 4'-SO₂NH₂ | H | N |
| 23 | H | —CH₃ | H | 4'-SO₂NH₂ | H | N |
| 24 | H |  | H | 4'-SO₂NHCH₃ | H | N |
| 25 | H | —SO₃⁻Na⁺ | H | 4'-SO₂NH₂ | H | N |
| 26 | H | —CONH₂ | H | 4'-SO₂NHCH₃ | H | N |
| 27 | H | —CO₂CH₃ | H | 4'-SO₂NH₂ | H | CH |
| 28 | H | Br | H | 4'-SO₂CH₃ | H | N |
| 29 | H | I | H | —NH—N=N— | | CH |
| 30 | H | —SO₂NH₂ | H | 4'-SO₂NH₂ | H | N |
| 31 | H | —SO₂CH₃ | H | 4'-SO₂NH₂ | H | N |
| 32 | H | —SO₂NHCH₃ | H | 4'-SO₂NHCH₃ | H | N |

TABLE 1-continued

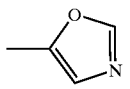

(I)

| Example | R¹ | R² | R³ | R⁴ | R⁵ | X |
|---|---|---|---|---|---|---|
| 33 | H | —C(=NOH)CH₃ | H | 4'-SO₂NHCH₃ | H | N |
| 34 | H | 5-methyloxazolyl 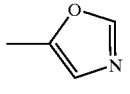 | H | 4'-SO₂NH₂ | H | CCH₃ |
| 35 | H | 5-methyloxazolyl 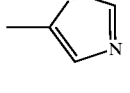 | H | 4'-SO₂N(CH₃)₂ | H | CH |
| 36 | H | 5-methyloxazolyl 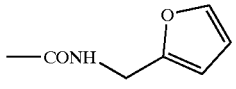 | H | 4'-SO₂NH₂ | H | N |
| 37 | H | -phenyl | H | 4'-SO₂NH₂ | H | CH |
| 38 | H | —CON(CH₃)₂ | H | 4'-SO₂NH₂ | H | N |
| 39 | H | —CONH-CH₂-furyl 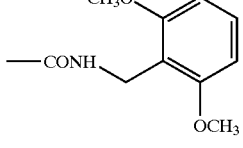 | H | 4'-SO₂NH₂ | H | N |
| 40 | H | —CONH-CH₂-(2,6-dimethoxyphenyl) 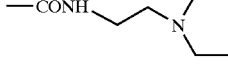 | H | 4'-SO₂NH₂ | H | N |
| 41 | H | —CONH-(CH₂)₂-morpholinyl 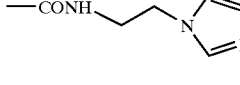 | H | 4'-SO₂NH₂ | H | N |
| 42 | H | —CONH-(CH₂)₂-imidazolyl 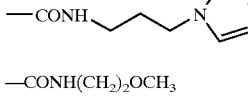 | H | 4'-SO₂NH₂ | H | N |
| 43 | H | —CONH-(CH₂)₃-imidazolyl 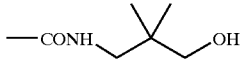 | H | 4'-SO₂NH₂ | H | N |
| 44 | H | —CONH(CH₂)₂OCH₃ | H | 4'-SO₂NH₂ | H | N |
| 45 | H | —CONH(CH₂)₂OH | H | 4'-SO₂NH₂ | H | N |
| 46 | H | —CONH(CH₂)₃OH | H | 4'-SO₂NH₂ | H | N |
| 47 | H | —CONH-C(CH₃)₂-CH₂OH | H | 4'-SO₂NH₂ | H | N |
| 48 | H | —CONH-CH₂-pyridyl 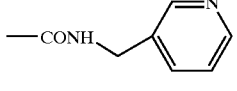 | H | 4'-SO₂NH₂ | H | N |

TABLE 1-continued

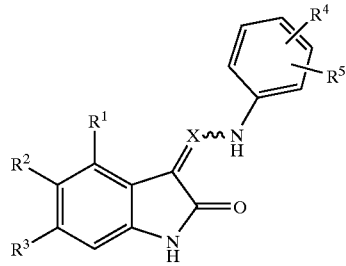

(I)

| Example | R¹ | R² | R³ | R⁴ | R⁵ | X |
|---|---|---|---|---|---|---|
| 49 | H | —CONH—CH₂-(4-pyridyl) | H | 4'-SO₂NH₂ | H | N |
| 50 | H | —OCH₃ | H | 4'-SO₂NH₂ | H | N |
| 51 | H | —NH₃⁺Cl⁻ | H | 4'-SO₂NH₂ | H | N |
| 52 | H | H | —CH₂CH₃ | 4'-SO₂NH₂ | H | N |
| 53 | H | H | H | SO₂OC₆H₅ | H | CH |
| 54 | H | H | H | 4'-NHSO₂NH₂ | H | CH |
| 55 | H | H | —CH₂OH | 4'-SO₂NH₂ | H | CH |
| 56 | H | H | Br | 4'-SO₂NH₂ | H | N |
| 57 | H | H | —O-phenyl | 4'-SO₂NH₂ | H | N |
| 58 | H | H | —OCH₂CH₃ | 4'-SO₂NH₂ | H | N |
| 59 | | —SCH=N— | H | 4'-SO₂NH(CH₂)₂O(CH₂)₂OH | H | CH |
| 60 | | —SCH=N— | H | 4'-SO₂NH(CH₂)₂OH | H | CH |
| 61 | —CH₃ | —NO₂ | H | 4'-SO₂NHCH₃ | H | N |
| 62 | | —CH=NNH— | H | 4'-SO₂NH₂ | H | N |
| 63 | | —NH—N=CH— | H | 4'-SO₂NH₂ | H | N |
| 64 | | —N—N=NH— | H | 4'-SO₂NH₂ | H | N |
| 65 | | —C(Cl)=NNH— | H | 4'-SO₂NH₂ | H | N |
| 66 | | —C(O)NHCH₂— | H | 4'-SO₂NHCH₃ | H | N |
| 67 | | —SCH=N— | H | 4'-CH₂SO₂NHCH₂C(CH₃)₂CH₂OH | H | CH |
| 68 | | —CH=CHCH=N— | H | 4'-CH₂SO₂NHCH₃ | H | N |
| 69 | | —SCH=N— | H | 4-SO₂NH-(1H-indazol-6-yl) | H | CH |
| 70 | | —SCH=N— | H | 4-SO₂NH-(thiazol-2-yl) | H | CH |
| 71 | | —SCH=N— | H | 4'-SO₂NH—C(=NH)NH₂ | H | CH |
| 72 | | —SCH=N— | H | 4-SO₂NH-(pyridin-2-yl) | H | CH |
| 73 | | —SCH=N— | H | —CH₂SO₂CH₂— | | CH |
| 74 | | —SCH=N— | H | 4'-CH₂SO₂NH₂ | H | CH |
| 75 | | —SCH=N— | H | 4'-CH₂SO₂NHCH₂CH=CH₂ | H | CH |
| 76 | | —SCH=N— | H | 4'-CH₂SO₂CH₃ | H | CH |
| 77 | | —SCH=N— | H | 4'-SO₂NHCH₂C(CH₃)₂CH₂OH | H | CH |
| 78 | | —SCH=N— | H | 4-SO₂NH-(3-trifluoromethylphenyl) | H | CH |

TABLE 1-continued

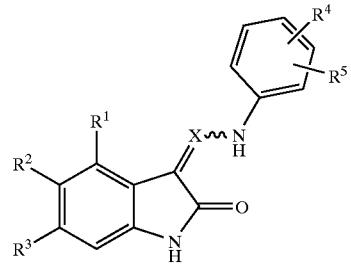

| Example | R¹ | R² | R³ | R⁴ | R⁵ | X |
|---|---|---|---|---|---|---|
| 79 | | —SCH=N— | H | 4'-SO$_2$NH-(pyrimidin-2-yl) | H | CH |
| 80 | | —SCH=N— | H | 4'-SO$_2$NH-(5-methyl-1,3,4-thiadiazol-2-yl) | H | CH |
| 81 | | —SCH=N— | H | 4'-SO$_2$NHCOCH$_3$ | H | CH |
| 82 | | —SCH=N— | H | 4'-SO$_2$NHCO-phenyl | H | CH |
| 83 | | —SCH=N— | H | 4'-SO$_2$NHCH$_3$ | H | N |
| 84 | | —SCH=N— | H | 4'-SO$_2$N(CH$_3$(CH$_2$)$_2$O(CH$_2$)$_2$OH | H | CH |
| 85 | | —SCH=N— | H | 4'-SO$_2$NH[(CH$_2$)$_2$O]$_4$CH$_3$ | H | CH |
| 86 | H | —CH$_3$ | —CH$_3$ | 4'-SO$_2$NH$_2$ | H | N |
| 87 | H | —NHCOCH$_3$ | —OH | 4'-CH$_2$SO$_2$NHCH$_3$ | H | N |
| 88 | H | —OCH$_3$ | Cl | 4'-SO$_2$NH$_2$ | H | N |
| 89 | H | —OH | —CH(CH$_3$)$_2$ | 4'-SO$_2$NH$_2$ | H | N |
| 90 | H | —N=C(CH$_3$O— | | 4'-SO$_2$NH$_2$ | H | N |
| 91 | H | —N(COCH$_3$)(CH$_2$)$_2$— | | 4'-SO$_2$NH$_2$ | H | N |
| 92 | H | —OCH$_2$O— | | 4'-SO$_2$NH$_2$ | H | N |
| 93 | H | —NH$_2$⁺(Br)(CH$_2$)$_2$— | | 4'-SO$_2$NH$_2$ | H | N |
| 94 | Cl | —OCH$_3$ | Cl | 4'-CH$_2$SO$_2$NHCH$_3$ | H | N |
| 95 | Cl | —OH | —CH$_3$ | 4'-SO$_2$NH$_2$ | H | N |
| 96 | —CH$_3$ | —OH | —CH$_3$ | 4'-SO$_2$NH$_2$ | H | N |
| 97 | H | H | H | —NHN=CH— | | CH |
| 98 | H | H | H | —CH=NNH— | | CH |
| 99 | —CH$_3$ | —OH | —CH$_3$ | 4'-CH$_2$SO$_2$NHCH$_3$ | H | N |
| 100 | H | (5-methyl-oxazol-4-yl) | H | 4'-CH$_2$SO$_2$NHCH$_3$ | H | CH |
| 101 | | —SCH=N— | H | —N=N—NH— | | CH |
| 102 | | —CH=CHCH=N— | H | 4'-SO$_2$NH$_2$ | H | N |
| 103 | H | —CO$_2$CH$_2$CH(CH$_3$)$_2$ | H | 4'-SO$_2$NH$_2$ | H | CH |
| 104 | | —SCH=N— | H | 4'-SO$_2$NHCH$_2$-(pyridin-4-yl) | H | CH |

Standard accepted nomenclature corresponding to the Examples set forth in this specification are set forth below. In some cases nomenclature is given for one or more possible isomers.

Example 1: 4-[N'-(4-Nitro-2-oxo-1,2-dihydro-indol-3-ylidene)-hydrazino]-benzenesulfonamide (Z isomer).

Example 2: 2-Oxo-3-[(4-sulfamoyl-phenyl)-hydrazono]-2,3-dihydro-1H-indole-4-carboxylic acid amide (E isomer).

Example 3: 4-[N'-(4-Isopropyl-2-oxo-1,2-dihydro-indol-3-ylidene)-hydrazino]-benzenesulfonamide (Z isomer).

Example 4: 4-[(4-Hydroxymethyl-2-oxo-1,2-dihydro-indol-3-ylidenemethyl)-amino]-N-methyl-benzenesulfonamide (Z-isomer).

Example 5: 4-{N'-[2-Oxo-4-(2-pyridin-4-yl-ethyl)-1,2-dihydro-indol-3-ylidene]-hydrazino}-benzenesulfonamide (Z isomer).

Example 6: 2-Oxo-3-(4-sulfamoyl-phenylamino-methylene)-2,3-dihydro-1H-indole-4-carboxylic acid ethyl ester (Z-isomer).

Example 7: 4-[N'-(4-Iodo-2-oxo-1,2-dihydro-indol-3-ylidene)-hydrazino]-benzenesulfonamide (Z-isomer).

Example 8: 4-[N'-(4-Isobutyl-2-oxo-1,2-dihydro-indol-3-ylidene)-hydrazino]-benzenesulfonamide (Z-isomer).

Example 9: 4-{N'-[4-(2-Methyl-propenyl)-2-oxo-1,2-dihydro-indol-3-ylidene]-hydrazino}-benzenesulfonamide (Z-isomer).

Example 10: 4-{N'-[4-(2-Methyl-1-butenyl)-2-oxo-1,2-dihydro-indol-3-ylidene]hydrazino}-benzenesulfonamide and 4-{N'-[4-(2-methyl-2-butenyl)-2-oxo-1,2-dihydro-indol-3-ylidene]-hydrazino}-benzenesulfonamide (Z-isomer).

Example 11: 4-{N'-[4-(2-methylbutyl)-2-oxo-1,2-dihydro-indol-3-ylidene]-hydrazino}-benzenesulfonamide (Z-isomer).

Example 12: 4-[N'-(4-Cyclobutylmethyl-2-oxo-1,2-dihydro-indol-3-ylidene)-hydrazino]-benzenesulfonamide (Z isomer).

Example 13: 4-[N'-(4-Cyclobutylidenemethyl-2-oxo-1,2-dihydro-indol-3-ylidene)-hydrazino]-benzenesulfonamide (Z isomer).

Example 14: 4-(N'-{4-[2-(4-Hydroxyphenyl)-ethyl]-2-oxo-1,2-dihydro-indol-3-ylidene}-hydrazino)-benznensulfonamide (Z-isomer).

Example 15: 4-(N'-{4-[2-(4-Hydroxyphenyl)-vinyl]-2-oxo-1,2-dihydro-indol-3-ylidene}-hydrazino)-benznensulfonamide (Z-isomer).

Example 16: 4-[N'-(2-Oxo-4-phenoxy-1,2-dihydro-indol-3-ylidene)-hydrazino-benzenesulfonamide (mixture of E and Z isomers).

Example 17: 4-[N'-(4-Isopropoxy-2-oxo-1,2-dihydro-indol-3-ylidene)-hydrazino]-benzenesulfonamide (Z-isomer).

Example 18: 4-{N'-[2-Oxo-4-(1H-pyrazol-3-yl)-1,2-dihydro-indol-3-ylidene]-hydrazino}-benzenesulfonamide (Z-isomer).

Example 19: 4-[(5-Oxazol-5-yl-2-oxo-1,2-dihydro-indol-3-ylidenemethyl)-amino]benzenesulfonamide (Z-isomer).

Example 20: 2-Oxo-3-[(4-sulfamoyl-phenyl)-hydrazone]-2,3-dihydro-1H-indole-5-carboxylic acid 2,3,4,5,6-pentafluorophenyl ester (Z-isomer).

Example 21: 4-[N'-(5-Nitro-2-oxo-1,2-dihydro-indol-3-ylidene)-hydrazino]-benzenesulfonamide (Z isomer).

Example 22: 4-[N'-(5-Hydroxy-2-oxo-1,2-dihydro-indol-3-ylidene)-hydrazino]-benzenesulfonamide (Z-isomer).

Example 23: 4-[N'-(5-Methyl-2-oxo-1,2-dihydro-indol-3-ylidene)-hydrazino]-benzenesulfonamide (E isomer).

Example 24: N-Methyl-4-[N'-(2-oxo-5-[1,2,4]triazol-1-yl-1,2-dihydro-indol-3-ylidene)hydrazino]-benzenesulfonamide (Z-isomer).

Example 25: 2-Oxo-3-[(4-sulfamoyl-phenyl)-hydrazono]-2,3-dihydro-1H-indole-5-sulfonic acid sodium salt (Z-isomer).

Example 26: 3-[(4-Methylsulfamoyl-phenyl)hydrazono]-2-oxo-2,3-dihydro-1H-indole-5-carboxylic acid amide (Z-isomer).

Example 27: 2-Oxo-3-(4-sulfamoyl-phenylamino-methylene)-2,3-dihydro-1H-indole-5-carboxylic acid methyl ester (Z-isomer).

Example 28: 5-Bromo-3-[(4-Methylsulfonyl-phenyl)-hydrazono]-1,3-dihydro-indol-2-one (Z-isomer).

Example 29: 3-(3H-benzotriazol-5-ylamino-methylene)-5-iodo-1,3-dihydro-indol-2-one (Z-isomer).

Example 30: 2-Oxo-3-[(4-sulfamoyl-phenyl)-hydrazono]-2,3-dihydro-1H-indole-5-sulfonic acid amide (Z-isomer).

Example 31: 4-[N'-(5-Methylsulfonyl-2-oxo-1,2-dihydro-indol-3-ylidene)-hydrazino]-benzenesulfonamide (Z-isomer).

Example 32: 3-[(4-Methylsulfamoyl-phenyl)-hydrazono]-2-oxo-2,3-dihydro-1H-indole-5-sulfonic acid methylamide (Z-isomer).

Example 33: 4-{N'-[5-(1-Hydroxyimino-ethyl)-2-oxo-1,2-dihydro-indol-3-ylidene]-hydrazino}-N-methyl-benzenesulfonamide (Z-isomer).

Example 34: 4-[1-(5-Oxazol-5-yl-2-oxo-1,2-dihydro-indol-3-ylidene)-ethylamino]-benzenesulfonamide (Z-isomer).

Example 35: N,N-Dimethyl-4-[(5-oxazol-5-yl-2-oxo-1,2-dihydro-indol-3-ylidenemethyl)-amino]-benzenesulfonamide (Z-isomer).

Example 36: 4-[1-(5-Oxazol-5-yl-2-oxo-1,2-dihydro-indol-3-ylidene)-hydrazino]-benzenesulfonamide (mixture of E and Z isomers).

Example 37: 4-[(2-Oxo-5-phenyl-1,2-dihydro-indol-3-ylidenemethyl)-amino]-benzenesulfonamide (Z-isomer).

Example 38: 2-Oxo-3[(4-sulfamoyl-phenyl)-hydrazono]-2,3-dihydro-1H-indole-5-carboxylic acid dimethylamide (Z-isomer).

Example 39: 2-Oxo-3-[(4-sulfamoyl-phenyl)-hydrazono]-2,3-dihydro-1H-indol-5-carboxylic acid (furan-2-ylmethyl)-amide (Z-isomer).

Example 40: 2-Oxo-3-[(4-sulfamoyl-phenyl)-hydrazono]-2,3-dihydro-1H-indol-5-carboxylic acid -2,6-dimethoxy-benzylamide (Z-isomer).

Example 41: 2-Oxo-3[(4-sulfamoyl-phenyl)-hydrazono]-2,3-dihydro-1H-indole-5-carboxylic acid(2-morpholin-4-yl-ethyl)-amide (Z-isomer).

Example 42: 2-Oxo-3-[(4-sulfamoyl-phenyl)-hydrazono]-2,3-dihydro-1H-indole-5-carboxylic acid (2-imidazol-1-yl-ethyl)-amide (Z-isomer).

Example 43: 2-Oxo-3-[(4-sulfamoyl-phenyl)-hydrazono]-2,3-dihydro-1H-indole-5-carboxylic acid (3-imidazol-1-yl-propyl)-amide (Z-isomer).

Example 44: 2-Oxo-3-[(4-sulfamoyl-phenyl)-hydrazono]-2,3-dihydro-1H-indole-5-carboxylic acid (2-methoxyethyl)-amide (Z-isomer).

Example 45: 2-Oxo-3-[(4-sulfamoyl-phenyl)-hydrazono]-2-3-dihydro-1H-indole-5-carboxylic acid (2-hydroxyethyl)-amide (Z-isomer).

Example 46: 2-Oxo-3-[(4-sulfamoyl-phenyl)-hydrazono]-2,3-dihydro-1H-indole-5-carboxylic acid (3-hydroxypropyl)-amide (Z-isomer).

Example 47: 2-Oxo-3-[(4-sulfamoyl-phenyl)-hydrazono]-2,3-dihydro-1H-indole-5-carboxylic acid (3-hydroxy-2,2-dimethylpropyl)-amide (Z-isomer).

Example 48: 2-Oxo-3-[(4-sulfamoyl-phenyl)-hydrazono]-2,3-dihydro-1H-indole-5-carboxylic acid (pyridin-3-ylmethyl)-amide (Z-isomer).

Example 49: 2-Oxo-3-[(4-sulfamoyl-phenyl)-hydrazono]-2,3-dihydro-1H-indole-5-carboxylic acid (pyridin-4-ylmethyl)-amide (Z-isomer).

Example 50: 4-[N'-(5-Methoxy-2-oxo-1,2-dihydro-indol-3-ylidene)-hydrazino]-benzenesulfonamide (Z-isomer).

Example 51: 4-[N'-(5-Amino-2-oxo-1,2-dihydro-indol-3-ylidene)-hydrazino]-benzenesulfonamide hydrochloride (Z-isomer).

Example 52: 4-[N'-(6-Ethyl-2-oxo-1,2-dihydro-indol-3-ylidene)-hydrazino]-benzenesulfonamide (Z isomer).

Example 53: 4-[(2-Oxo-1,2-dihydro-indol-3-ylidenemethyl)-amino]-benzensulfonic-acid-phenyl-ester (Z-isomer).
Example 54: N-{4-[(2-Oxo-1,2-dihydro-indol-3-ylidenemethyl)-amino]-phenyl}sulfamide (Z-isomer).
Example 55: 4-[(6-Hydroxymethyl-2-oxo-1,2-dihydro-indol-3-ylidenemethyl)-amino]-benzenesulfonamide (Z-isomer).
Example 56: 4-[N'-(6-Bromo-2-oxo-1,2-dihydro-indol-3-ylidene)-hydrazino]-benzenesulfonamide (Z-isomer).
Example 57: 4-[N'-(2-Oxo-6-phenoxy-1,2-dihydro-indol-3-ylidene)-hydrazino]-benzenesulfonamide (Z-isomer).
Example 58: 4-[N'-(6-Ethoxy-2-oxo-1,2-dihydro-indol-3-ylidene)-hydrazino]-benzenesulfonamide (Z-isomer).
Example 59: N-[2-(2-Hydroxyethoxy)ethyl]-4-[7-oxo-6,7-dihydro-1-thia-3,6-diaza-as-indacene-8-ylidenemethyl)-amino]benzenesulfonamide (Z-isomer).
Example 60: N-[2-(2-Hydroxyethyl]-4-[7-oxo-6,7-dihydro-1-thia-3,6-diaza-as-indacene-8-ylidenemethyl)-amino]benzenesulfonamide (Z-isomer).
Example 61: N-Methyl-4-[N'-(4-methyl-5-nitro-2-oxo-1,2-dihydro-indol-3-ylidene)-hydrazino]-benzenesulfonamide (Z-isomer).
Example 62: 4-[N'-(7-Oxo-6,7-dihydro-3H-pyrrolo[3,2-e]indazol-8-ylidene)-hydrazino]-benzenesulfonamide (Z isomer).
Example 63: 4-[N'-(7-Oxo-6,7-dihydro-1H-pyrrolo[2,3-g]indazol-8-ylidene)-hydrazino]-benzenesulfonamide (mixture of E and Z isomers).
Example 64: 4-[N'-(7-Oxo-6,7-dihydro-3H-1,2,3,6-tetraaza-as-indacen-8-ylidene)-hydrazino]-benzenesulfonamide (mixture of E and Z isomers).
Example 65: 4-[N'-(1-Chloro-7-oxo-6,7-dihydro-3H-pyrrolo[3,2-e]indazol-8-ylidene)-hydrazino]-benzenesulfonamide (Z isomer).
Example 66: 4-[N'-(1,7-Dioxo-2,3,6,7-tetrahydro-1H-2,6-diaza-as-indacen-8-ylidene)-hydrazino]-N-methyl-benzenesulfonamide (Z-isomer).
Example 67: N-(3-Hydroxy-2,2-dimethyl-propyl)-C-{4-[(7-oxo-6,7-dihydro-1-thia-3,6-diaza-as-indacen-8-ylidenemethyl)-amino]-phenyl}-methanesulfonamide (Z-isomer).
Example 68: N-Methyl-C-{4-[N'-(2-oxo-2,3-dihydro-pyrrolo[3,2-f]quinolin-1-ylidene)-hydrazino]-phenyl}-methanesulfonamide (Z-isomer).
Example 69: N-(1H-Indazol-6-yl)-4-[(7-oxo-6,7-dihydro-1-thia-3,6-diaza-as-indacen-8-ylidenemethyl)-amino]-benzenesulfonamide (Z-isomer).
Example 70: 4-[(7-Oxo-6,7-dihydro-1-thia-3,6-diaza-as-indacen-8-ylidenemethyl)-amino]-N-thiazol-2-yl-benzenesulfonamide (Z-isomer).
Example 71: N-(Amino-imino-methyl)-4-[(7-oxo-6,7-dihydro-1-thia-3,6-diaza-as-indacen-8-ylidenemethyl)-amino]-benzenesulfonamide (Z-isomer).
Example 72: 4-[(7-Oxo-6,7-dihydro-1-thia-3,6-diaza-as-indacen-8-ylidenemethyl)-amino]-N-pyridin-2-yl-benzenesulfonamide (Z-isomer).
Example 73: 8-[(2,2-Dioxo-1,3-dihydro-benzo[c]thiophen-5-ylamino-methylene)-6,8-dihydro-1-thia-3,6-diaza-as-indacen-7-one (Z-isomer).
Example 74: {4-[(7-Oxo-6,7-dihydro-1-thia-3,6-diaza-as-indacen-8-ylidenemethyl)-amino]-phenyl}-methanesulfonamide (Z-isomer).
Example 75: N-Allyl-C-{4-[(7-oxo-6,7-dihydro-1-thia-3,6-diaza-as-indacen-8-ylidenemethyl)-amino]-phenyl}-methanesulfonamide (Z-isomer).
Example 76: 8-(4-Methylsulfonylmethyl-phenylamino-methylene)-6,8-dihydro-1-thia-3,6-diaza-as-indacen-7-one (Z-isomer).
Example 77: N-(3-Hydroxy-2,2-dimethyl-propyl)-4-[(7-oxo-6,7-dihydro-1-thia-3,6-diaza-as-indacen-8-ylidenemethyl)-amino]-benzenesulfonamide (Z-isomer).
Example 78: 4-[(7-Oxo-6,7-dihydro-1-thia-3,6-diaza-as-indacen-8-ylidenemethyl)-amino]-N-(3-trifluoromethyl-phenyl)-benzenesulfonamide (Z-isomer).
Example 79: 4-[(7-Oxo-6,7-dihydro-1-thia-3,6-diaza-as-indacen-8-ylidenemethyl)-amino]-N-pyrimidin-2-yl-benzenesulfonamide (Z-isomer).
Example 80: N-(5-Methyl-[1,3,4]thiadiazol-2-yl)-4-(7-oxo-6,7-dihydro-1-thia-3,6-diaza-as-indacen-8-ylidenemethyl)-amino]-benzenesulfonamide (Z-isomer).
Example 81: N-Acetyl-4-[(7-oxo-6,7-dihydro-1-thia-3,6-diaza-as-indacen-8-ylidenemethyl)-amino]-benzenesulfonamide (Z-isomer).
Example 82: N-Benzoyl-4-[(7-oxo-6,7-dihydro-1-thia-3,6-diaza-as-indacen-8-ylidenemethyl)-amino]-benzenesulfonamide (Z-isomer).
Example 83: N-Methyl-4-[N'(7-oxo-6,7-dihydro-1-thia-3,6-diaza-as-indacen-8-ylidene)-hydrazino]-benzenesulfonamide (Z-isomer).
Example 84: N-[2-(2-Hydroxy-ethoxy)-ethyl]-N-methyl-4-[(7-oxo-6,7-dihydro-1-thia-3,6-diaza-as-indacen-8-ylidenemethyl)-amino]-benzenesulfonamide (Z-isomer).
Example 85: N-(2-{2-[2-(2-Methoxy-ethoxy)-ethoxy]-ethoxy}-ethyl)-4-[(7-oxo-6,7-dihydro-1-thia-3,6-diaza-as-indacen-8-ylidenemethyl)-amino]-benzenesulfonamide (Z-isomer).
Example 86: 4-[N'-(5,6-Dimethyl-2-oxo-1,2-dihydro-indol-3-ylidene)-hydrazino]-benzenesulfonamide (Z isomer).
Example 87: N-{6-Hydroxy-3-[(4-methylsulfamoylmethyl-phenyl)-hydrazono]-2-oxo-2,3-dihydro-1H-indol-5-yl}-acetamide (Z isomer).
Example 88: 4-[N'-(6-Chloro-5-methoxy-2-oxo-1,2-dihydro-indol-3-ylidene)-hydrazino]benzenesulfonamide (Z-isomer).
Example 89: 4-[N'-(5-Hydroxy-6-isopropyl-2-oxo-1,2-dihydro-indol-3-ylidene)-hydrazino]-benzenesulfonamide (Z-isomer).
Example 90: 4-[N'-(2-Methyl-6-oxo-5,6-dihydro-3-oxa-1,5-diaza-s-indacen-7-ylidene)-hydrazino]-benzenesulfonamide (Z isomer).
Example 91: 4-[N'-(5-Acetyl-2-oxo-2,5,6,7-tetrahydro-1H-pyrrolo[2,3-f]indol-3-ylidene)-hydrazino]-benzenesulfonamide (Z-isomer).
Example 92: 4-[N'-(6-Oxo-5,6-dihydro-[1,3]-dioxolo[4,5-f]indol-7-ylidene)-hydrazino]-benzenesulfonamide (Z-isomer).
Example 93: 4-[N'-(2-Oxo-2,5,6,7-tetrahydro-1H-pyrrolo[2,3-f]indol-3-ylidene)-hydrazino]-benzenesulfonamide hydrobromide (Z-isomer).
Example 94: C-{4-[N'-(4,6-Dichloro-5-methoxy-2-oxo-1,2-dihydro-indol-3-ylidene)-hydrazino]-phenyl}-N-methyl-methanesulfonamide (Z isomer).
Example 95: 4-[N'-(4-Chloro-5-hydroxy-6-methyl-2-oxo-1,2-dihydro-indol-3-ylidene)-hydrazino]-benzenesulfonamide (Z-isomer).
Example 96: 4-[N'-(5-Hydroxy-4,6-dimethyl-2-oxo-1,2-dihydro-indol-3-ylidene)-hydrazino]-benzenesulfonamide (Z-isomer).
Example 97: 3-(1H-Indazol-5-ylamino-methylene)-1,3-dihydro-indol-2-one (Z-isomer).
Example 98: 3-[(1H-Indazol-6-yl)-hydrazone]-1,3-dihydro-indol-2-one (Z-isomer).
Example 99: 4-[N'-(5-Hydroxy-4,6-dimethyl-2-oxo-1,2-dihydro-indol-3-ylidene[-hydrazino]-phenyl}-N-methyl-methanesulfonamide (Z isomer).

Example 100: N-Methyl-4-(5-oxazol-5-yl-2-oxo-1,2-dihydro-indol-3-ylidenemethyl)-amino]-phenylmethanesulfonamide (Z-isomer).

Example 101: 8-(3H-Benzotriazol-5-ylaminomethylene)-6,8-dihydro-1-thia-3,6-diaza-as-indacene-7-one (Z-isomer).

Example 102: 4-[N'-2-Oxo-2,3-dihydropyrrolo[3,2-f]quinolin-1-ylidene)hydrazino]-benzenesulfonamide (Z-isomer).

Example 103: 2-Oxo-3-(4-sulfamoyl-phenylamino-methylene)-2,3dihydro-1H-indole-5-carboxylic acid isobutyl ester (Z-isomer).

Example 104: 4-[(7-Oxo-6,7-dihydro-1-thia-3,6-diaza-as-indacen-8-ylidenemethyl)amino]-N-pyridinyl4-yl-methyl benzenesulfonamide (Z-isomer).

The invention discloses six different points of substitution on structural formula (I). Each of these points of substitution bears a substituent whose selection and synthesis as part of this invention was independent of all other points of substitution on formula (I). Thus, each point of substitution is now further described individually.

Preferred substitutions at the $R^1$ position include hydrogen, halogen, amide, nitro, lower alkyl, hydroxy, hydroxyalkyl, pyrimidineloweralkyl, loweralkoxycarbonyl, cyclic loweralkyl, hydroxyphenylloweralkyl, phenoxy, alkoxy, or pyrazole, or are fused with $R^2$ to form fused thiazole, pyrazole, triazole, halogen-substituted diazole, acyl substituted pyrrole, and pyridine, rings. Most preferred are hydrogen, methyl and fused with $R^2$ for form fused thiazole and fused pyridine. Most highly preferred are to be fused with $R^2$ to form fused thiazole.

Preferred substitutions at the $R^2$ position include hydrogen, halogen, sulfate, amine, quaternary amine, amide, ester, phenyl, alkoxy, aminosulfonyl, lower alkyl sulfonyl, furanyl lower alkyl amide, pyridinyl lower alkyl amide, alkoxy-substituted phenyl lower alkyl amide, morpholino lower alkyl amide, imidazolyl lower alkyl amide, hydroxy lower alkyl amide, alkoxy lower alkyl amide, lower alkyl amide, lower alkyl sulfonamide, lower alkyl hydroxy substituted amino, nitro, halogen-substituted phenoxycarbonyl, or triazole or oxazole rings, or are fused with $R^3$ to form a fused oxazole, pyrrole, or dioxolane ring, which fused rings can be substituted by lower alkyl, lower alkyl carbonyl, or, when said fused ring is a hetero ring having nitrogen as the heteroatom, forming a quaternary ammonium salt ionically bonded with a halogen atom. Most preferred are hydrogen, hydroxyl, oxazolyl, or fused with $R^1$ to form fused thiazolyl or fused pyridyl Most highly preferred are to be fused with $R^1$ to form fused thiazole.

Preferred substitutions at $R^3$ include hydrogen, lower alkyl, hydroxy lower alkyl, halogen, phenoxy, and alkoxy. Most preferred are hydrogen and methyl. Most highly preferred is hydrogen.

Preferred substitutions at $R^4$ include sulfonylamino, sulfonylaminoamino, lower alkyl sulfonylamino, lower alkylsulfonyl lower alkyl, alkoxysulfonylamino, phenylcarbonylsulfonylamino, phenoxysulfonyl, hydroxy lower alkylsulfonylamino, hydroxy lower alkylsulfonylamino lower alkyl, alkyl, phenylsulfonylamino, optionally substituted by halogen substituted lower alkyl, aminoiminosulfonylamino, alkylsulfonylaminoalkyl, pyridinyl lower alkyl sulfonylamino, benzamideazolesulfonylamino, pyridylsulfonylamino, pyrimidinylsulfonylamino, thiadiazolylsulfonylamino optionally substituted by lower alkyl, thiazolesulfonylamino, hydroxyalkoxyalkylsulfonylamino, or the group 4'-$SO_2NH[(CH_2)_2O]_4CH_3$, or are fused with $R^5$ to form a fused imidazole, triazole, cyclic sulfonylamino or thiaphene ring optionally disubstituted on the sulfur heteroatom by oxo. The most preferred substitutions are 2 pyridine sulfonylamino, 4 pyridine sulfonylamino, hydroxy n-butyl sulfonylamino, methylsulfonylaminomethylene, sulfonyldimethylamino, fused 1,2,3-triazole, and sulfonylamino. Most highly preferred is 2 pyridine sulfonylamino, 4 pyridine sulfonylamino and hydroxy n-butyl sulfonylamino.

The preferred substitution at $R^5$ is hydrogen.

Preferred substitutions at X include N, CH, and $CCH_3$. Most preferred is NH.

Preferred individual compounds of the present invention include any one of the following compounds:

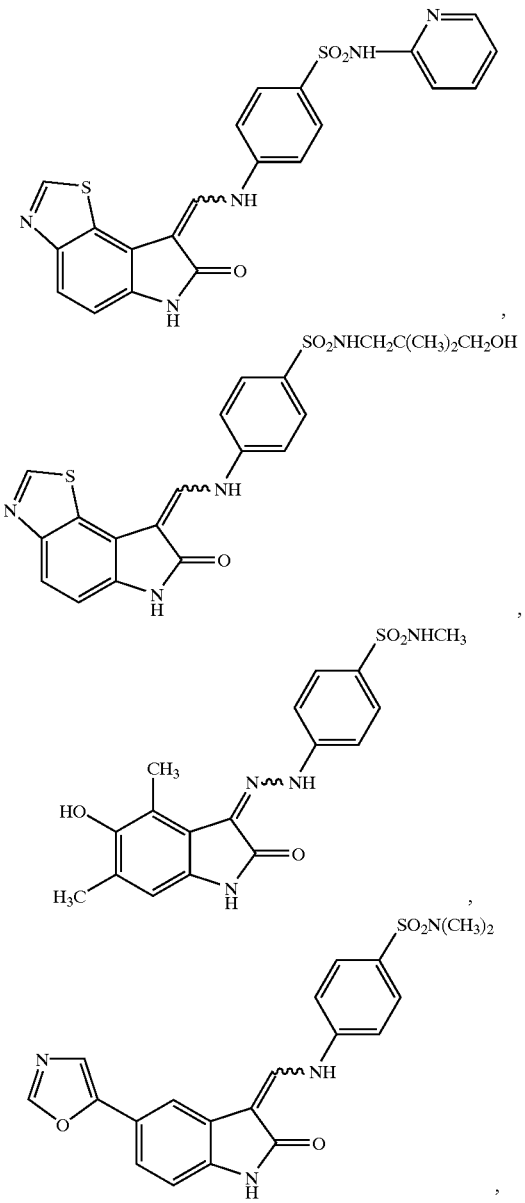

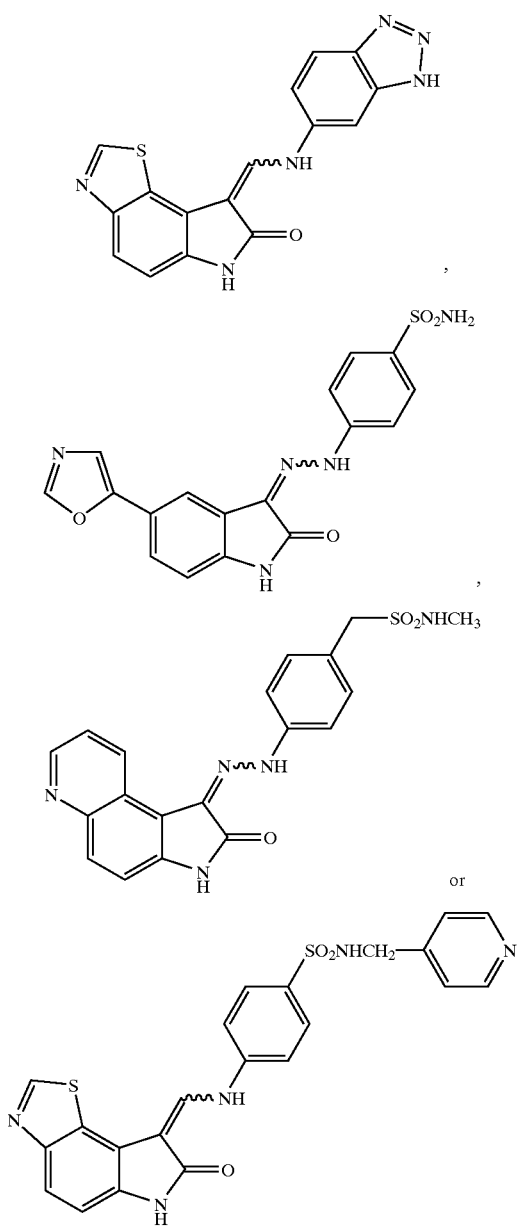

Highly preferred compounds include

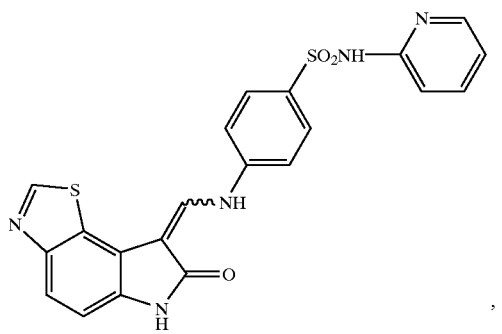

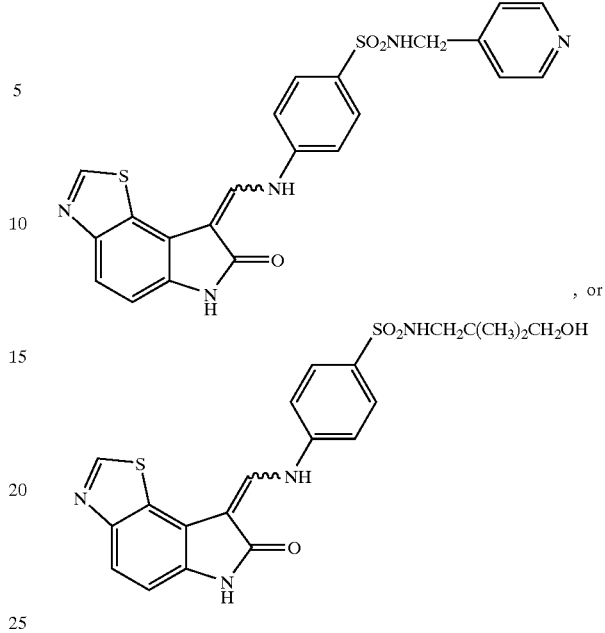

DETAILED DESCRIPTION OF THE INVENTION

Salts encompassed within the term "pharmaceutically acceptable salts" refer to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Diethanolamine, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Metaphosphoric, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Trifluoroacetate, Triethiodide, Trimethylammonium and Valerate.

Other salts which are not pharmaceutically acceptable may be useful in the preparation of compounds of formula (I) and these form a further aspect of the invention.

Also included within the scope of the invention are the individual isomers of the compounds represented by formula (I) above as well as any wholly or partially equilibrated mixtures thereof. The present invention also covers the individual isomers of the compounds represented by formula above as mixtures with isomers thereof in which one or more chiral asymmetric centers are inverted.

As used herein, the term "aliphatic" refers to the terms alkyl, alkylene, alkenyl, alkenylene, alkynyl, and alkynylene.

As used herein, the term "lower" refers to a group having between one and six carbons.

As used herein, the term "alkyl" refers to a straight or branched chain hydrocarbon-having from one to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkyl" as used herein include, but are not limited to, n-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkenylene" refers to an straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkynylene" refers to a straight or branched chain divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkynylene" as used herein include, but are not limited to, ethyne-1,2-diyl, propyne-1,3-diyl, and the like.

As used herein, the term "cycloaliphatic" refers to the terms cycloalkyl, cycloalkylene, cycloalkenyl, cycloalkenylene, cycloalkynyl and cycloalkyinylene.

As used herein, "cycloalkyl" refers to a alicyclic hydrocarbon group with one or more degrees of unsaturation, having from three to twelve carton atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cydopentyl-1,3-diyl, cyclohexyl-1,4-diyl, cycloheptyl-1,4-diyl, or cyclooctyl-1,5-diyl, and the like.

As used herein, the term "cycloalkenyl" refers to a substituted alicyclic hydrocarbon radical having from three to twelve carbon atoms and at least one carbon-carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 1-cyclopentene-3-yl, 1-cyclohexene-3-yl, 1-cycloheptene4-yl, and the like.

As used herein, the term "cycloalkenylene" refers to a substituted alicyclic divalent hydrocarbon radical having from three to twelve carbon atoms and at least one carbon-carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 4,5-cyclopentene-1,3-diyl, 3,4-cyclohexene-1,1-diyl, and the like.

As used herein, the term "heteroatom ring system" refers to the terms heterocyclic, heterocyclyl, heteroaryl, and heteroarylene. Non-limiting examples of such heteroatom ring systems are recited in the Summary of the Invention, above.

As used herein, the term "heterocyclic" or the term "heterocyclyl" refers to a three to twelve-membered heterocyclic ring having one or more degrees of unsaturation containing one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "heterocyclylene" refers to a three to twelve-membered heterocyclic ring diradical having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" refers to a benzene ring or to an optionally substituted benzene ring system fused to one or more optionally substituted benzene rings to form anthracene, phenanthrene, or napthalene ring systems, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of aryl include, but are not limited to, phenyl, 2-naphthyl, 1-naphthyl, biphenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of "arylene" include, but are not limited to, benzene-1,4-diyl, naphthalene-1,8-diyl, anthracene-1,4-diyl, and the like.

As used herein, the term "heteroary" refers to a five- to seven-membered aromatic ring, or to a polycyclic heterocyclic aromatic ring, containing one or more nitrogen, oxygen, or sulfur heteroatoms at any position, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" refers to the group $R_aO$—, where $R_a$ is aliphatic.

As used herein, the term "alkylsulfanyl" refers to the group $R_aS$—, where $R_a$ is aliphatic.

As used herein, the term "alkylsulfenyl" refers to the group $R_aS(O)$—, where $R_a$ is aliphatic.

As used herein, the term "alalkylsulfonyl" refers to the group $R_aSO_2$—, where $R_a$ is aliphatic.

As used herein, the term "acyl" refers to the group $R_aC(O)$—, where $R_a$ is aliphatic, cycloaliphatic, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is aliphatic.

As used herein, the term "acyloxy" refers to the group $R_aC(O)O$—, where $R_a$ is aliphatic, cycloaliphatic, or heterocyclyl.

As used herein, the term "aroyloxy" refers to the group $R_aC(O)O—$, where $R_a$ is aryl.

As used herein, the term "heteroaroyloxy" refers to the group $R_aC(O)O—$, where $R_a$ is heteroaryl.

As used herein, the term "optionally" means that the subsequently described event(s) may or may not occur, and includes both conditions.

As used herein, the term "substituted" refers to substitution with the named substituent or substituents, multiple degrees of substitution being allowed.

As used herein, the terms "contain" or "containing" can refer to in-line substitutions at any position along the above-defined alkyl, alkenyl, alkynyl or cycloalkyl substituents with one or more of any of O, S, SO, $SO_2$, N, or N-alkyl, including, for example, $—CH_2—O—CH_2—$, $—CH_2—SO_2—CH_2—$, $—CH_2—NH—CH_3$ and so forth.

As used herein, the term "solvate" is a complex of variable stoichiometry formed by a solute (in this invention, a compound of formula (I)) and a solvent. Such solvents for the purpose of the invention may not interfere with the biological activity of the solute. Solvents may be, by way of example, water, ethanol, or acetic acid.

As used herein, the terms "biohydrolyzable carbonate", "biohydrolyzable ureide" and "biohydrolyzable carbamate" is a carbonate, ureide, or carbamate, respectively of a drug substance (in this invention, a compound of general formula (I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable carbamate is orally absorbed from the gut and is transformed to (I) in plasma. Many examples of such are known in the art and include by way of, example lower alkyl carbamates.

As used herein, the term "biohydrolyzable ester" is an ester of a drug substance (in this invention, a compound of general formula (I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters, lower acyloxy-alkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides, biohydrolyzable esters and biohydrolyzable carbamates and also encompasses a) compounds in which the biohydrolyzable functionality in such a prodrug is encompassed in the compound of formula (I): for example, a lactam formed by a carboxylic group in $R_1$ and an amine in $R_2$, and compounds which may be oxidized or reduced biologically at a given functional group to yield drug substances of formula (I). Examples of these functional groups are, but are not limited to, 1,4-dihydropyridine, N-alkylcarbonyl-1,4-dihydropyridine, 1,4-cyclohexadiene, tert-butyl, and the like.

As used herein, the term "affinity reagent" is a group attached to the compound of formula (I) which does not affect its in vitro biological activity, allowing the compound to bind to a target, yet such a group binds strongly to a third component allowing a) characterization of the target as to localization within a cell or other organism component, perhaps by visualization by fluorescence or radiography, or b) facile separation of the target from an unknown mixture of targets, whether proteinaceous or not proteinaceous. An example of an affinity reagent according to b) would be biotin either directly attached to (I) or linked with a spacer of one to 50 atoms selected from the group consisting of C, H, O, N, S, or P in any combination. An example of an affinity reagent according to a) above would be fluorescein, either directly attached to (I) or linked with a spacer of one to 50 atoms selected from the group consisting of C, H, O, N, S, or P in any combination.

The term "pharmacologically effective amount" shall mean that amount of a drug or pharmaceutical agent that will elicit the biological or medical response of a tissue, system, animal or human that is being sought by a researcher or clinician.

Whenever the terms "aliphatic" or "aryl" or either of their prefixes appear in a name of a substituent (e.g. arylalkoxyaryloxy) they shall be interpreted as including those limitations given above for "aliphatic" and "aryl". Aliphatic or cycloalkyl substituents shall be recognized as being term equivalents to those having one or more degrees of unsaturation. Designated numbers of carbon atoms (e.g. $C_{1-10}$) shall refer independently to the number of carbon atoms in an aliphatic or cyclic aliphatic moiety or to the aliphatic portion of a larger substituent in which the term "aliphatic" appears as a prefix (e.g. "al-").

As used herein, the term "disubstituted amine" or "disubstituted amino-" shall be interpreted to include either one or two substitutions on that particular nitrogen atom.

As used herein, the term "oxo" shall refer to the substituent $=O$.

As used herein, the term "halogen" or "halo" shall include iodine, bromine, chlorine and fluorine.

As used herein, the term "mercapto" shall refer to the substituent $—SH$.

As used herein, the term "carboxy" shall refer to the substituent $—COOH$.

As used herein, the term "cyano" shall refer to the substituent $—CN$.

As used herein, the term "aminosulfonyl" shall refer to the substituent $—SO_2NH_2$.

As used herein, the term "carbamoyl" shall refer to the substituent $—C(O)NH_2$.

As used herein, the term "sulfanyl" shall refer to the substituent $—S—$.

As used herein, the term "sulfenyl" shall refer to the substituent $—S(O)—$.

As used herein, the term "sulfonyl" shall refer to the substituent $—S(O)_2—$.

The compounds of formula (I) can be prepared readily according to the following reaction General Synthesis Scheme (in which all variables are as defined before) and Examples or modifications thereof using readily available starting materials, reagents and conventional synthesis procedures. In these reactions, it is also possible to make use of variants which are themselves known to those of ordinary skill in this art, but are not mentioned in greater detail.

General Synthesis Scheme

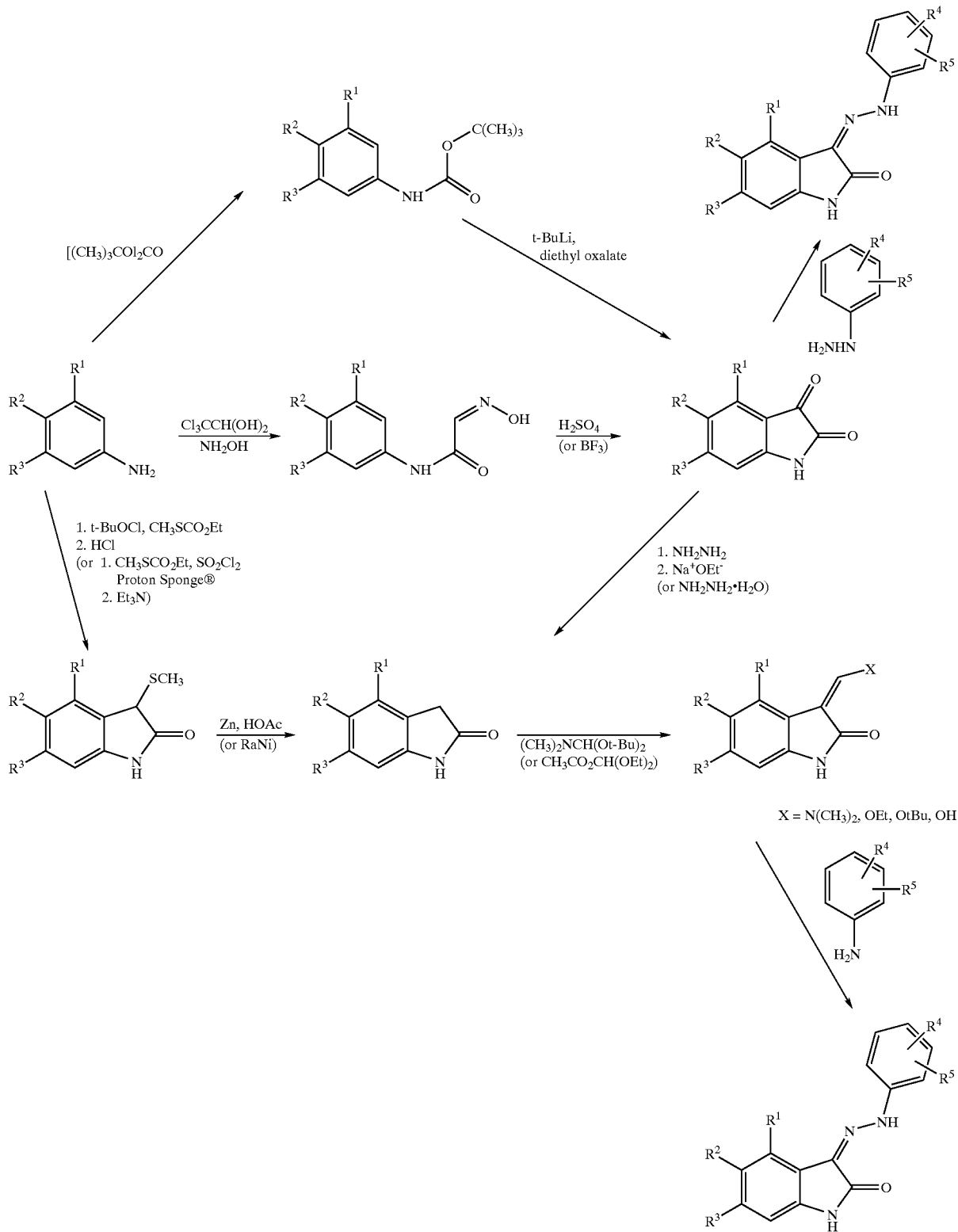

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the Examples are as follows:

| | |
|---|---|
| g | =grams |
| mg | =milligrams |
| L | =liters |
| mL | =milliliters |
| M | =molar |
| N | =normal |
| mM | =millimolar |
| i.v. | =intravenous |
| p.o. | =per oral |
| s.c. | =subcutaneous |
| Hz | =hertz |
| mol | =moles |
| mmol | =millimoles |
| mbar | =millibar |
| psi | =pounds per square inch |
| rt | =room temperature |
| min | =minutes |
| h | =hours |
| mp | =melting point |
| TLC | =thin layer chromatography |
| $R_f$ | =relative TLC mobility |
| MS | =mass spectrometry |
| NMR | =nuclear magnetic resonance spectroscopy |
| APCI | =atmospheric pressure chemical ionization |
| ESI | =electrospray ionization |
| m/z | =mass to charge ratio |
| $t_r$ | =retention time |
| Pd/C | =palladium on activated carbon |
| ether | =diethyl ether |
| MeOH | =methanol |
| EtOAc | =ethyl acetate |
| TEA | =triethylamine |
| DIEA | =diisopropylethylamine |
| THF | =tetrahydrofuran |
| DMF | =N,N-dimethylformamide |
| DMSO | =dimethylsulfoxide |
| DDQ | =2,3-dichloro-5,6-dicyano-1,4-benzoquinone |
| LAH | =lithium aluminum hydride |
| TFA | =trifluoroacetic acid |
| LDA | =lithium diisopropylamide |
| THP | =tetrahydropyranyl |
| NMM | =N-methylmorpholine, 4-methylmorpholine |
| HMPA | =hexamethylphosphoric triamide |
| DMPU | =1,3-dimethypropylene urea |
| d | =days |
| ppm | =parts per million |
| kD | =kiloDalton |
| LPS | =lipopolysaccharide |
| PMA | =phorbol myristate acetate |
| SPA | =scintillation proximity assay |
| EDTA | =ethylenediamine tetraacetic acid |
| FBS | =fetal bovine serum |
| PBS | =phosphate buffered saline solution |
| BrdU | =bromodeoxyuridine |
| BSA | =bovine serum albumin |
| FCS | =fetal calf serum |
| DMEM | =Dulbecco's modified Eagle's medium |
| pfu | =plaque forming units |
| MOI | =multiplicity of infection |

Reagents are commercially available or are prepared according to procedures in the literature. The physical data given for the compounds exemplified is consistent with the assigned structure of those compounds. $^1$H NMR spectra were obtained on VARIAN Unity Plus NMR spectrophotometers at 300 or 400 Mhz. Mass spectra were obtained on Micromass Platform II mass spectrometers from Micromass Ltd. Altrincham, UK, using either Atmospheric Chemical Ionization (APCI) or Electrospray Ionization (ESI). Analytical thin layer chromatography (TLC) was used to verify the purity of some intermediates which could not be isolated or which were too unstable for full characterisation, and to follow the progess of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure.

Procedure A

First Method for 1H-indol-2,3-dione (isatin) Formation: Preparation of 6-H-1-thia-3,6-diaza-as-indacen-7,8-dione To a 1-L flask was added a magnetic stir bar, 85 g of sodium sulfate, and 100 mL of water. The mixture was magnetically stirred until all the solids were dissolved. To the resultant aqueous solution was added a solution of 6-aminobenzothiazole (4.96 g, 33.0 mmol) in 50 mL of 1N aqueous hydrochloric acid and 10 mL of ethanol. The mixture was stirred, and chloral (6.0 g, (36 mmol) was added. To the resultant solution was added a solution of hydroxyl amine hydrochloride (7.50 g, 108 mmol) in 30 mL of water. The final mixture was heated with stirring to a gentle boil until all solids dissappeared, and heating was continued for an additional 15 min. The flask was removed from the heat, and the solution was poured onto 500 g of ice. The mixture was stirred as the product precipatated from solution. The precipatate was collected by suction filtration, washed thoroughly with water, filtered, and air dried to provide 6.9 g (94%) of N-benzothiazol-6-yl-2-hydroxyimino-acetamide: $^1$H NMR (DMSO-$d_6$): δ 12.2 (s, 1H), 10.4 (s, 1H), 9.2 (s, 1H), 8.5 (s, 1H), 7.9 (d, 1H), 7.7 (m, 1H), 7.7 (s, 1H); APCI–MS m/z 220 (M–H)$^-$. To a 1-L 3-neck round bottom flask was placed a magnetic stir bar and 100 ml of concentrated sulfuric acid. The flask was fitted with a thermometer to monitor the temperature of the reaction. The sulfuric acid was heated to 100° C., and 10.0 g (45.2 mmol) of N-benzothiazol-6-yl-2-hydroxyimino-acetamide was added slowly. The solution was heated for ~1 h, and the reaction mixture was poured into 750 g of ice and water. The residual reaction mixture in the reaction vessel was washed out with an additional 20 mL of cold water. The aqueous slurry was stirred for about 1 h and filtered. The solid was washed thoroughly with water, filtered, and air dried to yield 4.3 g (46%) of 6-H-1-thia-3,6-diaza-as-indacen-7,8-dione: $^1$H NMR (DMSO-$d_6$): δ 11.1 (s, 1H), 9.2 (s, 1H), 8.2 (d, 1H), 7.0 (d, 1H); APCI–MS m/z 203 (M–H)$^-$.

Procedure B

Second Method for 1H-indol-2,3-dione (isatin) Formation: Preparation of 6-phenoxy-1H-indole-2, 3-dione To a stirred solution of 1.0 g (6.0 mmol) of chloral hydrate in 25 mL of water was added 7.0 g (22 mmol) of sodium sulfate decahydrate, followed by a solution of 1.18 g (17.0 mmol) of hydroxylamine hydrochloride in 10 mL of water. A solution of 1.0 g (5.4 mmol) of 3-phenoxyaniline in 10 mL of 1.0 N HCl was then added with stirring. The resulting suspension was warmed, and 40 mL of 95% EtOH was added to dissolve the suspension. The solution was refluxed for 0.75 h and then cooled to ambient temperature. The resulting solid was collected by vacuum filtration and air dried to afford 0.95 g (67%) of 2-hydroxyimino-N-(3-phenoxyphenyl)acetamide as a solid: $^1$H NMR (DMSO-d$_6$): δ 6.42 (d, J=8.4 Hz, 1H), 7.06 (d, J=7.9 Hz, 2H), 7.18 (t, J=7.3 Hz, 1H), 7.25–7.50 (m, 5H), 7.64 (s, 1H), 10.29 (s, 1H), 12.21 (s, 1H); APCI–MS: m/z 255 (M–H)$^-$. A suspension of 0.15 g (0.58 mmol) of 2-hydroxyimino-N-(3-phenoxyphenyl)acetamide in 0.4 mL of BF$_3$ etherate was heated to 85° C. for 0.75 h. The mixture was cooled to rt and 10 g of crushed ice was added. The resulting solid was collected by vacuum filtration and subjected to flash chromatography on silica gel (hexane/EtOAc 1.5:1) to afford 6-phenoxy-1H-indole-2,3-dione as a solid (0.018 g, 13%): $^1$H NMR (DMSO-d$_6$): δ 6.44 (d, J=2.0 Hz, 1H), 6.56 (dd, J=2.0, 8.4 Hz, 1H), 7.08 (d, J=8.2 Hz, 1H), 7.22–7.29 (m, 1H), 7.38–7.46 (m, 2H), 7.52 (d, J=8.4 Hz, 1H), 9.05 (s, 1H); APCI–MS: m/z 255 (M+Na)$^+$.

Procedure C

Third Method for 1H-indol-2,3-dione (isatin) Formation (Hewawasam and Meanwell, Tetrahedron Letters 1994, 35, 7303–6): Preparation of 4-isopropoxy-1H-indol-2,3-dione and Conversion to 4-[N'-(4-isopropoxy-2-oxo-1,2-dihydro-indol-3-ylidene)-hydrazino]-benzenesulfonamide Example 17

4-[N'-(4-Isopropoxy-2-oxo-1,2-dihydro-indol-3-ylidene)-hydrazino]-benzenesulfonamide A solution of 3.78 g (25.0 mmol) of 3-isopropoxy aniline and di-tert-butyl dicarbonate in 25 mL of THF was heated to reflux for 2 h. The solution was cooled to ambient temperature, and solvent was removed in vacuo. The residue was dissolved in 100 mL of EtOAc, and the solution was washed with three 50-mL portions of 0.5 M citric acid and 50 mL of brine. The solution was dried over MgSO$_4$ and removal of solvent in vacuo afforded N-(t-butyloxycarbonyl)-3-isopropoxyaniline as a white solid (5.75 9, 92%): mp 79–81° C.; $^1$H NMR (DMSO-d$_6$): δ 1.21 (d, J=6.0 Hz, 6H), 1.43 (s, 9H), 4.46 (septet, J=6 Hz, 1H), 6.47 (dd, J=2.1, 8.1 Hz, 1H), 6.94 (d, J=8.1 Hz, 1H), 7.0–7.1 (m, 2H), 9.23 (s, 1H); APCI–MS: m/z 274 (M+Na)$^+$. To a solution of 2.5 g (10 mmol) of N-(t-butyloxycarbonyl)-3-isopropoxyaniline in 15 mL of dry THF at –78° C. was added 15 mL (25 mmol) of 1.7 M t-butyllithium in hexanes. The mixture was stirred at –20° C. for 2 h. A solution of 1.84 g (12.5 mmol) of diethyl oxalate in 10 mL of dry THF was added slowly over 5 min, and the mixture was stirred at –20° C. for 2 h. The reaction mixture was then poured into 100 mL of 1.0 N HCl and extracted with two 100-mL portions of EtOAc. Solvent was removed in vacuo, and the residue was dissolved in 100 mL of a 1:1 mixture of EtOH and 6 N HCl and heated to reflux for 1 h. The mixture was cooled to ambient temperature and was extracted with four 100-mL portions of EtOAc. The combined extracts were evaporated to dryness to provide crude 4-isopropoxy-1H-indol-2,3-dione, which was dissolved in 10 mL of EtOH containing 0.50 g (2.2 mmol) of 4-sulfonamidophenylhydrazine hydrochloride. The solution was heated to 80° C. for 1 h and cooled to ambient temperature. The resulting solid was collected by vacuum filtration and purified by flash chromatography on silica gel (EtOAc/hexane 3:2) to afford the title compound as a yellow solid (0.052 g, 1.4%): mp >250° C.; $^1$H NMR (DMSO-d$_6$): δ 3.35 (d, J=6 Hz, 6H), 4.74 (septet, J=6 Hz, 1H), 6.48 (d, J=7.7 Hz, 1H), 6.69 (d, J=8 Hz, 1H), 7.14–7.2 (m, 3H), 7.47 (d, J=8.7 Hz, 2H), 7.75 (d, J=8.7 Hz, 2H), 11.01 (s, 1H), 12.79 (s, 1H); APCI–MS: m/z 373 (M–H)$^-$. Anal. Calcd for C$_{17}$H$_{18}$N$_4$O$_4$S: C, 54.53; H, 4.85; N, 14.96; S, 8.56. Found: C, 54.46; H, 4.84; N, 14.90; S, 8.50.

Procedure D

First Method for 1,3-dihydro-indol-2-one (oxindole) Formation Gassman and van Bergen, Journal of the American Chemical Society 1974, 96, 5508–12): Preparation of 6.8-dihydro-1-thia-3,6-diaza-as-indacen-7-one A 2-L three-neck round bottom flask was fitted with an internal thermometer, 250-mL addition funnel, magnetic stir bar and septa. The flask was charged with nitrogen, 200 mL of dry THF, and 6-aminobenzothiazole (15.2 g, 0.100 mol). The mixture was stirred and cooled in a dry ice-acetone bath to an internal temperature of –74° C. A solution of tert-butyl hypoclorite (11.0 g, 0.103 mol) in 50 mL of dichloromethane was added over a 15 min period. The resultant solution was stirred for an additional 3 h at dry ice-acetone bath temperature. To the reaction was then added by slow, dropwise addition a solution of ethyl methylthioacetate (13.8 g, 0.103 mol) in 50 mL of dichoromethane. The resultant solution was stirred for an additional 3 h at dry ice-acetone bath temperature. A solution of triethyl amine (25.3 g, 0.250 mol) and 50 ml of dichloromethane was added at dry ice-acetone bath temperature, and the solution was stirred for 0.5 h. The cooling bath was removed, and the reaction was allowed to warm to rt. The reaction was then concentrated to a thick residue. The thick oil was resuspended in 200 mL of ether and 600 mL of 0.25 M hydrochloric acid. The mixture was allowed to stir for 24 h. The resulting solid was filtered from the mixture and triturated with water and ether. The solid was then resuspended in cold MeOH, filtered and dried under vacuum for 16 h to yield 18.7 g (79%) of 8-methylsulfanyl-6,8-dihydro-1-thia-3,6-diaza-as-indacen-7-one: $^1$H NMR (DMSO-d$_6$) δ 10.8 (s, 1H), 9.2 (s, 1H), 8.0 (d, 1H), 7.1 (d, 1H), 1.8 (s, 3H); APCI–MS m/z 235 (M–H)$^-$. To a 500-mL erlenmeyer flask was added a stir bar, 8.1 g (0.034 moles) of 8-methylsulfanyl-6,8-dihydro-1-thio-3,6-diaza-as-indacen-7-one and 100 mL of glacial acetic acid. The mixture was stirred until all the starting material had dissolved. The reaction mixture was then diluted with 100 mL of THF. Zinc metal (16 g, 325 mesh) was then added. The heterogeneous mixture was then stirred and heated to 60° C. for 2.5 h. The mixture was vacuum filtered through a one half inch pad of celite. The residue on the filter pad was washed with additional THF. The filtrates were combined and concentrated to a wet solid. The solid was triturated with MeOH, filtered and air dried to yield 4.51 g (70%) of 6,8-dihydro-1-thia-3,6-diaza-as-indacen-7-one as a free-flowing solid: $^1$H NMR (DMSO-d$_6$): δ 10.5 (s, 1H), 9.1 (s, 1H), 7.9 (d, 1H), 7.0 (d, 1H), 3.6 (s, 2H); APCI–MS m/z 191 (M+H)$^+$.

Procedure E

Second Method for 1,3-dihydro-indol-2-one (oxindole) Formation (Johnson and Aristoff, Journal of Organic Chemistry 1990, 55, 1374–5): Preparation of 2-oxo-2,3-dihydro-1H-indole-5-carboxylic acid methyl ester and conversion to 2-oxo-3-4-sulfamoyl-phenylamino-methylene)-2,3-dihydro-1H-indole-5-carboxylic acid methyl ester (Z-isomer)

Example 27

2-Oxo-3(4-sulfamoyl-phenylamino-methylene)-2,3-dihydro-1H-indole-5-carboxylic acid methyl ester (Z-isomer)

A solution of 2.66 g (20.0 mmol) of ethyl (methylthio) acetate dissolved in 200 mL of dichloromethane was cooled with stirring to −70° C. and 2.7 g (20.0 mmol) of sulfuryl chloride was added. The reaction was stirred for 30 min. at −70° C., and a solution of 3.0 g (20 mol) of methyl 4-aminobenzoate and 4.39 (20 mmol) of Proton Sponge® in 250 mL of dichloromethane was added dropwise over 1 h. The resulting pink slurry was treated with 2.3 g (23 mmol) of TEA in one portion, and the solution was allowed to warm to rt. The solution was washed with three 250-mL portions of water, dried over $MgSO_4$, and concentrated to give an oil. This was chromatographed on silica gel eluting with hexane:EtOAc (1:1) to yield 2.0 g (42% yield) of 3-methylthio-2-oxo-2,3-dihydro-1H-indole-5-carboxylic acid methyl ester: $^1$H NMR (DMSO-$d_6$): δ 1.97 (s, 3H), 3.35 (s, 3H), 4.67 (s, 1H), 6.97 (d, J=8.2 Hz, 1H), 7.84 (s, 1H). 7.91 (d, J=8.2 Hz, 1H), 10.97 (s, 1H). A solution of 2.0 g (8.4 mmol) of 3-methylthio-2-oxo-2,3-dihydro-1H-indole-5-carboxylic acid methyl ester in 20 mL of acetic acid was treated with 10 g of zinc powder. The reaction mixture was stirred for 2 h at rt, filtered through celite and concentrated to dryness. The residue was chromatographed on silica gel eluting with hexane:EtOAc (1:1) to yield 1.6 g (99% yield) of 2oxo-2,3-dihydro-1H-indole-5-carboxylic acid methyl ester as a pink solid: $^1$H NMR (DMSO-$d_6$): δ 3.52 (s, 2H), 3.77 (s, 3H), 6.87 (d, J=8.2 Hz, 1H), 7.74 (s, J=1H), 7.80 (d, J=8.2 Hz, 1H), 10.72 (br s, 1H). Conversion to the 3-dimethylaminomethylene-2-oxo-2,3-dihydro-1H-indole-5-carboxylic acid methyl ester (mixture of E and Z isomers) was carried out via Procedure G in 49% yield: $^1$H NMR (DMSO-$d_6$): δ 3.29 Z (s, 6H), 3.31 E (s, 6H), 3.76 Z (s, 3H), 3.76 E (s, 3H), 6.74 Z (d, J=8.1 Hz, 1H), 6.81 E (d. J=8.2 Hz, 1H), 7.47–7.50 Z (m, 1H), 7.50–7.52 E (m, 1H), 7.57 E (dd, J=1.3, 8.2 Hz, 1H), 7.74 Z (s, 1H), 7.89 Z (s, 1H), 7.94 E (s, 1H), 10.33 Z (bs, 1H), 10.43 E (bs, 1H). The title compound was prepared in 41% yield from 3-[(dimethylamino) methylene]oxindole-5-carboxylic acid methyl ester and 4-aminobenzenesulfonamide according to Procedure J: $^1$H NMR (DMSO-$d_6$): δ 3.81 (s, 3H), 6.92 (d, J=8.2 Hz, 1H), 7.26 (s, 2H), 7.60 (d, J=8.4 Hz, 2H), 7.69 (d, J=8.2 Hz, 1H). 7.75 (d, J=8.4 Hz, 2H), 8.29 (s, 1H), 8.86 (d, J=12.4 Hz, 1H), 10.80 (d, J=12.4 Hz, 1H), 10.94 (s, 1H); APCI–MS m/z 372 (M−1)$^-$. Anal. Calcd for $C_{17}H_{15}N_3O_5S$: C, 54.68, H, 4.05; N, 11.25; S, 8.59. Found C, 54.65, H, 4.12; N, 11.17; S. 8.49.

Procedure F

Third Method for 1,3-dihydro-indol-2-one (oxindole) Formation (Seibert, Chemie Berichte 1947, 80, 494–502): Preparation of 3-H-pyrrolo[3,2-f]quinoline-2-one A solution of 2.3 g (12 mmol) of 3-H-pyrrolo[3,2-f] quinoline-1,2-dione and 2.0 ml (0.06 mol) of hydrazine in 50 ml of DMF and 50 ml of ethanol was stirred at reflux for 2 h. The resulting suspension was allowed to cool to ambient temperature and was then chilled in an ice bath and filtered. The solid was washed with a small volume of ethanol and allowed to air dry to give 1-hydrazono-1,3-dihydropyrrolo [3,2-f]quinolin-2-one as an orange solid (1.8 g, 73%): $^1$H NMR (DMSO-$d_6$): δ 7.37 (d, J=8.8 Hz, 1H), 7.47 (dd, J=8.4, 4.2 Hz, 1H), 7.81 (d, J=8.8 Hz, 1H), 8.71 (dd, J=4.2, 1.6 Hz, 1H), 8.80 (d, J=8.4 Hz, 1H), 9.90 (br d, J=14.7 Hz, 1H), 10.89 (br d, J=14.7 Hz, 1H), 10.95 (br s, 1H); ESI–MS m/z 213 (M+H)$^+$. A solution 1.8 g (8.5 mmol) of 1-hydrazono-1,3-dihydropyrrolo[3,2-f]quinolin-2-one in 50 ml of freshly prepared 0.5 M sodium ethoxide solution was stirred at reflux for 3 h. The solution was diluted with 50 ml of water, neutralized with acetic acid, and concentrated on a rotary evaporator until cloudy. The solution was stored in a refrigerator overnight. The solid was filtered off, and the filtrate was extracted with three 80-ml portions of EtOAc. A solution of the solid in MeOH/EtOAc was combined with the extracts. and passed through a short pad of silica gel, eluting with EtOAc. The solution was then concentrated to a small volume on a rotary evaporator, and the resulting suspension was diluted with an equal volume of ethanol, sonicated, and filtered to give 3-H-pyrrolo[3,2-f]quinoline-2-one as a light green solid (0.52 g, 33%); $^1$H NMR (DMSO-$d_6$): δ 3.80 (s, 2H), 7.35 (d, J=8.8 Hz, 1H), 7.44 (dd, J=8.4, 4.2 Hz, 1H), 7.88 (d, J=8.8 Hz, 1H), 8.08 (d, J=8.4 Hz, 1H), 8.70 (dd, J=4.2, 1.6 Hz, 1H), 10.57 (br s, 1H); APCI–MS m/z 183 (M−H)$^-$.

Procedure G

Method for isatin hydrazone Formation: Preparation of C-{4-[N'-(5-hydroxy-4,6dimethyl-2-oxo-1,2-dihydroindol(3-ylidene)hydrazino]phenyl}-N-methylmethanesulfonamide

Example 99

C-{4-[N'-(5-hydroxy-4,6-dimethyl-2-oxo-1,2-dihydroindol(3-ylidene)hydrazino]phenyl}-N-methylmethanesulfonamide 4,6-Dimethyl-5-hydroxy-1H-indol-2,3-dione was prepared from 3,5-dimethyl-4-hydroxyaniline according to Procedure A: $^1$H NMR (DMSO-$d_6$): δ 2.17 (s, 3H), 2.30 (s, 3H), 6.45 (s, 1H), 8.29 (s, 1H), 10.65 (s, 1H); ESI–MS m/z 190 (M−H)$^-$. A mixture of 100 mg (0.52 mmol) of 4,6-dimethyl-5-hydroxy-1H-indol-2,3dione and 144 mg (0.57 mmol) of C-(4-hydrazinophenyl)-N-methylmethanesulfonamide hydrochloride in 5 ml of EtOH was heated to 80° C. for 1 h. Upon cooling 10 ml of $H_2O$ was added and the solid was collected by vacuum filtration and dried in a vacuum oven at 60° C. to afford the title compound as a yellow solid (79 mg, 79%); mp 252–255° C.; $^1$H NMR (DMSO-$d_6$): δ 2.16 (s, 3H), 2.44 (s, 3H) 2.52 (d, J=4.9 Hz, 3H), 4.25 (s, 2H), 6.47 (s, 1H), 6.84 (q, J=4.9 Hz, 1H), 7.28–7.34 (m, 4H), 7.92 (s, 1H), 10.69 (s, 1H), 12.87 (s, 1H); APCI–MS m/z 411 (M+Na)$^+$. Anal. Calcd for $C_{18}H_{20}N_4O_4S$: C, 55.66; H, 5.19; N, 14.42, S, 8.25. Found: C, 55.56; H. 5.21; N, 14.25; S, 8.08.

Procedure H

Method for dimethylaminomethinyloxindole Formation: Preparation of 8dimethylamino-methylene-6,8-dihydro-1-thia-3,6-diaza-as-indacen-7-one To a suspension of 1.0 g (5.3 mmol) of 6,8-dihydro-1-thia-3,6-diaza-as-indacen-7-one in 7.5 mL of DMF was added 1.38 g (6.80 mmol) of N,N-dimethylformamide-di-t-butyl acetal. The mixture was stirred at ambient temperature for 1 h and diluted with 7.5 mL of Et$_2$O. The resulting precipitate was isolated filtration to afford 8dimethylamino-methylene-6,8dihydro-1-thia-3,6-diaza-as-indacen-7-one as a tan solid (1.0 g, 77%): $^1$H NMR (DMSO-d$_6$): δ 3.33 (bs, 3H), 3.59 (bs, 3H), 6.97 (d, J=8.4, 1H), 7.33 (s, 1H), 7.62 (d, J=8.4, 1H), 9.13 (s,1H), 10.29 (s, 1H); APCI–MS: m/z246 (M+H)$^+$.

Procedure I

Method for ethoxymethinytoxindole Formation: Preparation of 8-ethoxymethylene-6,8dihydro-1-thia-3,6-diaza-as-indacen-7-one.

To a 250-ml round bottom flask was added a stir bar, 6,8-dihydro-1-thia-3,6-diaza-as-indacen-7-one (4.0 g, 0.021 mol), 40 mL of glacial acetic and diethoxymethyl acetate (17.0 g, 0.105 moles). The flask was fitted with a reflux condenser and charged with nitrogen. The reaction was heated to reflux for 8 h. The flask was cooled, the stir bar was removed and the reaction was concentrated to a wet solid. The solid was triturated with a solution of ether and ethanol. The mixture was filtered, the solid was washed with an ethanol-ether solution, and the solid was dried under vacuum to yield 8-ethoxymethylene-6,8-dihydro-1-thia-3,6-diaza-as-indacen-7-one: $^1$H NMR (DMSO-d$_6$): δ 10.5 (s, 1H), 9.1 (s, 1H), 7.8 (d, 1H), 7.7 (s, 1H), 7.0 (d, 1H), 4.5 (q, 2H), 1.4 (t, 3H); APCI–MS m/z 245 (M–H)$^-$.

Procedure J

Method for Vinylogous Urea Formation: Preparation of 4-[(7-oxo-6,7-dihydro-1-thia-3,6-diaza-as-indacen-8-ylidenemethyl)-amino]-N-pyridin-2-yl-benzenesulfonamide Example 72

4-[(7-Oxo-6,7-dihydro-1-thia-3,6-diaza-as-indacen-8-ylidenemethyl)-amino]-N-pyridin-2-yl-benzenesulfonamide To a 25 ml round bottom flask was added a stir bar, 246 mg (1.00 mmol) of 8-ethoxymethylene-6,8-dihydro-1-thia-3,6-diaza-as-indacen-7-one. 249 (1.00 mmol) of sulfapyridine and 10 ml of ethanol. The flask was fitted with a water-cooled reflux condenser, and the mixture was heated to reflux using an oil bath with stirring for 18 h. The reaction was allowed to cool and was filtered. The precipitate was washed with excess ethanol and dried under vacuum to yield 321 mg (71%) of the title compound: $^1$H NMR (DMSO-d$_6$): δ 11.9 (br s, 1H), 11.2 (d, 1H), 10.9 (s, 1H), 9.3 (s, 1H), 8.1 (d, 2H), 7.9 (m 3H) 7.8 (m, 1H), 7.6 (d, 2H), 7.2 (d, 1H), 7.2 (d, 1H), 6.9 (t, 1H); C$_{21}$H$_{15}$N$_5$O$_3$S$_2$: APCI–MS m/z 450 (M+H)$^+$.

Note: One equivalent of strong acid, e.g., HCl or methanesulfonic acid, is generally required in this reaction. The acid can be supplied as the aniline salt or as a separate component. Similar conditions can be used for condensing anilines with 3-dimethylaminomethylene-, 3-t-butoxymethylene-, and 3-hydroxymethylene-substituted 2,3-dihydro-1H-indol-2-ones.

Procedure K

Method for 5-N-substituted Amide Formation: Preparation of 2-oxo-3[(4-sulfamoyl-phenyl)-hydrazono]-2,3-dihydro-1H-indole-5-carboxylic acid dimethylamide Example 38

2-Oxo-3[(4-sulfamoyl-phenyl)-hydrazono]-2,3-dihydro-1H-indole-5-carboxylic acid dimethylamide To 100 mg (0.190 mmol) 2-oxo-3[(4-sulfamoyl-phenyl)-hydrazono]-2,3-dihydro-1H-indole-5-carboxylic acid pentafluorophenyl ester in 5 mL acetonitrile was added 50 μL (5.6 M in ethanol, 0.28 mmol) of a solution of dimethylamine and 20 μL (0.25 mmol) of pyridine, and the reaction was stirred overnight. The solution was concentrated, and the resulting solid was triturated with EtOAc to give the title compound as a yellow solid (39 mg, 53%): mp>230° C.; $^1$H NMR (DMSO-d$_6$): δ 12.71 (s, 1H), 11.22 (s, 1H), 7.75 (d, J=8.8 Hz, 2H), 7.60 (s, 1H), 7.58 (d, J=8.8 Hz, 2H), 7.31 (dd, J=1.7, 8.1 Hz, 1H), 7.23 (s, 2H), 6.93 (d, J=8.0 Hz, 1H), 2.95 (s, 6H); APCI–MS: m/z 386 (m–H). Anal. Calcd for C$_{17}$H$_{17}$N$_5$O$_5$S.1/2H$_2$O: C, 51.51; H, 4.58; N, 17.67. Found: C, 51.69; H, 4.25; N, 17.63.

Procedure L

Method for Introducing 4-substituents Via Palladium-catalyzed Coupling: Preparation of 4-(N'-{4-[2-(4-hydroxyphenyl)-vinyl]-2-oxo-1,2-dihydro-indol-3-ylidene}-hydrazino)-benzenesulfonamide (Z isomer)

Example 15

4-(N'-{4-[2-(4-Hydroxyphenyl)-vinyl]-2-oxo-1,2-dihydro-indol-3-ylidene}-hydrazino)-benzenesulfonamide (Z isomer)

A mixture of 1.0 g (3.6 mmol) of 4-iodo-1H-indole-2,3dione (Snow, et al., Journal of the American Chemical Society 1977, 99, 3734–44), 0.42 g (4.2 mmol) of TEA, 0.06 g (0.27 mmol) of palladium(II) acetate, 0.16 g (0.54 mmol) of tri-o-tolylphosphine and 5.0 g (4.2 mmol) of a 10% solution of 4-vinylphenol in propylene glycol was suspended in 15 mL of dry acetonitrile in a pyrex sealed tube and heated to 100° C. for 4 h. The mixture was cooled to rt, quenched with 50 mL of 10% hydrochloric acid and extracted with two 100 mL-portions of EtOAc. The combined extracts were dried over MgSO$_4$ and concentrated to give a brown solid, which was subjected to chromatography on silica gel, eluting with hexane:EtOAc (3:1), to yield 0.125 g (13%) of trans-4-[2-(4-hydroxyphenyl)-vinyl]-1H-indole-2,3-dione as a red solid: $^1$H NMR (DMSO-d$_6$): δ 6.6–7.6 (m, 8H), 7.77 (d, J=16.4 Hz, 1H), 9.85 (bs, 1H), 11.00 (bs, 1H); APCI–MS m/z 264 (M–1)$^-$. Condensation of trans-4-[2-(4-hydroxyphenyl)vinyl]-1H-indole-2,3dione and 4-sulfonamidophenylhydrazine hydrochloride according to Procedure G gave the title compound in 27% yield as an orange solid: $^1$H NMR (DMSO-d$_6$): δ 6.78 (d, J=7.8 Hz, 1H), 6.88 (d, J=8.7 Hz, 2H), 7.26 (t, J=7.8 Hz, 1H), ), 7.29 (s, 2H), 7.36 (d, J=16.5 Hz, 1H), 7.47 (d, J=7.8 Hz, 1H), 7.53(d, J=8.7 Hz, 2H), 7.57 (d, J=8.7 Hz, 2H), ), 7.81 (d, J=8.7 Hz, 2H), 8.03 (d, J=16.5 Hz 1H), 9.78 (s, 1H), 11.17 (s, 1H), 13.02 (s, 1H); APCI–MS m/z433 (M–1)$^-$.

Procedure M

Method for Reducing 4-alkenyl Substituents: Preparation of 4-(N'-{4-[2-(4-hydroxyphenyl)-ethyl]-2-oxo-1,2-dihydro-indol-3-ylidene}-hydrazino)-benzenesulfonamide Example 14

4-N'-{4-[2-(4-Hydroxyphenyl)-ethyl]-2-oxo-1,2-dihydro-indol-3-ylidene}-hydrazino)-benzenesulfonamide A mixture of 0.028 g (0.64 mmol) of 4-(N'-{4-[2-(4-hydroxyphenyl)-vinyl]-2-oxo-1,2-dihydro-indol-3- ylidene}-hydrazino)-benzenesulfonamide (Z isomer) and 0.015 g of 10% palladium on charcoal in 60 mL of MeOH:THF (4:1) was subjected to hydrogenation on a Parr apparatus at 50 psi for 1 h. The mixture was filtered through celite, and the filtrate was concentrated to give 0.026 g (93%) of the title compound as a yellow solid: $^1$H NMR (DMSO-d$_6$): δ 2.82 (t, J=8.0 Hz, 2H), 3.23 (t, J=8.0 Hz, 2H), 6.69 (d, J=8.4 Hz, 2H), 6.78 (d, J=7.7 Hz, 1H), 6.89 (d, J=7.7 Hz, 1H), ), 7.07 (d, J=8.4 Hz, 2H), 7.18 (t, J=7.7 Hz, 1H), 7.26 (s, 2H), 7.45 (d, J=8.8 Hz, 2H), 7.71 (d, J=8.8 Hz, 2H), 9.20 (bs, 1H), 11.12 (s, 1H), 13.02 (s, 1H); APCI–MS m/z435 (M−1)$^-$.

EXAMPLE 1

4-[N'-(4-Nitro-2-oxo-1,2-dihydro-indol-3-ylidene)-hydrazino]-benzenesulfonamide (Z isomer)

The title compound was prepared from 4-nitro-1H-indole-2,3-dione (Gassman, et al., Journal of Organic Chemistry 1977, 42, 1344–8) and 4-sulfonamidophenylhydrazine hydrochloride according to Procedure G in 33% yield: $^1$H NMR (DMSO-d$_6$): δ 7.23 (d, J=7.7 Hz, 1H), 7.31 (s, 2H), 7.47 (t, J=7.9 Hz, 1H), 7.56 (d, J=7.9 Hz, 2H), 7.59 (d, J=7.2 Hz, 1H), 7.83 (d, J=7.7 Hz, 2H), 11.59 (s, 1H), 13.20 (s, 1H); APCI–MS m/z 361 (M)$^-$. Anal. Calcd for $C_{14}H_{11}N_5O_5S$: C, 46.54, H, 3.07; N, 19.38; S, 8.87. Found C, 46.62, H, 3.09; N, 19.46; S. 8.81.

EXAMPLE 2

2-Oxo-3-[(4-sulfamoyl-phenyl)-hydrazono]-2,3-dihydro-1H-indole-4-carboxylic acid amide (E isomer)

1H-Indole-2,3-dione-4-carboxamide was prepared from aniline-3-carboxamide according to Procedure A in 3% yield: $^1$H NMR (DMSO-d$_6$):δ 7.17 (d, J=8.1 Hz, 1H), 7.32 (d, J=8.1 Hz, 1H), ), 7.56 (t, J=8.1 Hz, 1H), 8.02 (bs, 2H), 11.86 (bs, 1H); APCI+MS m/z 191 (M+1)$^-$. Condensation of 1H-indole-2,3-dione-4-carboxamide with 4-sulfonamidophenylhydrazine hydrochloride according to Procedure G gave the title compound in 31% yield: $^1$H NMR (DMSO-d$_6$): δ 7.11 (d, J=8.3 Hz, 1H), 7.18 (s, 2H), 7.27 (d, J=8.8 Hz, 2H), 7.32 (d, J=7.0 Hz, 1H), 7.51 (d, J=7.4 Hz, 1H), 7.75 (d, J=8.8 Hz, 2H), 8.0 (bs, 2H), 10.40 (s, 1H), 10.80 (s, 1H); APCI–MS m/z 359 (M)$^-$. Anal. Calcd for $C_{15}H_{13}N_5O_4S \cdot 0.12 H_2O$: C, 49.83, H, 3.69; N, 19.37; S, 8.86. Found C, 49.71, H, 3.71; N, 19.32; S, 8.84.

EXAMPLE 3

4-[N'-(4-Isopropyl-2-oxo-1,2dihydro-indol-3-ylidene)-hydrazino]-benzenesulfonamide (Z isomer)

The title compound was prepared from 4-isopropyl-1H-indole-2,3-dione (Krantz and Young, 1989, U.S. Pat. No. 4,873,232) and 4-sulfonamidophenylhydrazine hydrochloride according to Procedure G in 73% yield: $^1$H NMR (DMSO-d$_6$): δ 1.30 (d, J=6.7 Hz, 6H), 3.82 (septet, J=6.7 Hz, 1H), 6.76 (d, J=7.8 Hz, 1H), 7.01 (d, J=7.8 Hz, 1H), 7.23 (t, J=7.8 Hz, 1H 7.24 (s, 2H), 7.48 (d, J=8.7 Hz, 2H), 7.79 (d, J=8.7 Hz, 2H), 11.10 (s, 1H), 13.05 (s, 1H); APCI–MS m/z 357 (M−1)$^-$. Anal. Calcd for $C_{17}H_{18}N_4O_3S$: C, 56.97, H. 5.06; N, 15.63; S. 8.95. Found C, 56.88, H, 5.12; N, 15.73; S, 8.91.

EXAMPLE 4

4-[(4-Hydroxymethyl-2-oxo-1,2-dihydro-indol-3-ylidenemethyl)-amino]-N-methyl-benzenesulfonamide A mixture of 3.0 g (20 mmol) of 3-aminobenzyl alcohol, 3.36 g (22.0 mmol) of t-butyldimethylsilyl chloride and 1.52 g (22.0 mmol) of imidazole were dissolved in 20 mL of DMF. The solution was stirred at rt for 16 h and then diluted with 250 mL of hexane and 250 mL of EtOAc. The organic phase was washed twice with brine, dried over MgSO$_4$ and concentrated to give 4.8 g of 3-([t-butyldimethylsilyloxy] methyl-benzenamine as a clear oil. This was dissolved in 100 mL of CH$_2$Cl$_2$, cooled with stirring to −65° C. and 2.17 g (20.0 mmol) of t-butyl hypochlorite was added. After 10 min of stirring, a solution of 2.68 g (20.0 mmol) of ethyl methylthioaceatate in 10 mL of CH$_2$Cl$_2$ was added, and the solution was stirred for 1 h. TEA (2.02 g, 20.0 mmol) was added and the reaction was warmed to rt over 1 h. The solution was washed with water and concentrated to an oil. This was redissolved in 100 mL of ether, 12 mL of 2 N hydrochloric acid was added, and the mixture was stirred overnight. The ether phase was separated and concentrated to an oil. This was chromatographed on silica gel eluting with hexane:EtOAc (initially a 3:1 ratio increasing to 1:2).to yield 0.82 g (20%) of 4-hydroxymethyl-3-methylsulfanyl-1,3-dihydro-indol-2-one: $^1$H NMR (DMSO-d$_6$): δ 1.89 (s, 3H), 4.45 (s, 1H), 4.62 (m, 2H), 5.1 (bs, 1H), 6.87 (d, J=7.7 Hz, 1H), 7.02 (d, J=7.7 Hz, 1H), 7.17 (t, J=7.7 Hz, 1H), 10.44 (s, 1H). Further elution yielded 0.53 g (13%) of 6-hydroxymethyl-3-methysulfanyl-1,3-dihydro-indol-2-one: $^1$H NMR (DMSO-d$_6$): δ 1.99 (s, 3H), 4.48 (s, 2H), 4.50 (s, 1H), 5.1 (bs, 1H), 6.84 (s, 1H), 6.94 (d, J=7.6 Hz, 1H), 7.22 (d, J=7.6 Hz, 1H), 10.54 (s, 1H).

A solution of 0.82 g (3.9 mmol) of 4-hydroxymethyl-3-methylsulfanyl-1,3-dihydro-indol-2-one in DMF (20 mL) was treated with 0.65 g (4.3 mmol) of t-butyldimethylsilyl chloride and 0.3 g (4.4 mmol) of imidazole and stirred for 24 h.

The solution was diluted with 75 mL of hexane and 75 mL of EtOAc. The organic phase was washed with brine, dried over MgSO$_4$ and concentrated to give 1.2 g (95%) of 3-methylsulfanyl-4-(t-butyldimethylsilyloxy)methyl-1,3-dihydro-indol-2-one as a clear oil which crystallised upon storage at rt: $^1$H NMR (DMSO-d$_6$): δ 0.051 (s, 3H), 0.064 (s, 3H), 0.881 (s, 9H), 1.87 (s, 3H), 4.43 (s, 1H), 4.79 (d, J=14.2 Hz, 1H), 4.88 (d, J=14.2 Hz, 1H), 6.70 (d, J=7.9 Hz, 1H), 7.00 (d, J=7.9 Hz, 1H), 7.19 (t, J=7.9 Hz, 1H), 10.48 (s, 1H); APCI–MS m/z 346 (M+23)$^+$.

A solution of 1.2 g (3.7 mmol) of 3-methylsulfanyl-4-(t-butyldimethylsilyloxy)-methyl-1,3-dihydro-indol-2-one in THF (25 mL) was stirred with saturated ammonium chloride solution (20 mL), and activated zinc dust (5 g) was added. The mixture was stirred for 60 h at rt. The organic phase was separated, dried over MgSO$_4$ and concentrated to give 1.16 g of impure 4-t-butyldimethylsilyloxy)methyl-1,3-dihydro-indol-2-one as an off-white solid: $^1$H NMR (DMSO-d$_6$): δ 0.11 (s, 6H), 0.86 (s, 9H), 3.42 (s, 2H), 4.67 (s, 2H), 6.74 (d, J=7.7 Hz, 1H), 695 (d, J=7.7 Hz, 1H) 7.18 (t, J=7.7 Hz, 1H), 10.40 (s, 1H). A solution of 0.64 g (2.3 mmol) of 4-(t-butyldimethylsilyloxy)methyl-1,3-dihydro-indol-2-one in DMF dimethylacetal (5 mL) was heated to 100° C. for 1 h. The excess DMF dimethylacetal was removed under high vacuum, and the resulting dark oil was chromatographed on silica gel, eluting with EtOAc, to give 0.34 g (44%) of 3-dimethylaminomethylene-4-(t-butyldimethyl-silyloxy) methyl-1,3-dihydro-indol-2-one as a white solid: $^1$H NMR (DMSO-d$_6$): δ −0.03 (s, 6H), 0.81 (s, 9H), 3.29 (s, 6H), 4.64 (s, 2H), 6.66 (d, J=7.3 Hz, 1H), 6.73 (d, J=7.3 Hz, 1H), 6.79 (t, J=7.3 Hz, 1H), 7.76 (s, 1H), 9.97 (s, 1H) ); APCI–MS m/z 333 (M+1)$^+$. A solution of 0.115 g (0.34 mmol) of 3-dimethylaminomethylene-4-(t-butyldimethylsilyloxy) methyl-1,3-dihydro-indol-2-one in ethanol (10 mL) was treated with 0.076 g (0.34 mmol) N-methylsulfanilamide hydrochloride. The solution was refluxed for 0.5 h and cooled to rt. The resulting yellow precipitate was isolated by filtration, washed with ethanol and dried to yield 0.048 g (38%) of the title compound: $^1$H NMR (DMSO-d$_6$): δ 2.37 (d, J=5.0 Hz, 3H), 4.67 (s, 2H), 5.3 (bs, 1H), 6.78 (d, J=7.5 Hz, 1H), 6.93 (d, J=7.5 Hz, 1H), 6.99 (t, J=7.5 Hz, 1H), 7.33 (q, J=5.0 Hz, 1H), 7.44 (d, J=8.6 Hz, 2H), 7.71 (d, J=8.6 Hz, 2H), 8.32 (d, J=12.2 Hz, 1H), 10.67 (s, 1H), 11.26 (d, J=12.2 Hz, 1H); APCI–MS m/z 358 (M−1)$^−$. Anal. Calcd for C$_{17}$H$_{17}$N$_3$O$_4$S: C, 56.81, H, 4.77; N, 11.69, S, 8.92. Found C, 56.89, H, 4.81; N, 11.70; S, 8.84.

EXAMPLE 5

4-N'-[2-Oxo-4-2-pyridin-4-yl-ethyl)-1,2-dihydro-indol-3-ylidene]-hydrazino}-benzenesulfonamide (Z isomer)

A mixture of 3.0 g (20 mmol) of 3-nitroiodobenzene, 3.5 mL (25 mmol) of TEA, 0.045 g (0.20 mmol) of palladium (II) acetate and 2.77 g (25.0 mmol) of 4-vinylpyridine was suspended in 4 mL of dry acetonitrle in a pyrex sealed tube and heated to 100° C. for 48 h. The mixture was cooled to rt and was quenched with 200 mL of 10% hydrochloric acid. The resulting yellow solid was isolated by filtration and partitioned between 250 mL of EtOAc and 250 mL of 1 N aqueous sodium hydroxide. The organic phase was dried over MgSO$_4$ and concentrated to give 3.0 g (66%) of 4-[2-(3-nitrophenyl)ethenyl]-pyridine as a yellow solid: $^1$H NMR (DMSO-d$_6$): δ 3.0–4.6 (br s, 1H), 7.71–7.78 (m, 2H), 8.07 (d, J=15.8 Hz, 1H), 8.13–8.16 (m, 3H), 8.24 (d, J=8.0 Hz, 1H), 8.56 (s, 1H), 8,84 (d, J=5.7 Hz, 2H); ESI–MS m/z 227 (M+1)$^+$. A portion (1.3 g, 7.1 mmol) of this solid was dissolved in 100 mL of EtOAc, and 0.5 g of 10% palladium on charcoal was added. The mixture was hydrogenated on a Parr apparatus at 40 psi for 1.5 h. Another 0.5 g batch of 10% palladium on charcoal was added and the mixture was subjected to further hydrogenation for 1 h. The palladium catalyst was removed by filtration through a pad of celite, and the filtrate was concentrated to give 1.13 g (100%) of 3-(4-pyridinyl)ethylaniline: $^1$H NMR (DMSO-d$_6$): δ 2.69 (m, 2H), 2.80 (m, 2H), 4.9 (bs, 2H), 6.33 (d, J=7.7 Hz, 2H), 6.38 (s, 1H), 6.86 (t, J=7.7 Hz, 1H), 7.20 (d, J=5.8 Hz, 2H), 8.41 (d, J=5.8 Hz, 2H). Conversion of 3-[2-(4-pyridinyl) ethyl]-aniline to 4-2-pyridin-4-yl-ethyl)-1H-indole-2,3-dione was accomplished according to Procedure A in 24% overall yield: $^1$H NMR (DMSO-d$_6$): δ 2.80 (m, 2H), 3.10 (m, 2H), 6.70 (d, J=8.0 Hz, 1H), 6.81 (d, J=8.0 Hz, 1H), 7.24 (m, 2H), 7.40 (t, J=8.0 Hz, 2H), 8.42 (bs, 2H), 11.00 (s, 1H). Conversion of 4-(2-pyridin-4-yl-ethyl)-1H-indole-2,3dione to the title compound was accomplished according to Procedure G in 40% overall yield: $^1$H NMR (DMSO-d$_6$): δ 2.98 (t, J=7.9 Hz, 2H), 3.30 (m, 2H, underneath water peak), 6.78 (d, J=7.7 Hz, 1H), 6.88 (d, J=7.6 Hz, 1H), 7.17 (t, J=7.6 Hz, 1H), 7.25 (s, 2H), 7.29 (d, J=6.0 Hz, 2H), 7.37 (d, J=8.8 Hz, 2H), 7.66 (d, J=8.8 Hz, 2H), 8.47 (d, J=6.0 Hz, 2H), 11.13 (s, 1H), 12.98 (s, 1H); APCI–MS m/z 420 (M−1)$^−$. Anal. Calcd for C$_{21}$H$_{19}$N$_5$O$_3$S.0.15 HCl: C, 55.93, H, 4.43; N, 15.53; S, 7.11. Found C, 56.05, H, 4.36; N, 15.38; S, 7.18.

EXAMPLE 6

2-Oxo-3-(4-sulfamoyl-phenylamino)-methylene]-2,3-dihydro-1H-indole-4-carboxylic acid ethyl ester (Z isomer)

The title compound was prepared from 2-oxo-2,3-dihydro-1H-indole4-carboxylic acid ethyl ester (Connolly and Durst, Synlett 1996, 663–4; Kozikowski and Kuniak, Journal of Organic Chemistry 1978, 43, 2083–4) and sulfanilamide according to Procedure J in 14% overall yield: $^1$H NMR (DMSO-d$_6$): δ 1.33 (t, J=7.1 Hz, 3H), 4.37 (q, J=7.1 Hz, 2H), 7.10 (d, J=7.6 Hz, 1H), 7.15 (t, J=7.6 Hz, 1H). 7.30 (s, 2H), 7.41 (d, J=8.6 Hz, 2H), 7.57 (d, J=7.6 Hz, 1H), 7.82 (d, J=8.6 Hz, 2H)), 9.50 (d, J=12.6 Hz, 1H), 10.96 (s, 1H), 11.75 (d, J=12.6 Hz, 1H); APCI–MS m/z 386 (M−1)$^−$.

EXAMPLE 7

4-[N'-(4-Iodo-2-oxo-1,2-dihydro-indol-3-ylidene)-hydrazino]-benzenesulfonamide (Z isomer)

The title compound was prepared from 4-iodo-1H-indole-2,3-dione (Snow, et al., Journal of -the American Chemical Society 1977, 99, 3734–44) and 4-sulfonamidophenyl-hydrazine hydrochloride according to Procedure G in 87% overall yield: $^1$H NMR (DMSO-d$_6$): δ 6.93 (d, J=7.6 Hz, 1H), 6.99 (t, J=7.6 Hz, 1H), 7.25 (s, 2H), 7.50 (d, J=7.6 Hz, 1H), 7.66 (d, J=8.7 Hz, 2H), 7.77 (d, J=8.7 Hz, 2H), 11.17 (s, 1H), 12.94 (s,1H); APCI–MS m/z 441 (M−1)$^−$. Anal. Calcd for C$_{14}$H$_{11}$IN$_4$O$_3$S: C, 38.02, H, 2.51; I, 28.70; N, 12.67; S, 7.25. Found C, 38.05, H, 2.51; I, 28.78; N, 12.64; S, 7.19.

EXAMPLE 8

4-[N'-(4-Isobutyl-2-oxo-1,2-dihydro-indol-3-ylidene)-hydrazino]-benzenesulfonamide A mixture of 0.20 g (1.0 mmol) of 4-(2-methyl-propenyl)-1H-indole-2,3-dione and 0.05 g of 10% palladium on charcoal in 25 mL of EtOAc was subjected to hydrogenation on a Parr apparatus at 46 psi for 1 h. The mixture was filtered through celite, and the filtrate was concentrated to dryness. The solid was purified by chromatography on silica gel, eluting with hexane:EtOAc (4:1), to furnish 0.027 g (13%) of 4-isobutyl-1H-indole-2,3-dione: $^1$H NMR (DMSO-d$_6$): δ 0.89 (d, J=6.7 Hz, 6H), 1.86 (nonet, J=6.7 Hz, 1H), 2.72 (d, J=6.7 Hz, 1H), 6.74 (d, J=7.8 Hz, 1H), 6.86 (d, J=7.8 Hz, 1H), 7.48 (t, J=7.8 Hz, 1H), 11.03 (s, 1H).

Condensation of 4-isobutyl-1H-indole-2,3-dione and 4-sulfonamido-phenylhydrazine hydrochloride according to Procedure G gave the title compound in 65% yield: $^1$H NMR (DMSO-d$_6$): δ 0.96 (d, J=6.4 Hz, 6H), 2.05 (m, 1H), 2.87 (d, J=7.0 Hz, 2H), 6.79 (d, J=7.6 Hz, 1H), 6.85 (d, J=7.6 Hz 1H), 7.20 (t, J=7.6 Hz, 1H), 7.26 (s, 2H), 7.51 (d, J=8.5 Hz, 2H), 7.81 (d, J=8.5 Hz, 2H), 11.13 (s, 1H), 13.03 (s,1H); APCI–MS m/z 371 (M−1)$^−$.

EXAMPLE 9

4{N'-[4-(2-Methyl-propenyl)-2-oxo-1,2-dihydro-indol-3-ylidene]-hydrazino}-benzenesulfonamide By methods described in Procedure L, 4-(2-methyl-propenyl)-1H-indole-2,3-dione was prepared from 4-iodo-1H-indole-2,3-dione and isobutylene in 34% yield: $^1$H NMR (DMSO-d$_6$): δ 1.82 (s, 3H), 1.90 (s, 3H), 6.79 (d, J=7.9 Hz, 1H), 6.94 (d, J=7.9 Hz, 1H), 7.47 (t, J=7.9 Hz, 1H), 10.97 (s, 1H); APCI–MS m/z 200 (M−1)$^−$. Condensation of 4-(2-methyl-propenyl1H-indole-2,3-dione and 4-sulfonamidophenylhydrazine hydrochloride according to Procedure G gave the title compound as a yellow solid (51% yield): $^1$H NMR (DMSO-d$_6$): δ 1.84 (s, 3H), 2.04 (s, 3H), 6.78 (s, 1H), 6.79 (d, J=7.8 Hz, 1H), 6.96 (d, J=7.8 Hz, 1H), 7.24 (t, J=7.8 Hz, 1H), 7.24 (s, 2H), 7.48 (d, J=8.8 Hz, 2H), 7.80 (d, J=8.8 Hz, 2H), 11.11 (s, 1H), 12.91 (s, 1H); APCI–MS m/z 369 (M−1)$^−$. Anal. Calcd for C$_{18}$H$_{18}$N$_4$O$_3$S:

C, 58.36, H. 4.90; N, 15.12; S, 8.66. Found C, 58.41, H. 4.87; N, 15.18; S, 8.56.

EXAMPLE 10

4-{N'-[4-(2-Methyl-1-butenyl)-2-oxo-1,2-dihydro-indol-3-ylidene]-hydrazino}-benzenesulfonamide and 4{N'-[4-(2-methyl-2-butenyl)-2-oxo-1,2-dihydro-indol-3-ylidene]-hydrazino}benzenesulfonamide Coupling of 4-iodoisatin and 2-methyl-1-butene according to Procedure L gave a mixture of isomers [the major pair of isomers was E/Z4-(2-methyl-1-butenyl)-1H-indole-2,3-dione and the minor pair of isomers was E/Z4-(2-methyl-2-butenyl)-1H-indole-2,3-dione] in 21% yield.: $^1$H NMR (DMSO-$d_6$, integral ratios are normalized to the 1H singlet observed at δ 10.97): δ 1.06 (m, 2.6H), 1.47 (s, 1.05H), 1.83 (m, 1.4H), 1.88 (s, 1.1H), 2.19 (m, 1.6H), 3.50 (s, 0.26H), 5.22 (m, 0.16H), 6.60–6.72 (m, 2H), 6.76–6.82 (m, 0.23H), 6.86 (d, J=7.7 Hz, 0.35H), 7.46 (d, J=7.6 Hz, 0.42H), 7.4–7.6 (m, 1H), 10.97 (s, 1H); APCI–MS m/z 214 (M–1)$^-$. Condensation of the mixture of E/Z-4-(2-methyl-1-butenyl)-1H-indole-2,3-dione and E/Z-4-2-methyl-2-butenyl)-1H-indole-2,3-dione and 4-sulfonamidophenyl-hydrazine hydrochloride according to Procedure G gave the title compound mixture as a yellow solid (51% yield): $^1$H NMR (DMSO-$d_6$, integral ratios are normalized to the 1H singlet observed at δ 11.11): δ 1.07 (t, J=7.5 Hz, 1.3H), 1.21 (t, J=7.5 Hz, 1.3H), 1.54 (d, J=6.5 Hz, 0.7H), 1.63 (s, 0.7H), 1.86 (s, 1.2H), 2.03 (s, 1.1H), 2.21 (q, J=7.7 Hz, 0.7H), 2.32 (q, J=7.7 Hz, 0.8H), 3.71 (s, 0.4H), 5.2 (m, 0.2H), 6.72–6.85 (m, 2.1H), 6.89 (d, J=7.9 Hz, 0.39H), 6.97 (d, J=7.9 Hz, 0.42H), 7.18–7.26 (m, 3.1H), 7.47–7.51 (m, 2.1H), 7.77–7.81 (m, 2.1H), 11.11 (s, 1H), 12.89 (s, 0.3H), 12.97 (s, 0.35H), 13.02 (s, 0.24H); APCI–MS m/z 383 (M–1)$^-$.

EXAMPLE 11

4-{N'-[4-(2-methylbutyl)-2-oxo-1,2-dihydro-indol-3-ylidene]-hydrazino}-benzenesulfonamide Reduction of the mixture of 4-{N'-[4-2-methyl-1-butenyl)-2oxo-1,2-dihydro-indol-3-ylidene]-hydrazino}benzenesulfonamide and 4-{N'-[4-2-methyl-2-butenyl)-2-oxo-1,2-dihydro-indol-3-ylidene]-hydrazino}benzenesulfonamide according to Procedure M gave the title compound in 79% yield: $^1$H NMR (DMSO-$d_6$): δ 0.87–0.90 (m, 6H), 1.21–1.25 (m, 2H), 1.47–1.63 (m, 1H), 2.82 (dd, J=12.6, 8.1 Hz, 1H), 2.95 (dd, J=12.6, 6.6 Hz, 1H), 6.77 (d, J=7.7 Hz, 1H), 6.84 (d, J=7.7 Hz, 1H), 7.18 (t, J=7.7 Hz, 1H), 7.25 (s, 2H), 7.49 (d, J=8.6 Hz, 2H), 7.79 (d, J=8.6 Hz, 2H), 11.12 (s, 1H), 13.04 (s, 1H); APCI–MS m/z 385 (M–1)$^-$.

EXAMPLE 12

4-[N'-4-Cyclobutylmethyl-2-oxo-1,2-dihydro-indol-3-ylidene)-hydrazino]benzenesulfonamide (Z isomer)

Reduction of 4-[N'-(4-cyclobutylidenemethyl-2-oxo-1,2-dihydro-indol-3-ylidene)-hydrazino]-benzenesulfonamide according to methods described in Procedure M gave the title compound in 94% yield: $^1$H NMR (DMSO-$d_6$): δ 1.81 (m, 4H), 1.96 (m, 2H), 2.73 (m, 1H), 3.07 (d, J=7.2 Hz, 2H), 6.76 (d, J=7.8 Hz, 1H), 6.86 (d, J=7.8 Hz, 1H), 7.17 (t, J=7.8 Hz, 1H), 7.24 (s, 2H), 7.48 (d, J=8.6 Hz, 2H), 7.79 (d, J=8.6 Hz, 2H), 11.08 (s, 1H). 12.93 (s, 1H); APCI–MS m/z 383 (M–1)$^-$.

EXAMPLE 13

4-[N'-(4-Cyclobutylidenemethyl-2-oxo-1,2-dihydro-indol-3-ylidene)-hydrazino]-benzenesulfonamide (Z isomer)

By methods described in Procedure L, 4-cyclobutylidenemethyl-1H-indole-2,3-dione was prepared from 4-iodo-1H-indole-2,3-dione and methylene cyclobutene in 25% yield: $^1$H NMR (DMSO-$d_6$): δ 2.08 (quintet, J=7.8 Hz, 2H), 2.91 (m, 2H), 3.06 (m, 2H), 6.67 (d, J=7.7 Hz, 1H), 6.94 (d, J=7.7 Hz, 1H), 6.96 (s, 1H), 7.47 (d, J=7.7 Hz, 1H), 11.00 (bs, 1H); APCI–MS m/z 211 (M–1)$^-$. Condensation of 4-(cyclobutylidenemethyl)-1H-indole-2,3-dione and 4-sulfonamidophenylhydrazine hydrochloride according to Procedure G gave the title compound in 76% yield: $^1$H NMR (DMSO-$d_6$): δ 2.11 (quintet, J=7.8 Hz, 2H), 3.00 (t, J=7.8 Hz, 2H), 3.06 (t, J=7.8 Hz, 2H), 6.74 (d, J=7.7 Hz, 1H), 6.97 (d, J=7.7 Hz, 1H), 7.07 (s, 1H), 7.21 (t, J=7.7 Hz, 1H), 7.25 (s, 2H), 7.47 (d, J=8.7 Hz, 2H), 7.81 (d, J=8.7 Hz, 2H), 11.12 (s, 1H), 13.03 (s, 1H); APCI–MS m/z 381 (M–1)$^-$.

EXAMPLE 14

See Procedure M

EXAMPLE 15

See Procedure L

EXAMPLE 16

4-[N'-(2-Oxo-4-phenoxy-1,2-dihydro-indol-3-ylidene)-hydrazino]-benzenesulfonamide (mixture of E and Z isomers)

The title compound was prepared from 3-phenoxyaniline and 4-sulfonamidophenyl-hydrazine hydrochloride according to Procedure C: mp>250° C.; $^1$H NMR (DMSO-$d_6$): δ 6.42 E (d, J=8.4 Hz, 1H), 6.70 E (d, J=7.7 Hz, 1H), 6.76 Z (d, J=8.2 Hz, 1H), 6.82 Z (d, J=7.8 Hz, 1H), 6.99 Z (d, J=8.1 Hz, 2H), 7.06 Z (d, J=8.8 Hz, 2H), 7.1–7.6 E (m, 10H), 7.1–7.6 Z (m, 6H), 7.62 Z (d, J=8.8 Hz, 2H), 7.74 E (d, J=8.7 Hz, 2H), 10.88 E (s, 1H), 11.18 E (s, 1H), 11.27 Z (s, 1H), 12.77 Z (s, 1H); APCI–MS: m/z 407 (M–H)$^-$. Anal. Calcd for $C_{20}H_{16}N_4O_4S$: C, 58.81; H, 3.95; N, 13.72; S, 7.85. Found: C, 58.53; H, 4.02; N, 13.66; S, 7.79.

EXAMPLE 17

See Procedure C

EXAMPLE 18

4-{N'-[2-Oxo-4-(1H-pyrazol-3-yl)-1,2-dihydro-indol-3-ylidene]-hydrazino}-benzenesulfonamide 4-(1H-Pyrazol-3-yl)-1H-indole-2,3-dione was prepared from 3-(1H-pyrazol-3-yl)aniline according to Procedure A. The title compound was prepared from 4-(1H-pyrazol-3-yl) isatin and 4-sulfonamidophenylhydrazine hydrochloride according to Procedure G: $^1$H NMR (DMSO-$d_6$): δ 6.72 (s, 1H), 7.22 (s, 2H), 7.39 (s, 1H), 7.48–7.60 (m, 4H), 7.76 (d, J=8.7 Hz, 2H), 7.77 (s, 1H), 11.11 (s, 1H), 12.93 (s, 1H); ESI–MS: m/z 381 (M–H)$^-$.

EXAMPLE 19

4-[(5-Oxazol-5-yl-2-oxo-1,2-dihydro-indol-3-ylidenemethyl)amino]-benzenesulfonamide (Z-somer)

The title compound was prepared in 68% yield from ethoxymethylene-5-oxazol-5-yl-1,3-dihydro-indol-2-one and 4-aminobenzenesulfonamide hydrochloride according to Procedure J: $^1$H NMR (DMSO-$_6$): δ 10.79 (d,$_1$H), 10.73 (s, 1H), 8.76 (d, 1H), 8.38 (s, 1H), 8.0 ( s, 1H), 7.77 (d, 2H), 7.56 ( d, 2H), 7.43 (s, 1H), 7.40 (d, 1H), 7.26 (s, 2H), 6.91 (d, 1H); APCI–MS: m/z 381 (MH)$^-$.

EXAMPLE 20

2-Oxo-3-[(4-sulfamoyl-phenyl)-hydrazono-2,3-dihydro-1H-indole-5-carboxylic acid pentafluorophenyl ester 2-Oxo-3-[(4-sulfamoyl-phenyl)hydrazono]-2,3-dihydro-1H-indole-5-carboxylic acid was prepared from 1H-indole-2,3-dione-5-carboxylic acid and 4-sulfonamidophenyl-hydrazine hydrochloride according to Procedure G. To a suspension of 2.75 g (7.63 mmol) of the 2-oxo-3[(4-sulfamoyl-phenyl)-hydrazono]-2,3-dihydro-1H-indole-5-carboxylic acid in 20 mL DMF was added 1.38 mL (8.03 mmol) pentafluorophenyltrifluoroacetate (PFPTFA), 0.69 mL (8.53 mmol) pyridine, and the suspension was stirred under N$_2$ for 20 min. TLC (silica gel, 20% MeOH/CH$_2$Cl$_2$) indicated residual starting material remained, and the reaction was treated with 10 mL DMF and additional PFPTFA and pyridine (equal portions to above). The reaction was stirred overnight and then poured into 400 mL ether. The solution was washed with two 500-mL portions of water, and 300 mL of EtOAc was added to dissolve precipitate. The solution was washed with 500 mL water, dried over Na$_2$SO$_4$, filtered through silica gel and concentrated to remove ether. The resulting solid was collected by filtration, washed 50 mL 1:1 ethylacetate:hexanes and dried overnight in a vacuum oven at 70° C. to give the title compound as a bright yellow solid (2.30 g, 57%): mp>230° C.; $^1$H NMR (DMSO-d$_6$):δ 12.77 (s, 1H), 11.68 (s, 1H), 8.32 (d, J=1.9 Hz. 1H), 8.11 (dd, J=1.9 Hz, J=8.2 Hz, 1H), 7.79 (d, J=8.9 Hz, 2H), 7.67 (d, J=8.9 Hz, 2H), 7.28 (s, 2H), 7.16 (d, J=8.4 Hz, 1H); APCI–MS: m/z 525 (M–H)$^-$. Anal. Calcd for C$_{21}$H$_{11}$N$_4$O$_5$SF$_5$: C, 47.92; H. 2.11; N, 10.64. Found: C, 48.00; H, 2.13; N, 10.54.

EXAMPLE 21

4-[N'-(5-Nitro-2-oxo-1,2-dihydro-indol-3-ylidene)-hydrazino]-benzenesulfonamide (Z isomer)

The title compound was prepared from 5-nitro-1H-indole-2,3-dione (Gassman, et al., Journal of Organic Chemistry 1977, 42, 1344–8) and 4-sulfonamidophenylhydrazine hydrochloride according to Procedure G in 94% yield: $^1$H NMR (DMSO-d$_6$): δ 7.14 (d, J=8.6 Hz, 1H), 7.33 (s, 2H), 7.75 (d, J=8.8 Hz, 2H), 7.84 (d, J=8.8 Hz, 2H), 8.23 (dd, J=2.2, 8.6 Hz, 1H), 8.42 (d, J=2.2 Hz, 1H), 11.76 (s, 1H), 12.78 (s, 1H). Anal. Calcd for C$_{14}$H$_{11}$N$_5$O$_5$S: C, 46.54, H, 3.07; N, 19.38. Found C, 46.76, H, 3.13; N, 19.23.

EXAMPLE 22

4-[N'-(5-Hydroxy-2-oxo-1,2-dihydro-indol-3-ylidene)-hydrazino]-benzenesulfonamide (Z isomer)

The title compound was prepared from 5-hydroxy-1H-indole-2,3dione (Ijaz, et al., Indian Journal of Chemistry 1994, 33B, 288–9) and 4-sulfonamidophenylhydrazine hydrochlorideaccording to Procedure G in 30% yield: $^1$H NMR (DMSO-d$_6$): δ 6.79 (dd, J=2.2, 8.3 Hz, 1H), 6.72 (d, J=8.3 Hz, 1H), 6.98 (d, J=2.2 Hz, 1H), 7.25 (s, 2H), 7.53 (d, J=8.7 Hz, 2H), 7.78 (d, J=8.7 Hz, 2H), 9.20 (s, 1H), 10.80 (s, 1H), 12.82 (s, 1H); APCI–MS m/z 331 (M–H)$^-$.

EXAMPLE 23

4-[N'-(5-Methyl-2-oxo-1,2-dihydro-indol-3-ylidene)-hydrazino]-benzenesulfonamide (E isomer)

The title compound was prepared from 5-methyl-1H-indole-2,3-dione (Gassman, et al., Journal of Organic Chemistry 1977, 42, 1344–8) and 4-sulfonamidophenylhydrazine hydrochloride according to Procedure G in 86% yield: $^1$H NMR (DMSO-d$_6$): δ 2.3 (s, 3H), 6.76 (d, J=7.9 Hz, 1H), 7.11 (d, J=7.9 Hz. 1H), 7.20 (s, 2H), 7.57 (d, J=8.8 Hz, 2H), 7.77 (d, J=8.8 Hz, 2H), 8.02 (s, 1H), 10.51 (s, 1H), 10.62 (s, 1H); APCI–MS m/z 329 (M–1)$^-$. Anal. Calcd for C$_{15}$H$_{14}$N$_4$O$_3$S: C, 54.54, H, 4.27; N, 16.96; S, 9.71. Found C, 54.54, H, 4.32; N, 16.87; S. 9.62.

EXAMPLE 24

N-Methyl-4-[N'-(2-oxo-5-[1,2,4]triazol-1-yl-1,2-dihydro-indol-3-ylidene)-hydrazino]-benzenesulfonamide (Z isomer)

5-[1,2,4]Triazol-1-yl-1H-indole-2,3dione was prepared from 4-[1,2,4]-triazol-1-yl-phenylamine according to Procedure A in 6% yield: $^1$H NMR (DMSO-d$_6$): δ 7.04 (d, J=8.4 Hz, 1H), 7.97 (d, J=2.2 Hz, 1H), 8.01 (dd, J=2.2, 8.4 Hz, 1H), 8.20 (s, 1H), 9.26 (s, 1H), 11.19 (bs, 1H); APCI–MS m/z 215 (M+1)$^+$. Condensation of 5-[1,2,4]triazol-1-yl-1H-indole-2,3-dione with 4-hydrazino-N-methyl-phenylsulfonamide according to Procedure G gave the title compound in 86% yield: $^1$H NMR (DMSO-d$_6$): δ 2.38 (d, J=5.0 Hz, 3H), 7.05 (d, J=8.4 Hz, 1H), 7.30 (q, J=5.0 Hz, 1H), 7.65 (d, J=8.7 Hz, 2H), 7.72 (d, J=8.7 Hz, 3H), 8.01 (s, 1H), 8.20 (s, 1H), 9.23 (s, 1H), 11.27 (s, 1H), 12.80 (s, 1H); Anal. Calcd for C$_{16}$H$_{15}$N$_7$O$_3$S.1.3 H$_2$O: C, 48.52, H, 4.22; N, 23.30; S, 7.62. Found C, 48.53, H, 4.25; N, 23.17; S, 7.55.

EXAMPLE 25

2-Oxo-3-[(4-sulfamoyl-phenyl)-hydrazono]-2,3-dihydro-1H-indole-5-sulfonic acid Sodium salt The title compound was prepared from 1H-indole-2,3-dione-5-sulfonic acid and 4-sulfonamidophenylhydrazine according to Procedure G: $^1$H NMR (DMSO-d$_6$): δ6.83 (d. J=8.0 Hz, 1H), 7.22 (s, 2H), 7.50 (dd, J=1.7, 8.0 Hz, 1H), 7.56 (d, J=8.7 Hz, 2H), 7.76 (d, J=8.7 Hz, 2H), 7.77 (d, J=1.7 Hz, 1H), 11.12 (s, 1H), 12.70 (s, 1H); APCI–MS: m/z 395 (M–H)$^-$. Anal. Calcd for C$_{14}$H$_{11}$N$_4$O$_6$S$_2$Na.0.9H$_2$O.0.2 C$_2$H$_6$O: C, 38.97; H, 3.18; N, 12.62; S, 14.45. Found: C, 38.84; H, 3.31; N, 12.63; S, 14.59.

EXAMPLE 26

3-[(4-Methylsulfamoyl-phenyl)-hydrazono]-2-oxo-2,3-dihydro-1H-indole-5-carboxylic acid amide The title compound was prepared from 1H-indole-2,3-dione-5carboxylic acid amide and 4-N-methylsulfonamidophenylhydrazine according to Procedure G: mp>250° C.; $^1$H NMR (DMSO-d$_6$): δ 2.37 (d, J=5.0 Hz, 3H), 6.94 (d, J=8.2 Hz, 1H), 7.26 (bs, 1H), 7.30 (q, J=5.1 Hz, 1H), 7.62 (d, J=8.7 Hz, 2H), 7.72 (d, J=8.7 Hz, 2H), 7.82 (dd, J$_1$=1.5 Hz, J$_2$=8.2 Hz, 1H), 7.96 (bs, 1H), 8.12 (s, 1H), 11.30 (s, 1H), 12.73 (s, 1H); APCI–MS: m/z 372 (M–H)$^-$.

EXAMPLE 27

See Procedure E

EXAMPLE 28

5-Bromo-3-[(4-methylsulfonyl-phenyl)-hydrazono]-1,3-dihydro-indol-2-one

The title compound was prepared in 72% yield from 5-bromo-1H-indole-2,3-dione (Meth-Cohn and Goon, Tetrahedron Letters 1996, 37, 9381–4) and 4-methylsulfonylphenylhydrazine according to Procedure G: $^1$H NMR (DMSO-d$_6$): δ 12.7 (s, 1H), 11.3 (s, 1H), 7.9 (d, 2H), 7.7–7.8 (m, 3H), 7.4 (dd,$_1$H), 6.9 (d, 1H), 3.2 (s, 3H); ESI–MS m/z 392 (M–H)$^-$.

EXAMPLE 29

3-(3H-Benzotriazol-5-ylimino-methylene)-5-iodo-1,3-dihydro-indol-2-one

The title compound was prepared in 43% yield from 3-hydroxymethylene-1,3-dihydro-indol-2-one and 5-aminobenzotriazole according to Procedure J: $^1$H NMR (DMSO-d$_6$): δ 10.8 (d, 1H), 10.7 (s, 1H), 8.8 (d, 1H), 8.0 (s, 1H), 7.8–7.9 (br m), 7.5 (d, 1H), 7.3 (d, 1H); ESI–MS m/z 404 (M+H)$^+$.

EXAMPLE 30

2-Oxo-3-[(4-sulfamoyl-phenyl)-hydrazono]-2,3-dihydro-1H-indole-5-sulfonic acid amide The title compound was prepared from 1H-indole-2,3-dione-5-sulfonic acid amide and 4-sulfonamidophenylhydrazine hydrochloride according to Procedure G: mp>250° C.; $^1$H NMR (DMSO-d$_6$): δ 7.04 (d, J=8.4 Hz, 1H), 7.25 (s, 2H), 7.26 (s, 2H), 7.60 (d, J=8.9 Hz, 2H), 7.70 (dd, J=8.2, 1.9 Hz, 1H), 7.78 (d, J=8.7 Hz, 2H), 7.98 (d, J=1.6 Hz, 1H), 11.43 (s, 1H), 12.75 (s, 1H); APCI–MS m/z 395 (M)$^{-+}$. Anal. Calcd for C$_{14}$H$_{13}$N$_5$O$_5$S$_2$.0.5 H$_2$O: C, 41.58; H, 3.49; N, 17.32; S, 15.86. Found: C, 41.67; H, 3.46; N, 17.26; S, 15.78.

EXAMPLE 31

4-[N'-(5-Methylsulfonyl-2oxo-1,2-dihydro-indol-3-ylidene)-hydrazino]-benzenesulfonamide 5-Methylsulfonyl-1H-indole-2,3-dione was prepared from 4-methylsulfonylaniline according to Procedure A: $^1$H NMR (DMSO-d$_6$): δ 3.21 (s, 3H), 7.07(d, J=8.3 Hz, 1H), 7.92 (d, J=1.7 Hz, 1H), 8.05 (dd, J=8.2, 2.0 Hz, 1H), 11.46 (s,1H); APCI–MS m/z 225 (M)$^{-+}$. The title compound was prepared from 5-methylsulfonyl-1H-indole-2,3-dione and 4-sulfonamidophenylhydrazine hydrochloride according to Procedure G: mp>250° C.; $^1$H NMR (DMSO-d$_6$): δ 3.20 (s, 3H), 7.11 (d, J=8.3 Hz, 1H), 7.26 (s, 2H), 7.65 (d, J=8.9 Hz, 2H), 7.78 (d, J=8.7 Hz, 2H), 7.79 (dd, J=8.2, 1.9 Hz, 1H), 8.06 (d, J=1.6 Hz, 1H), 11.54 (s, 1H), 12.75 (s, 1H); APCI–MS m/z 394 (M)$^{-+}$. Anal. Calcd for C$_{15}$H$_{14}$N$_4$O$_5$S$_2$.0.9 H$_2$O: C, 43.87; H, 3.88; N, 13.64; S, 15.62. Found: C, 43.96; H, 3.80; N, 13.58; S, 15.67.

EXAMPLE 32

3-[(4-Methylsulfamoyl-phenyl)-hydrazono]-2-oxo-2,3-dihydro-1H-indole-5-sulfonic acid methylamide 1H-indole-2,3-dione-5-sulfonic acid methylamide was prepared from N-methylsulfonamidoaniline hydrochloride according to Procedure A: $^1$H NMR (DMSO-d$_6$): δ 2.37 (d, J=4.7 Hz, 3H), 7.04 (d, J=8.4 Hz, 1H), 7.45 (q. J=5.0 Hz, 1H), 7.73 (s, 1H), 7.91 (d, J=8.4 Hz, 1H), 11.38 (s, 1H); APCI–MS m/z 239 (M–H)$^-$. The title compound was prepared from 1H-indole-2,3dione-5-sulfonic acid methylamide and 4-N-methylsulfonamido)-phenylhydrazine according to Procedure G: mp>250° C.; $^1$H NMR (DMSO-d$_6$): δ 2.38 (d, J=4.9 Hz, 6H), 7.08 (d, J=8.2 Hz, 1H), 7.33(q, J=5.2 Hz, 1H), 7.35 (q, J=4.9 Hz, 1H), 7.65 (d, J=8.7 Hz, 2H), 7.66 (dd, J=8.1, 1.8 Hz, 1H), 7.73 (d, J=8.8 Hz, 2H), 7.91 (d, J=1.5 Hz, 1H), 11.48 (s, 1H), 12.77 (s, 1H); APCI–MS m/z 422 (M–H)$^-$. Anal. Calcd for C$_{16}$H$_{17}$N$_5$O$_5$S$_2$: C, 45.38; H, 4.05; N, 16.54. Found: C, 45.46; H, 4.04; N, 16.45.

EXAMPLE 33

4-{N'[5-(1-Hydroxyimino-ethyl)-2-oxo-1,2-dihydro-indol-3-ylidene]-hydrazino}-N-methyl-benzenesulfonamide 5-(1-Hydroxyiminoethyl)-1H-indole-2,3-dione was prepared from 4-aminoacetophenone according to Procedure A: $^1$H NMR (DMSO-d$_6$): δ 2.00 (s, 3H), 6.83 (d, J=8.6 Hz, 1H), 7.60 (dd, J=8.5, 2.1 Hz, 1H), 7.77 (d, J=1.7 Hz, 1H), 9.99 (s, 1H), 10.91 (s, 1H); APCI–MS m/z 203 (M–H)$^-$. The title compound was prepared from 5-(1-hydroxyiminoethyly-1H-indole-2,3-dione and 4-(N-methylsulfonamido) phenylhydrazine according to Procedure G: mp>250° C.; $^1$H NMR (DMSO-d$_6$): δ 2.00 (s, 3H), 2.37 (d, J=4.9 Hz, 3H), 6.85 (d, J=8.4 Hz, 1H), 7.31 (q, J=5.0 Hz, 1H), 7.37 (dd, J=8.4, 1.8 Hz, 1H), 7.56 (d, J=8.7 Hz, 2H), 7.74 (d, J=8.8 Hz, 2H), 7.91 (d, J=1.9 Hz, 1H), 9.88 (s, 1H), 10.99 (s, 1H), 12.79 (s, 1H); APCI–MS m/z 386 (M–H)$^-$. Anal. Calcd for C$_{17}$H$_{17}$N$_5$O$_4$S: C, 52.70; H, 4.42; N, 18.08. Found: C, 52.80; H, 4.50; N, 17.90.

EXAMPLE 34

4-[1-(5-Oxazol-5-yl-2oxo-1,2-dihydro-indol-3-ylidene)-ethylamino]-benzenesulfonamide 3-(1-Dimethylaminoethylidene)-5-(oxazol-5-yl)-1,3-dihydroindol-2-one was prepared from 5-(oxazol-5-yl)-1,3-dihydroindol-2-one and N,N-dimethylacetamide dimethyl acetal according to Procedure H. Condensation of 3-(1-dimethylaminoethylidene)-5-(oxazol-5-yl)- 1,3-dihydroindol-2-one and sulfanilamide according to Procedure J provided the title compound: mp>250° C.; $^1$H NMR (DMSO-d$_6$): δ 2.51 (s, 0.8H, DMSO), 2.61 (s, 3H), 6.97 (d, J=8.2 Hz, 1H), 7.37 (s, 2H), 7.40 (dd, J=8.0, 1.5 Hz, 1H), 7.45 (d, J=8.8 Hz, 2H), 7.56 (s, 1H), 7.66 (d, J=1.2 Hz, 1H), 7.83 (d, J=8.5 Hz, 2H), 8.34 (s, 1H), 10.85 (s, 1H), 12.33 (s, 1H); APCI–MS m/z 395 (M–H)$^-$. Anal. Calcd for C$_{19}$H$_{16}$N$_4$O$_4$S.0.1 C$_2$H$_6$OS.0.6 H$_2$O: C, 55.56; H, 4.32; N, 13.50; S, 8.50. Found: C, 55.53; H, 4.32; N, 13.27; S. 8.58.

EXAMPLE 35

N,N-Dimethyl-4-[(5-oxazol-5-yl-2oxo-1,2-dihydro-indol-3-ylidenemethyl)-amino]-benzenesulfonamide 3-Methylsulfanyl-5-oxazol-5-yl-1,3-dihydro-indol-2-one was prepared from 4-oxazol -5-yl-aniline according to Procedure D: $^1$H NMR (DMSO-d$_6$): δ 10.7 (s, 1H), 8.3 (s, 1H), 7.5 (s, 3H), 6.9 (d, 1H), 4.5 (s, 1H), 2.0 (s, 3H); APCI–MS m/z 247 (M+H)$^+$. 5-Oxazol-5-yl-1,3-dihydro-indol-2-one was prepared from 3-methylsulfanyl-5oxazol-5-yl-1,3-dihydro-indol-2-one according to Procedure D: $^1$H NMR (DMSO-d$_6$): δ 10.5 (s, 1H), 8.3 (s, 1H), 7.5 (m, 3H), 6,8 (d, 1H), 3.5 (s, 2H); APCI–MS m/z 201 (M+H)$^+$. 3-Ethoxymethylene-5oxazol-5-yl-1,3-dihydro-indol-2-one was prepared from 5-oxazol-5-yl-1,3-dihydroindol-2-one according to Procedure I: $^1$H NMR (DMSO-d$_6$): δ 10.43 (s, 1H), 8.37 (s, 1H), 7.76 (s, 1H), 7.51 (m, 2H), 6.90, (d, 1H), 4.43 (q, 2H), 1.4 (t, 3H): APCI–MS m/z 255 (M–H)$^+$. The title compound was prepared in 36% yield from 3-ethoxymethylene-5-oxazol-5-yl-1,3-dihydro-indol-2-one and N,N-dimethyl4-aminobenzenesulfonamide according to Procedure J: $^1$H NMR (DMSO-d$_6$): δ 10.9 ( d, 1H), 10.8 (s, 1H), 8.8 (d, 1H), 8.4 (s, 1H), 8.0 (s, 1H), 7.7 (br d, 4H), 7.5 (m, 2H), 7.0 (d, 1H), 2.6 (s, 6H); APCI–MS m/z 409 (M–H)$^-$.

EXAMPLE 36

4-[-1-(5-Oxazol-5-yl-2oxo-1,2-dihydro-indol-3-ylidene)-hydrazino]-benzenesulfonamide (5:1 E:Z isomer mixture)

The title mixture of isomers was prepared from 5-oxazol-5-yl)-1H-indole-2,3-dione and 4-sulfonamidophenylhydrazine hydrochloride according to Procedure G: mp>250° C.; $^1$H NMR (DMSO-d$_6$): δ (5:1 ratio of Z:E isomers), E 6.97 (d, J=8.2 Hz, 1H), Z 7.00 (d, J=8.2 Hz, 1H), E 7.23 (s, 2H), Z7.25 (s, 2H), Z 7.61 (d, J=9.1Hz, 2H), E 7.61 (d, J=9.1Hz, 2H), Z 7.62 (dd, J=8.2, 1.7 Hz, 1H), Z 7.65 (s, 1H), E 7.65 (s, 1H), E 7.65 (dd, J=8.2, 1.5 Hz, 1H), Z 7.78 (d, J=8.9 Hz, 2H), E 7.81 (d, J=8.9 Hz, 2H), Z 7.90 (d, J=1.7 Hz, 1H), Z 8.40 (s, 1H), E 8.43 (s, 1H), E8.47 (d, J=1.3 Hz, 1H), E 10.83 (s, 1H), E 10.98 (s, 1H), Z 11.25 (s, 1H), Z 12.78 (s, 1H); ESI–MS m/z382 (M–H)$^-$. Anal. Calcd for C$_{17}$H$_{13}$N$_5$O$_4$S .1.2 H$_2$O.0.4 C$_2$H$_6$O: C, 50.49; H, 4.24; N, 16.54. Found: C, 50.50; H, 4.15; N, 16.56.

EXAMPLE 37

4-[-(2-Oxo-5-phenyl-1,2-dihydro-indol-3-ylidenemethyl)-amino]-benzenesulfonamide (Z-isomer)

A solution of 0.62 g (3.0 mmol) of 5-phenyl-1,3-dihydro-indol-2-one (Hewawasam and Meanwell, Tetrahedron Letters 1994, 35, 7303–6) in 10 mL of DMF was treated with 0.90 g (4.5 mmol) of DMF di-tert-butyl acetal for 2 h at rt. DMF was removed under high vaccum, and the residue was subjected to chromatography on silica gel, eluting with hexane:EtOAc (1:1), to yield 0.09 g (10%) of 3-tert-butoxymethylene-5-phenyl-1,3-dihydro-indol-2-one: $^1$H NMR (DMSO-d$_6$): δ 1.46 (s, 9H), 6.85 (d, J=8.0 Hz, 1H), 7.27 (t, J=7.3 Hz, 1H), 7.34–7.39 (m, 1H), 7.41 (d, J 7.5 Hz, 2H), 7.53 (d, J=7.5 Hz, 2H), 7.72 (s, 1H), 7.83 (s, 1H), 10.28 (s, 1H); APCI+MS m/z 316 (M+23)$^+$. Further elution with EtOAc:MeOH (98:2) gave 0.11 g (14%) of 3-dimethylaminomethylene-5-phenyl-1,3-dihydro-indol-2-one.

A solution of 0.09 g (0.31 mmol) of 5-phenyl-3-tert-butoxymethylene-1,3-dihydro-indol-2-one, 0.053 g (0.31 mmol) of sulfanilamide, and 2 drops of conc. HCl in 15 mL of ethanol was refluxed for 1 h and cooled to rt. The resulting yellow solid was isolated by filtration, washed with ethanol and dried to give 0.068 g (56%) of the title compound: $^1$H NMR (DMSO-d$_6$): δ 6.90 (d, J=8.2 Hz, 1H), 7.25 (s, 2H), 7.29 (t, J=7.5 Hz, 1H), 7.34 (dd, J=1.6, 8.2Hz, 1H), 7.43 (d, J=7.5 Hz, 2H), 7.55 (d, J=8.8 Hz, 2H), 7.64 (d, J=7.5 Hz, 2H), 7.77 (d, J=8.8 Hz, 2H), 7.99 (d, J=1.6 Hz, 1H), 8.74 (d, J=12.5 Hz, 1H), 10.62 (s, 1H), 10.76 (d, J=12.5 Hz,1H); APCI–MS m/z 390 (M–H)$^-$.

EXAMPLE 38

See Procedure K

EXAMPLE 39

2-Oxo-3-[(4-suffamoyl-phenyl)-hydrazono]-2,3-dihydro-1H-indol-5-carboxylic acid (furan-2-ylmethyl)-amide (Z-isomer)

The title compound was prepared from 2-oxo-3[-(4-sulfamoyl-phenyl)-hydrazono]-2,3-dihydro-1H-indole-5-carboxylic acid pentafluorophenyl ester and 2-aminomethylfuran according to Procedure K: mp>250° C.; $^1$H NMR (DMSO-d$_6$): δ 4.51 (d, J=5.5 Hz, 2H), 6.31 (d, J=3 Hz, 1H), 6.44 (d, J=3 Hz), 7.02 (d, J=8.3, 1H), 7.30 (s, 2H), 7.66 (m, 3H), 7.88 (m, 3H), 8.18 (s, 1H), 9.02 (br t, J=5.5 Hz, 1H), 11.4 (s, 1H), 12.8 (s, 1H); APCI–MS m/z 438 (M–H)$^-$; Anal. Calcd for C$_{20}$H$_{17}$N$_5$O$_5$S.1/2 H$_2$O: C, 53.57; H, 4.05; N, 15.62; S, 7,15. Found: C, 53.91; H, 4.01; N, 15.13; S, 6.78.

EXAMPLE 40

2-Oxo-3-[(4-sulfamoyl-phenyl)-hydrazono]-2,3-dihydro-1H-indol-5-carboxylic acid-2,6-dimethoxybenzylamide (Z-isomer)

The title compound was prepared from 2oxo-3[(4-sulfamoyl-phenyl)-hydrazono]-2,3-dihydro-1H-indole-5 carboxylic acid pentafluorophenyl ester and 2,6-dimethoxybenzylamine according to Procedure K: mp>250° C.; $^1$H NMR (DMSO-d$_6$): δ 3.76 (s, 6H), 4.43 (d, J=4.2 Hz, 2H), 6.65 (d, J=8.4 Hz, 2H), 6.91 (d, J=8.2 Hz, 1H), 7.23 (s, 2H), 7.25 (d, J=8.2 Hz, 1H), 7.56 (d, J=8.6 Hz, 2H), 7.79 (m, 3H), 8.07 (s, 1H), 8.13 (br s, 1H), 11.27 (s, 1H), 12.76 (s, 1H); APCI–MS m/z 532 (M+Na)$^+$; Anal. Calcd for C$_{24}$H$_{23}$N$_5$O$_6$S.1/2 H$_2$O: C, 55.59; H, 4.67; N, 13.51; S, 6.18. Found: C, 55.69; H, 4.64; N, 13.61; S, 6.09.

EXAMPLE 41

2-Oxo-3[(4-sulfamoyl-phenyl)-hydrazono]-2,3-dihydro-1H-indole-5-carboxylic acid (2-morpholin-4yl-ethyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and 2-N-morpholino)ethylamine according to Procedure K: mp210–212° C.; Anal. Calcd for C$_{21}$H$_{24}$N$_6$O$_5$S.1/4H$_2$O: C, 52.88; H, 5.18; N, 17.62. Found: C, 52.91; H, 5.24; N, 17.35.

EXAMPLE 42

2-Oxo-3-[(4-sulfamoyl-phenyl)-hydrazono]-2,3-dihydro-1H-indole-5-carboxylic acid (2-imidazol-1-yl-ethyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and 2-(N-imidazolo)ethylamine according to Procedure K: mp>230° C.; Anal. Calcd for C$_{20}$H$_{18}$N$_7$O$_4$S: C, 53.09; H, 4.01; N, 21.67. Found: C, 52.83; H, 4.24; N, 21.55.

EXAMPLE 43

2-Oxo-3-[-(4-sulfamoyl-phenyl)-hydrazono]-2,3-dihydro-1H-indole-5-carboxylic acid (3-imidazol-1-yl-propyl)-amide (Z-isomer)

The title compound was prepared from 2oxo-3[(4-sulfamoyl-phenyl)-hydrazono]-2,3-dihydro-1H-indole-5-carboxylic acid pentafluorophenyl ester and 3-(N-morpholino)propylamine according to Procedure K: mp>230° C.; Anal. Calcd for C$_{21}$H$_{21}$N$_7$O$_4$S.1/2H$_2$O: C, 52.93; H, 4.65; N, 20.581. Found: C, 52.93; H, 4.40; N, 20.17.

EXAMPLE 44

2-Oxo-3-[(4-sulfamoyl-phenyl)-hydrazono]-2,3-dihydro-1H-indole-5-carboxylic acid (2-methoxyethyl)-amide (Z-isomer)

The title compound was prepared from 2-oxo-3[(4-sulfamoyl-phenyl)-hydrazono]-2,3-dihydro-1H-indole-5- carboxylic acid pentafluorophenyl ester and 2-methoxyethylamine according to Procedure K: mp>230° C.; Anal. Calcd for $C_{18}H_{19}N_5O_5S$: C, 51.79; H, 4.59; N, 16.78. Found: C, 51.69; H, 4.54; N, 16.72.

EXAMPLE 45

2-Oxo-3-[(4-sulfamoyl-phenyl)-hydrazono]-2,3-dihydro-1H-indole-5-carboxylic acid (2-hydroxyethyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and 2-hydroxyethylamine according to Procedure K: mp>230° C.; Anal. Calcd for $C_{17}H_{17}N_5O_5S$: C, 50.61; H, 4.25; N, 17.36. Found: C, 50.53; H, 4.28; N, 17.27.

EXAMPLE 46

2-Oxo-3-[(4-sulfamoyl-phenyl)-hydrazono]-2,3-dihydro-1H-indole-5-carboxylic acid (3-hydroxypropyl)-amide (Z-isomer)

The title compound was prepared from 2-oxo-3-[(4-sulfamoyl-phenyl)-hydrazono]-2,3-dihydro-1H-indole-5-carboxylic acid pentafluorophenyl ester and 2-hydroxypropylamine according to Procedure K: mp>230° C.; Anal. Calcd for $C_{18}H_{19}N_5O_5S.1/3H_2O$: C, 51.06; H, 4.68; N, 16.54. Found: C, 51.07; H, 4.45; N, 16.45.

EXAMPLE 47

2-Oxo-3-[(4-sulfamoyl-phenyl)-hydrazono]-2,3-dihydro-1H-indole-5-carboxylic acid (3-hydroxy-2,2-dimethylpropyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and 3-hydroxy-2,2-dimethylpropylamine according to Procedure K: mp>230° C.; Anal. Calcd for $C_{20}H_{23}N_5O_5S$: C, 53.92; H, 5.20; N, 15.72. Found: C, 54.04; H, 5.17; N, 15.77.

EXAMPLE 48

2-Oxo-3-[(4-sulfamoyl-phenyl)-hydrazono]-2,3-dihydro-1H-indole-5-carboxylic acid (pyridin-3-ylmethyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and (3-pyridyl) methylamine according to Procedure K: mp 211–215° C.; Anal. Calcd for $C_{21}H_{18}N_6O_4S.H_2O$: C, 53.84; H, 4.30; N, 17.94. Found: C, 54.29; H, 4.03; N, 17.82.

EXAMPLE 49

2-Oxo-3-[(4-sulfamoyl-phenyl)-hydrazono]-2,3-dihydro-1H-indole-5-carboxylic acid (pyridin-4-ylmethyl)-amide (Z-isomer)

The title compound was prepared from 2-oxo-3[(4-sulfamoyl-phenyl)-hydrazono]-2,3-dihydro-1H-indole-5-carboxylic acid pentafluorophenyl ester and (4-pyridyl) methylamine according to Procedure K: mp 211–215° C.; Anal. Calcd for $C_{21}H_{18}N_6O_4S.3/4H_2O$: C, 54.36; H, 4.24; N, 18.11. Found: C, 54.41; H, 4.20; N, 18.12.

EXAMPLE 50

4-[N'-(5-Methoxy-2-oxo-1,2-dihydro-indol-3-ylidene)-hydrazino]-benzenesulfonamide (Z-isomer)

The title compound was prepared from 5-methoxy-1H-indole-2,3-dione (Gassman, et al., Journal of Organic Chemistry 1977, 42, 1344–8) and 4-hydrazinobenzenesulfonamide hydrochloride according to Procedure G: mp>250° C.; $^1$H NMR (DMSO-d$_6$): δ 3.80 (s, 3H), 6.87 (s, 2H), 7.20 (s, 1H), 7.28 (s, 2H), 7.60 (d, J=8.8 Hz, 2H), 7.81 (d, J=8.8 Hz, 2H), 10.93 (s, 1H), 12.85 (s, 1H); APCI–MS m/z 344.9 (M–H)$^-$.

EXAMPLE 51

4-[N'-(5-Amino-2-oxo-1,2-dihydro-indol-3-ylidene)-hydrazino]-benzenesulfonamide hydrochloride (Z-isomer)

The title compound was prepared from 5-amino-1H-indole-2,3-dione and 4-hydrazinobenzenesulfonamide hydrochloride according to Procedure G: $^1$H NMR (DMSO-d$_6$): δ 6.95 (d, J=8 Hz, 1H), 7.2 (d, J=8 Hz, 1H), 7.26 (s, 2H), 7.46 (s, 1H), 7.5 (d, J=8 Hz, 2H), 7.8 (d, J=8 Hz, 2H), 9.7 (br s, 3H), 11.2 (s, 1H), 12.8 (s, 1H); APCI–MS m/z 330.2 (M–H)$^-$.

EXAMPLE 52

4-[N'-(6-Ethyl-2-oxo-1,2-dihydro-indol-3-ylidene)-hydrazino]-benzenesulfonamide (Z isomer)

The title compound was prepared from 6ethyl-1H-indole-2,3-dione (Krantz and Young, 1989, U.S. Pat. No. 4,873,232) and 4-sulfonamidophenylhydrazine hydrochloride according to Procedure G in 79% yield: $^1$H NMR (DMSO-d$_6$): δ 1.16 (t, J=7.5 Hz, 3H), 2.60 (q, J=7.5 Hz, 2H), 6.74 (s, 1H), 6.89 (d, J=7.5 Hz, 1H), 7.22 (s, 2H), 7.46 (d, J=7.5 Hz, 1H), 7.50 (d, J=8.7 Hz, 1H), 7.75 (d, J=8.7 Hz, 2H), 11.02 (s, 1H), 12.70 (s, 1H); APCI–MS m/z 343 (M–H)$^-$. Anal. Calcd for $C_{16}H_{16}N_4O_3S.0.32 H_2O$: C, 54.88, H, 4.79; N, 16.00; S, 9.16. Found C, 54.81, H, 4.59; N, 16.06; S, 9.04.

EXAMPLE 53

4-[(2-Oxo-1,2-dihydro-indol-3-ylidenemethyl)-amino]-benzensulfonic acid phenyl ester (Z-isomer)

The title compound was prepared in 23% yield from 3-hydroxymethylene-1,3-dihydro-indol-2-one and phenyl 4-aminobenzenesulfonate according to Procedure J: $^1$H NMR (DMSO-d$_6$): δ 10.8 (d, 1H), 10.5 (s, 1H), 8.6 (d, 1H), 7.7 (d, 2H), 7.6 (m, 3H), 7.4 (m, 2H), 7.3 (m, 1H), 7.0 (m., 3H), 6.9 (t, 1H), 6.8 (d, 1H); APCI–MS m/z 391 (M–H)$^-$.

EXAMPLE 54

N-{4-[(2-Oxo-1,2-dihydro-indol-3-ylidenemethyl)-amino]-phenyl}sulfamide (Z-isomer)

The title compound was prepared from 3-hydroxymethylene-1,3-dihydro-indol-2-one and 4-aminophenyisulfamide according to Procedure J in 52% yield: $^1$H NMR (DMSO-d$_6$): δ 6.85 (d, J=7.5 Hz, 1H), 6.93 (t, J=7.5 Hz, 1H), 7.01 (t, J=7.5 Hz, 1H), 7.08 (s, 2H), 7.21 (d, J=8.8 Hz, 2H), 7.36 (d, J=8.8 Hz, 2H), 7.57 (d, J=7.5 Hz, 1H), 8.53 (d, J=12.7 Hz, 1H), 9.38 (s, 1H), 10.48 (s, 1H), 10.70 (d, J=12.7 Hz, 1H): APCI–MS m/z 329 (M–H)$^-$. Anal. Calcd for $C_{15}H_{14}N_4O_3S$: C, 54.54, H, 4.27; N, 16.96; S, 9.71. Found C, 54.48, H, 4.30; N, 16.90; S, 9.63.

EXAMPLE 55

4-[(6-Hydroxymethyl-2-oxo-1,2-dihydro-indol-3-ylidenemethyl)-amino]-benzenesulfonamide (Z-isomer)

A solution of 0.42 g (2.0 mmol) of 6-hydroxymethyl-3-methylsulfanyl-1,3-dihydro-indol-2-one in DMF (10 mL)

was treated with 0.32 g (2.1 mmol) of t-butyldimethylsilyl chloride and 0.15 g (2.2 mmol) of imidazole and stirred for 16 h. The solution was diluted with 50 mL of hexane and 50 mL of EtOAc, washed with brine, dried over $MgSO_4$ and concentrated to give 0.28 g (43%) of 3-methylsulfanyl-6-(t-butyldimethylsilyloxy)methyl-1,3-dihydro-indol-2-one as a clear oil which crystallised upon storage at rt: $^1H$ NMR (DMSO-$d_6$): δ 0.01 (s, 6H), 0.97 (s, 9H), 2.00 (s, 3H), 4.52 (s,1H), 4.72 (s, 2H), 6.85 (s, 1H), 6.96 (d, J=7.7 Hz, 1H), 7.25 (d, J=7.7 Hz, 1H), 10.54 (s, 1H). A solution of 0.28 g (0.86 mmol) of 3-methylsulfanyl-4-(t-butyldimethylsilyloxy)methyl-1,3-dihydro-indol-2-one in THF (10 mL) was stirred with saturated ammonium chloride solution (10 mL), and activated zinc dust (2 g) was added. The mixture was stirred 16 h at rt. The organic phase was separated, dried over $MgSO_4$ and concentrated to give 0.32 g of impure 4-(t-butyldimethylsilyloxy)methyl-1,3-dihydro-indol-2-one as a gummy white solid: $^1H$ NMR (DMSO-$d_6$): δ 0.04 (s, 6H), 0.87 (s, 9H), 3.39 (s, 2H), 4.62 (s, 2H), 6.75 (s, 1H), 6.81 (d, J=7.5 Hz, 1H), 7.10 (d, J=7.5 Hz, 1H), 10.30 (bs, 1H). A solution of 0.32 g (1.2 mmol) of 4-t-butyldimethylsilyloxy)methyl-1,3-dihydro-indol-2-one in DMF dimethylacetal (3 mL) was heated to 100° C. for 0.75 h. The excess DMF dimethylacetal was removed under high vacuum, and the resulting dark oil was chromatographed on silica gel, eluung with EtOAc/MeOH (98:2), to give 0.16 g (41%) of 3-dimethylaminomethylene-6-(t-butyldimethylsilyloxy)methyl-1,3-dihydro-indol-2-one (11:9 mixture of E and Z isomers) as a yellow solid: $^1H$ NMR (DMSO-$d_6$, peak areas normalized using the combined peak areas for δ 9.88 and 9.66 as 1H): δ 0.21 (s, 2.70H), 0.34 (s, 3.3H), 0.85 (s, 4.05H), 0.86 (s, 4.95H), 3.25 (s, 2.70H), 3.30 (s, 3.30H), 4.58 (s, 0.9H), 4.59 (s, 1.1H), 6.64–6.71 (m, 2H), 7.16 (d, J=7.7 Hz, 0.45H), 7.29 (d, J=8.3 Hz, 0.55H), 7.33 (s, 0.55H), 7.47 (s, 0.45H), 9.88 (s,0.55H) 9.96 (s, 0.45H); APCI–MS m/z 331 (M+1)$^+$. A solution of 0.334 g (1.00 mmol) of 3-dimethylamino-methylene-6-(t-butyldimethylsilyloxy)methyl-1,3-dihydro-indol-2-one in 2-methylpropanol (3 mL) was treated with 0.174 g (1.00 mmol) of sulfanilamide and 0.25 g (4.0 mmol) of acetic acid. The solution was refluxed for 3 h and cooled to rt. The resulting yellow precipitate was isolated by filtration, washed with ethanol and dried to yield 0.134 g (29%) of 6-([t-butyldimethyl-silyloxy]methyl-2-oxo-1,2-dihydro-indol-3-ylidenemethyl)-amino]-benzenesulfonamide (Z isomer).: $^1H$ NMR (DMSO-$d_6$): δ 0.05 (s, 6H), 0.87 (s, 9H), 4.65 (s, 2H), 6.81 (s, 1H), 6.85 (d, J=8.0 Hz, 1H), 7.23 (s, 2H), 7.49–7.51 (m, 3H), 7.75 (d, J=8.4 Hz, 2H), 8.56 (d, J=12.3 Hz, 1H), 10.52 (s, 1H), 10.76 (d, J=12.3 Hz. 1H); APCI–MS m/z 458 (M–H)$^-$. To a solution of 0.125 g (2.80 mmol) of 6-([t-butyldimethylsilyloxy]methyl-2-oxo-1,2-dihydro-indol-3-ylidenemethyl)-amino]-benzenesulfonamide in THF (5 mL) was added 0.27 mL of a 1 M solution of t-butylammonium fluoride in THF, and the mixture was stirred at rt for 1 h. The resulting yellow precipitate was isolated by filtration, washed with THF and dried. Chromatographic purification of the solid on silica gel, eluting with a hexane to EtOAc gradient, gave 0.053 g (55%) of the title compound: $^1H$ NMR (DMSO-$d_6$): δ 4.43 (d, J=5.8 Hz, 2H), 5.08 (t, J=5.8 Hz, 1H), 6.82 (s, 1H), 6.85 (d, J=8.2 Hz, 1H), 7.23 (s, 2H), 7.50 (d, J=7.5 Hz, 2H), 7.74 (d, J=8.7 Hz, 3H), 8.56 (d, J=12.2 Hz, 1H), 10.54 (s, 1H), 10.75 (d, J=12.1 Hz, 1H); APCI–MS m/z 345 (M–H)$^-$. Anal. Calcd for $C_{16}H_{15}N_3O_4S.0.5\ H_2O$: C, 54.43, H, 4.55; N, 11.86, S, 9.05. Found C, 54.47, H, 4.63; N, 11.66; S, 8.86.

EXAMPLE 56

4-[N'-(6-Bromo-2-oxo-1,2-dihydro-indol-3-ylidene)-hydrazino]-benzenesulfonamide (Z-isomer)

The title compound was prepared from 6-bromo-1H-indole-2,3-dione (Meth-Cohn and Goon, Tetrahedron Letters 1996, 37, 9381–4) and 4-hydrazinobenzenesulfonamide hydrochloride according to Procedure G: mp>250° C.; $^1H$ NMR (DMSO-$d_6$): δ 7.05 (s, 1H), 7.23 (d, J=8.1 Hz, 1H), 7.50 (d, J=8.1 Hz, 1H), 7.56 (d, J=8.7 Hz, 2H), 7.75 (d, J=8.7 Hz, 2H), 11.2 (s, 1H), 12.7 (s,1H); APCI–MS m/z 395 (M–H)$^-$.

EXAMPLE 57

4-[N'-(2-Oxo-6-phenoxy-1,2-dihydro-indol-3-ylidene)-hydrazino]-benzenesulfonamide (Z-isomer)

The title compound was prepared from 6-phenoxy-1H-indole-2,3-dione and 4-sulfonamidophenylhydrazine according to Procedure G in 87% yield: mp>250° C.; $^1H$ NMR (DMSO-$d_6$): δ 6.42 (d, J=2.2 Hz, 1H), 6.73 (dd, $J_1$=2.2 Hz, $J_2$=8.5 Hz, 1H), 7.17 (d, J=8 Hz, 2H), 7.25 (s, 1H), 7.28 (d, J=7.4 Hz, 2H), 7.49 (t, J=7.9 Hz, 2H), 7.73 (d, J=8.8 Hz, 2H), 7.82 (d, J=8.8 Hz, 2H), 8.25 (d, J=8.5 Hz, 2H), 10.61 (s, 1H), 10.65 (s, 1H); APCI–MS: m/z 431 (M+Na)$^+$. Anal. Calcd for $C_{20}H_{16}N_4O_4S.0.25H_2O$: C, 58.17; H, 4.03; N, 13.57; S, 7.76. Found: C, 58.45; H, 4.39; N, 13.40; S, 7.63.

EXAMPLE 58

4-[N'-(4-Ethoxy-2-oxo-1,2-dihydro-indol-3-ylidene)-hydrazino]-benzenesulfonamide (Z-isomer)

The title compound was prepared from 3-ethoxyaniline and 4-hydrazinobenzene sulfonamide hydrochloride according to Procedure C: mp>250° C.; $^1H$ NMR (DMSO-$d_6$): δ 1.43 (t, J=7.0 Hz, 3H), 4.13 (q, J=7.0 Hz, 2H), 6.50 (d, J=7.6 Hz, 1H), 6.68 (d, J=8.4 Hz, 1H), 7.15–7.21 (m, 3H), 7.46 (d, J=8.8 Hz, 2H), 7.74 (d, J=8.8 Hz, 2H), 11.03 (s, 1H), 12.78 (s, 1H); APCI–MS: m/z 359 (M–H)$^-$. Anal. Calcd for $C_{16}H_{16}N_4O_4S$: C, 53.32; H, 4.47; N, 15.55; S, 8.90. Found: C, 53.21; H, 4.50; N, 15.66; S, 8.85.

EXAMPLE 59

N-[2-(2-Hydroxyethoxy)ethyl]-4-[7-oxo-6,7-dihydro-1-thia-3,6-diaza-as-indacene-8-ylidenemethyl)-amino]benzenesulfonamide (Z-isomer)

The title compound was prepared from 4-amino-N-(2-(2-hydroxyethoxy)ethyl)-benzenesulfonamide (see Example 84) and 8-ethoxymethylene-6,8-dihydro-1-thia-3,6-diaza-as-indacen-7-one according to Procedure J: $^1H$ NMR (DMSO-$d_6$): δ 2.88 (q, J=6.0 Hz, 2H), 3.31 (t, J=5.0 Hz, 2H), 3.36 (t, J=5.8 Hz, 2H), 3.42 (t, J=5.1 Hz, 2 Hz), 4.5 (br s, 1H), 7.10 (d, J=8.4 Hz, 1H), 7.59 (d, J=8.8 Hz, 2H), 7.60 (t, J=6.0 Hz, 1H), 7.77 (d, J=8.7 Hz, 2H), 7.81 (d, J=8.6 Hz, 1H), 8.07 (d, J=12.2 Hz, 1H), 9.25 (s, 1H), 10.91 (s, 1H), 11.16 (d, J=12.2 Hz, 1H); APCI–MS m/z 459 (M–H)$^-$. Anal. Calcd for $C_{20}H_{20}N_4O_5S_2.H_2O$: C, 50.20; H, 4.63; N, 11.71. Found: C, 50.06; H, 4.59; N, 11.68.

EXAMPLE 60

N-[2-(2-Hydroxyethyl]-4-[7-oxo-6,7-dihydro-thia-3,6-diaza-as-indacene-8-ylidenemethyl)-amino]benzenesulfonamide (Z-isomer)

The title compound was prepared in 51% yield from N-(2-hydroxyethyl)-4-aminobenzene sulfonamide and 8-ethoxymethylene-6,8-dihydro-1-thia-3,6-diaza-as-indacen-7-one according to Procedure J: $^1H$ NMR (DMSO-$d_6$): δ 11.18 (d,1H), 10.9 (s, 1H), 9.25 (s, 1H), 8.06 (d, 1H), 7.8 (d, 1H), 7.76 (d, 2H), 7.58 (d, 2H), 7.52 (t, 1H), 7.1 (d, 1H), 4.66 (t, 1H), 3.35 (q, 2H), 2.76 (q, 2H); APCI–MS m/z 415 (M–H)$^-$.

EXAMPLE 61

N-Methyl-4-[N'-4-(4-methyl-5-nitro-2-oxo-1,2-dihydro-indol-3-ylidene)-hydrazino]-benzenesulfonamide (Z-isomer)

4-Methyl-5-nitro-1H-indole-2,3-dione was prepared from 3-methyl-4-nitroaniline according to Procedure A: $^1$H NMR (DMSO-d$_6$): δ 11.5 (s, 1H), 8.2 (d, 1H), 6.8 (d, 1H), 2.7 (s, 3H); APCI–MS m/z 205 (M–H)$^-$. The title compound was prepared in 84% yield from 4-methyl-5-nitro-1H-indole-2,3-dione and 4-sulfonamidophenylhydrazine hydrochloride according to Procedure G: $^1$H NMR (DMSO-d$_6$): δ 13.0 (s, 1H), 11.6 (s, 1H), 7.9 (d,1H), 7.7 (d, 2H), 7.6 (d, 2H), 7.3 (q, 1H), 6.9 (d, 1H), 2.8 (s, 3H), 2.4 (d, 3H); APCI–MS m/z 388 (M–H)$^-$.

EXAMPLE 62

4-[N'-(7-Oxo-6,7-dihydro-3H-pyrrolo[3,2-e]indazol-8-ylidene)-hydrazino]-benzenesulfonamide (Z isomer)

The title compound was prepared from 3,6-dihydro-pyrrolo[3,2-e]indazole-7,8-dione (Cuny, et al., Chemie Berichte 1981, 114, 1624–35) and 4- sulfonamidophenylhydrazine hydrochloride according to Procedure G in 8% yield: $^1$H NMR (DMSO-d$_6$): δ 7.02 (d, J=8.7 Hz, 1H), 7.28 Z (s, 2H), 7.51 (d, J=8.6 Hz, 2H), 7.68 (d, J=8.8 Hz, 1H), 7.82 (d, J=8.7 Hz, 2H), 8.34 (s, 1H), 10.98 (s, 1H), 12.90 (s, 1H), 13.20 (s, 1H); APCI–MS m/z 356 (M)$^-$. Anal. Calcd for C$_{15}$H$_{12}$N$_6$O$_3$S.1.46 H$_2$O.0.2 EtOAc: C, 47.41, H, 4.16; N, 20.99; S, 8.01. Found C, 47.40, H, 3.70; N, 21.00; S, 7.85.

EXAMPLE 63

4-[N'-(7-Oxo-6,7-dihydro-1H-pyrrolo[2,3-g]indazol-8-ylidene)-hydrazino]-benzenesulfonamide (mixture of E and Z isomers)

The title compound was prepared from isatin 1,6-dihydropyrrolo[2,3-g]indazole-7,8-dione (Lichtenthaler and Cuny, Heterocycles 1981, 15. 1053–9) and 4-sulfonamidophenyl-hydrazine hydrochloride according to Procedure G in 76% yield: $^1$H NMR (DMSO-d$_6$): δ 6.82 Z (d, J=8.3 Hz, 1H), 6.87 E (d, J=8.5 Hz, 1H), 7.24 E (s, 2H), 7.27 Z (s, 2H), 7.43 E (d, J=8.6 Hz, 2H), 7.73 Z (d, J=8.3 Hz, 1H), 7.78 Z (d, J=8.8 Hz, 2H), 7.85 E (d, J=8.8 Hz, 2H), 7.89 E (d, J=8.5 Hz, 1H), 7.89 Z (d, J=8.5 Hz, 2H), 8.12 Z (s, 1H), 8.56 E (s, 1H), 10.67 E (s, 1H), 11.20 Z (s, 1H), 12.86 Z (s, 1H), 13.27 E (s, 1H), 13.27 Z (s, 1H), 14.27 E (s, 1H); APCI–MS m/z 355 (M–H)$^-$. Anal. Calcd for C$_{15}$H$_{12}$N$_6$O$_3$S: C, 50.56, H, 3.39; N, 23.58; S, 9.00. Found C, 50.65, H, 3.40; N, 23.59; S, 8.97.

EXAMPLE 64

4-[N'-(7-Oxo-6,7-dihydro-3H-1,2,3,6-tetraaza-as-indacen-8-ylidene)-hydrazino]-benzenesulfonamide (mixture of E and Z isomers)

1,6-Dihydro-1,2,3,6-tetraaza-as-indacene-7,8-dione was prepared according to Procedure A in 56% yield: $^1$H NMR (DMSO-d$_6$): δ 6.93 (d, J=8.6 Hz, 1H), 8.32 (d, J=8.6 Hz, 1H), 11.14 (s, 1H); APCI–MS m/z 189 (M+1)$^+$. Condensation of 1,6-dihydro-1,2,3,6-tetraaza-as-indacene-7,8-dione with 4-sulfonamidophenylhydrazine hydrochloride according to Procedure G gave the title compound in 15% yield: $^1$H NMR (DMSO-d$_6$): δ 7.06 Z (d, J=8.4 Hz, 1H), 7.24 E (d, J=8.4 Hz, 1H), 7.30 Z (s, 2H), 7.30 E (s, 2H), 7.55 E (d, J=8.5 Hz, 2H), 7.82 Z (d, J=8.5 Hz, 2H), 7.82 E (d, J=8.5 Hz, 1H), 7.90 E (d, J=8.7 Hz, 2H), 7.90 Z (d, J=8.8 Hz, 2H), 7.98 Z (d, J=8.4 Hz, 1H), 10.86 E (s, 1H), 11.35 Z (s, 1H), 12.87 Z (s, 1H), 12.95 E (s, 1H), 16.00 Z (s, 1H), 16.25 E (s, 1H); APCI–MS m/z 356 (M–H)$^-$. Anal. Calcd for C$_{14}$H$_{11}$N$_7$O$_3$S.H$_2$O: C, 44.80, H, 3.49; N, 26.12; S, 8.54. Found C, 44.72, H, 3.46; N, 26.05; S, 8.48.

EXAMPLE 65

4-[N'-(1-Chloro-7-oxo-6,7-dihydro-3H-pyrrolo[3,2-]indazol-8-ylidene)-hydrazino]-benzenesulfonamide (Z-somer)

1-Chloro-3,6-dihydro-pyrrolo[3,2-e]indazole-7,8-dione was prepared from 5-amino-3-chloroindazole according to Procedure A in 38% yield: $^1$H NMR (DMSO-d$_6$): δ 7.08 (d, J=7.9 Hz, 1H), 7.92 (d, J=7.9 Hz, 1H), 10.95 (s, 1H), 13.70 (s, 1H). Condensation of 1-chloro-3,6-dihydro-pyrrolo[3,2-e]indazole-7,8-dione and 4-sulfonamidophenylhydrazine hydrochloride according to Procedure G gave the title compound in 45% yield: $^1$H NMR (DMSO-d$_6$): δ 7.11 (d, J=8.8 Hz, 1H), 7.26 (s, 2H), 7.51 (d, J=8.8 Hz, 1H), 7.64 (d, J=8.8 Hz, 2H), 7.82 (d, J=8.8 Hz, 2H), 11.17 (s, 1H), 13.25 (s, 1H), 13.41 (s, 1H); APCI–MS m/z 389/391 (M–H)$^-$. Anal. Calcd for C$_{15}$H$_{11}$ClN$_6$O$_3$S: C, 44.86, H, 3.06; N, 20.93; S, 7.98. Found C, 45.02, H, 3.31; N, 20.92; S, 7.77.

EXAMPLE 66

4-[N'-(1,7-Dioxo-2,3,6,7-tetrahydro-1H-2,6-diaza-as-indacen-8-ylidene)-hydrazino]-H-methyl-benzenesulfonamide (Z-isomer)

A solution of 16.2 g (100 mmol) of 6-aminophtnalimide, 9.6 g (100 mmol) of methanesulfonic acid, and 4.0 g of 10% Pd/C in 140 mL of TFA was hydrogenated overnight at 50 psi. The catalyst was filtered off and and the filtrate concentrated on a rotary evaporator. The residue was diluted with 70 mL of ice water, adjusted to pH 8 with K$_2$CO$_3$, and chilled in an ice bath. The resulting solid was filtered to give 6.7 g of a 5:4 ratio of 5-amino:6-amino lactam isomers. Recrystallization from hot ethanol/water afforded 1.45 g of undesired isomer. The filtrate was preabsorbed onto silica gel and chromatographed with TEA:MeOH:methylene chloride (1:2:47). The resulting solid was slurried in methylene chloride/MeOH and filtered to afford a low yield of 5-amino-2,3-dihydro-isoindol-1-one: $^1$H NMR (DMSO-d$_6$): δ 4.13 (s, 2H), 5.67 (s, 2H), 6.55 (dd, J=8.7, 1.9 Hz, 1H), 6.55 (d, J=1.9 Hz, 1H), 7.25 (d, J=8.7 Hz, 1H), 7.83 (s, 1H); APCI–MS m/z 149 (M+H)$^+$.

2,6-Dihydro-1H-2,6-diaza-as-indacene-3,7,8-trione was prepared from 5-amino-2,3-dihydro-isoindol-1-one according to Procedure X: $^1$H NMR (DMSO-d$_6$): δ 4.46 (s, 2H), 6.94(d, J=8.1 Hz, 1H), 7.80(d, J=8.0 Hz, 1H), 8.51 (s, 1H), 11.28 (s, 1H); APCI–MS m/z 201 (M–H)$^-$. The title compound was prepared from 2,6-dihydro-1H-2,6-diaza-as-indacene-3,7,8-trione and 4-(N-methylsulfonamido)phenylhydrazine according to Procedure G: mp>250° C.; $^1$H NMR (DMSO-d$_6$): δ 2.37 (d, J=4.9 Hz, 3H), 4.56 (s, 2H), 6.99 (d, J=7.9 Hz, 1H), 7.31 (q, J=5.2 Hz, 1H), 7.55 (d, J=8.1 Hz, 1H), 7.60 (d, J=8.8 Hz, 2H), 7.72 (d, J=8.7 Hz, 2H), 8.50 (s, 1H), 11.35 (s, 1H), 12.70 (s, 1H); APCI–MS m/z 384 (M–H)$^-$. Anal. Calcd for C$_{17}$H$_{15}$N$_5$O$_4$S.0.75 H$_2$O: C, 51.19; H, 4.17; N, 17.56. Found: C, 51.29; H, 4.15; N, 17.47.

EXAMPLE 67

N-3-Hydroxy-2,2-dimethyl-propyl)-C-{4-[(7-oxo-6,7-dihydro-1-thia-3,6-diaza-as-indacen-8-ylidenemethyl)-amino]-phenyl}-methanesulfonamide (Z-isomer)

A solution of 3.16 g (30.6 mmol) of 3-amino-2,2-dimethylpropanol in 10 mL of CH$_2$Cl$_2$ was added at once to a solution of 2.40 g (10.2 mmol) of 4-nitrophenylmethanesulphonyl chloride (Lee, et al., Journal of the American Chemical Society 1987, 109, 7472–7; Macor, et al., Tetrahedron Letters 1992, 33, 8011–4) in 40 mL of $CH_2Cl_2$. The mixture was stirred at rt for 15 min, the solvent was removed in vacuo and the residue was redissolved in 50 mL of EtOAc. The solution was washed with three 50-mL portions of 1.0 N HCl and concentrated in vacuo. Purification of the residue by flash chromatography on silica gel (hexane/EtOAc 1:1) afforded N-3-hydroxy-2,2-dimethyl-propyl)-(4-nitrophenyl)-methanesulfonamide as a white solid (0.84 g, 27%): $^1H$ NMR (DMSO-$d_6$): δ 0.74 (s, 6H), 2.78 (d, J=6.4 Hz, 2H), 3.11 (d, J=5.3 Hz, 2H), 4.47 (t, J=5.3 Hz, 1H), 4.52 (s, 2H), 7.02 (t, J=6.4 Hz, 1H), 7.65 (d, J=8.8 Hz, 2H), 8.25 (d, J=8.8 Hz, 2H); APCI–MS: m/z 301 (M–H)⁻. A mixture of 0.66 g (2.2 mmol) of N-(3-hydroxy-2,2-dimethyl-propyl)-(4-nitro-phenyl)-methanesulfonamide and ~0.06 g Pd/C 10% in 50 mL of MeOH was shaken on a Parr hydrogenator for 3.5 h. The catalyst was removed via filtration, and 0.273 mL (3.28 mmol) of conc. HCl was added. The solvent was removed in vacuo, and the solid residue was redissolved in 20 mL of EtOH and added to 0.486 g (1.98 mmol) of 8-dimethylaminomethylene-6,8-dihydro-1-thia-3,6-diaza-as-indacen-7-one. The mixture was heated to reflux for 4.5 h and cooled to ambient tempurature. The solid was collected by vacuum filtration, washed with water, and dried in a vacuum oven at 70° C. to afford the title compound as a yellow solid (0.66 g, 70%): mp 229–230° C. (dec); $^1H$ NMR (DMSO-$d_6$): δ 0.74 (s, 6H), 2.73 (d, J=6.4 Hz, 2H), 3.08 (d, J=5.3 Hz, 2H), 4.27 (s, 2H), 4.43 (t, J=5.3 Hz, 1H), 6.84 (t, J=6.4 Hz, 1H), 7.09 (d, J=8.3 Hz, 1H), 7.37 (d, J=8.5 Hz, 2H), 7.42 (d, J=8.5 Hz, 2H), 7.77 (d, J=8.3 Hz, 1H), 8.03 (d, J=12.3 Hz, 1H), 9.24 (s, 1H), 10.84 (s, 1H), 11.04 (d, J=12.3 Hz, 1H); ESI–MS: m/z 471 (M–H)⁻. Anal. Calcd for $C_{22}H_{24}N_4O_4S_2 \cdot 0.5 H_2O$: C, 54.87; H, 5.23; N, 11.63; S, 13.32. Found: C, 54.90; H, 5.26; N, 11.68; S, 13.25.

EXAMPLE 68

N-Methyl-C-{4-N'-(2-oxo-2,3-dihydro-pyrrolo[3,2f-]quinolin-1-ylidene)-hydrazino]-phenyl}-methanesulfonamide (Z-somer)

2-Hydroxyimino-N-quinolin-6-yl-acetamide was prepared in 61% yield from 6-aminoquinoline according to Procedure A: $^1H$ NMR (DMSO-$d_6$): δ 12.4 (s, 1H), 10.8 (s, 1H), 9.0 (d, 1H), 8.8 (d, 1H), 8.7 (s, 1H), 8.2 (s, 2H), 7.81 (m, 1H), 7.78 (s, 1H); $C_{11}H_9N_3O_2$: APCI–MS m/z 216 (M+H)⁺. To a 1-L 3-neck round bottom flask was placed a magnetic stir bar and 110 mL of concentrated sulfuric acid. The flask was fitted with a thermometer to monitor the temperature of the reaction. The sulfuric acid was heated to 100° C. followed by slow addition of 2-hydroxyimino-N-quinolin-6-yl-acetamide (26.0 g, 0.121 mol). Heat to the reaction was maintained for approximately 1 h. The flask was removed from the heat source, and the reaction was poured slowly and carefully onto a mixture of 1 Kg of ice and 200 g of sodium carbonate. The residual reaction mixture in the reaction vessel was washed out with an additional 40 mL of cold water. The resulting aqueous slurry was stirred for about 1 h and filtered. The solid was washed thoroughly with water, filtered, and air dried to yield 7.31 g (31%) of 3-H-pyrrolo[3,2-f]quinoline-1,2-dione: $^1H$ NMR (DMSO-$d_6$): δ 11.1 (s, 1H), 8.8 (d, 1H), 8.7 (d, 1H), 8.2 (d, 1H), 7.6 (m, 1H), 7.4 (d, 1H); APCI–MS m/z 197 (M–H)⁻. The title compound was prepared in 77% yield from 3-H-pyrrolo[3,2-f]quinoline-1,2-dione and 4-hydrazinophenylmethane sulfonamide according to Procedure G: $^1H$ NMR (DMSO-$d_6$): δ 13.1 (s, 1H), 11.5 (s, 1H), 9.3 (d, 1H), 8.9 (d, 1H), 8.0 (d, 1H), 7.9 (m, 1H), 7.6 (d, 1H), 7.6(d, 2H), 7.4 (d, 2H), 6.9(d, 1H), 4.3 (s, 2H), 2.55 (d, 3H); APCI–MS m/z 396 (M+H)⁺.

EXAMPLE 69

N-(1H-Indazol-6-yl)-4-[(7-oxo-6,7-dihydro-1-thia-3, 6-diaza-as-indacen-8-ylidenemethyl)-amino]-benzenesulfonamide (Z-isomer)

The title compound was prepared in 16% yield from 8-ethoxymnethylene-6,8-dihydro-1-thia-3,6-diaza-as-indacen-7-one and 4-amino-N-(1H-indazol-6-yl)-benzenesulfonamide according to Procedure J: $^1H$ NMR (DMSO-$d_6$): δ 12.9 (s, 1H), 11.1 (d, 1H), 10.9 (s, 11H), 10.4 (s, 1H), 9.3 (s, 1H), 8.1(d, 1H), 8.0 (s, 1H), 7.8 (d, 1H), 7.8 (d, 2H), 7.7 (d, 1H), 7.6 (d, 2H), 7.3 (s, 1H), 7.1 (d, 1H), 6.9 (d, 1H); APCI–MS m/z 487 (M–H)⁻.

EXAMPLE 70

4-[(7-Oxo-6,7-dihydro-1-thia-3,6-diaza-as-indacen-8-ylidenemethyl)-amino]-N-thiazol-2-yl-benzenesulfonamide (Z-isomer)

The title compound was prepared in 33% yield from 8ethoxymethylene-6,8-dihydro-1-thia-3,6-diaza-as-indacen-7-one and 4-amino-N-(thiazol-2-yl)-benzenesulfonamide according to Procedure J: $^1H$ NMR (DMSO-$d_6$): δ 12.7 (s, 1H), 11.2 (d, 1H), 10.9 (s, 1H), 9.3 (s, 1H), 8.1 (d, 1H), 7.8 (t, 3H), 7.6 (d, 2H), 7.3 (d, 1H), 7.2 (d, $_1$H), 6.8 (d, 1H); APCI–MS m/z 456 (M+H)⁺ and 454 (M–H)⁻.

EXAMPLE 71

N-(Amino-imino-methyl)-4-[(7-oxo-6,7-dihydro-1-thia-3,6-diaza-as-indacen-8-ylidenemethyl)-amino]-benzenesulfonamide (Z-isomer)

The title compound was prepared in 26% yield from 8ethoxymethylene-6,8-dihydro-1-thia-3,6-diaza-as-indacen-7-one and 4-amino-N-(aminoimino-methyl)-benzenesulfonamide according to Procedure J: $^1H$ NMR (DMSO-$d_6$): δ 11.2 (d, 1H), 10.9 (s, 1H), 9.3 (s, 1H), 8.1 (d, 1H), 7.85 (d, 1H), 7.8 (d, 2H), 7.5 (d, 2H), 7.4 (d, 1H), 7.3 (d, 1H), 6.5 (d, 1H), 5.7 (s, 1H); $C_{17}H_{14}N_6O_3S_2$: APCI–MS m/z 415 (M+H)⁺.

EXAMPLE 72

See Procedure J

EXAMPLE 73

8-(2,2-Dioxo-1,3-dihydro-benzo[c]thiophene-5-ylamino-methylene)-6,8-dihydro-1-thia-3,6-diaza-as-indacen-7-one (Z-isomer)

The title compound was prepared in 37% yield from 8-ethoxymethylene-6,8-dihydro-1-thia-3,6-diaza-as-indacen-7-one and 2,2-dioxo-1,3-dihydrobenzo[c] thiophene-5-ylamine according to Procedure J: $^1H$ NMR (DMSO-$d_6$): δ 11.11 (d,1H), 10.89 (s, 1H), 9.27 (s, 1H), 8.06 (d, 1H), 7.82 (d, 1H), 7.47 (m, 2H), 7.13 (d, 1H), 6.98 (d, 1H), 6.5 (m, 2H); APCI–MS m/z 384 (M+H)⁺.

EXAMPLE 74

{4-[-(7-Oxo-6,7-dihydro-1-thia-3,6-diaza-as-indacen-8-ylidenemethyl)-amino]-phenyl}-methanesulfonamide (Z-isomer)

The title compound was prepared in 25% yield from 8-ethoxymethylene-6,8-dihydro-1-thia-3,6-diaza-asindacen-7-one and 4-aminophenylmethane sulfonamide according to Procedure J: $^1$H NMR (DMSO-d$_6$): δ 11.1 (d,1H), 10.9 (s, 1H), 9.3 (s, 1H), 8.1 (d, 1H), 7.8 (d, 1H), 7.5 (q, 4H), 7.2 (d, 1H), 6.9 (s, 2H), 4.2 (s, 2H); APCI–MS m/z 387 (M+H)$^+$.

EXAMPLE 75

N-Allyl-C-{4-[(7-oxo-6,7-dihydro-1-thia-3,6-diaza-as-indacen-8-ylidenemethyl)-amino]-phenyl}-methansulfonamide (Z-isomer)

The title compound was prepared in 26% yield from 8ethoxymethylene-6,8-dihydro-1-thia-3,6-diaza-as-indacen-7-one and N-allyl-4-aminophenylmethane sulfonamide according to Procedure J: $^1$H NMR (DMSO-d$_6$): δ 11.1 (d, 1H), 10.9 (s, 1H), 9.3 (s, 1H), 8.1 (d, 1H), 7.8 (d, 1H), 7.5 (q, 4H), 7.3 (t, 1H), 7.1 (d, 1H), 5.8 (m, 1H), 5.2 (d, 1H), 5.1 (d, 1H), 4.4 (s, 2H), 3.6 (t, 2H); APCI–MS m/z 427 (M+H)$^+$.

EXAMPLE 76

8-(4-Methylsulfonylmethyl-phenylamino-methylene)-6,8-dihydro-1-thia-3,6-diaza-as-indacen-7-one (Z-isomer)

The title compound was prepared in 66% yield from 8-ethoxymethylene-6,8-dihydro-1-thia-3,6-diaza-as-indacen-7-one and 4-methylsulfonylmethylaniline according to Procedure J: $^1$H NMR (DMSO-d$_6$): δ 11.1 (d, 1H), 11.0 (s, 1H), 9.3 (s, 1H), 8.1 (d, 1H), 7.8 (d, 1H), 7.5 (q, 4H), 7.1 (d, 1H), 4.45 (s, 2H), 2.9 (s, 3H); APCI–MS m/z 384 (M–H)$^-$.

EXAMPLE 77

N-(3-Hydroxy-2,2-dimethyl-propyl)-4-[(7-oxo-6,7-dihydro-1-thia-3,6-diaza-as-indacen-8-ylidenemethyl)-amino]-benzenesulfonamide (Z-isomer)

The title compound was prepared from 8-ethoxymethylene-6,8-dihydro-1-thia-3,6-diaza-as-indacen-7-one and 4-amino-N-(3-hydroxy-2,2-dimethyl-propyl)benzenesulfonamide according to Procedure J: mp>250° C.; $^1$H NMR (DMSO-d$_6$): δ 0.74 (s, 6H), 2.52 (d, J=6.7 Hz, 2H), 3.06 (bs, 2H), 4.43 (bs, 1H), 7.10 (d, J=8.3 Hz, 1H), 7.32 (t, J=6.7 Hz, 1H), 7.58 (d, J=8.8 Hz, 2H), 7.77 (d, J=8.8 Hz, 2H), 7.81 (d, J=8.3 Hz, 1H), 8.07 (d, J=12.2 Hz, 1H), 9.26 (s, 1H), 10.91 (s, 1H), 11.16 (d, J=12.3 Hz, 1H); APCI–MS: m/z 457 (M–H)$^-$. Anal. Calcd for $C_{21}H_{22}N_4O_4S_2$: C, 55.01: H, 4.84; N, 12.22; S, 13.98. Found: C, 54.90; H, 4.86; N, 12.25; S, 13.94.

EXAMPLE 78

4-[(7-Oxo-6,7-dihydro-1-thia-3,6-diaza-as-indacen-8-ylidenemethyl)-amino]-N-(3-trifluoromethyl-phenyl)benzenesulfonamide (Z-isomer)

The title compound was prepared in 29% yield from 8-ethoxymethylene-6,8-dihydro-1-thia-3,6-diaza-as-indacen-7-one and N-(3-trifluoromethylphenyl)-4-aminobenzenesulfonamide according to Procedure J: $^1$H NMR (DMSO-d$_6$): δ 11.2 (d, 1H), 10.9 (s, 1H), 10.7 (s, 1H), 9.3 (s, 1H), 8.1 (d, 1H), 7.8 (m, 3H), 7.5 (m, 4H), 7.1 (d, 1H); APCI–MS m/z 515 (M–H)$^-$.

EXAMPLE 79

4-[(7-Oxo-6,7-dihydro-1-thia-3,6diaza-as-indacen-8-ylidenemethyl)-amino]-pyrimidin-2-yl-benzenesulfonamide (Z-isomer)

The title compound was prepared in 29% yield from 8ethoxymethylene-6,8-dihydro-1-thia-3,6-diaza-as-indacen-7-one and 4-amino-N-pyrimidin-2-yl-benzenesulfonamide according to Procedure J: $^1$H NMR (DMSO-d$_6$): δ 11.18 (d, 1H), 10.94 (s, 1H), 9.28 (s, 1H), 8.52 (d, 1H) 8.08 (d, 1H), 7.99 (d, 1H), 7,84 (d, 1H), 7.6 (d, 1H), 7.13 (d, 1H), 7.06 (m, 1H), 7.01 (m, 1H),; APCI–MS m/z 449 (M–H)$^-$.

EXAMPLE 80

N-(5-Methyl-[1,3,4]thiadiazol-2-yl)-4-(7oxo-6,7-dihydro-1-thia-3,6-diaza-as-indacen-8-ylidenemethyl)-amino]-benzenesulfonamide (Z-isomer)

The title compound was prepared in 36% yield from 8-ethoxymethyiene-6,8-dihydro-1-thia-3,6-diaza-as-indacen-7-one and 4-amino-N-(5-methyl[1,3,4]thiadiazol-2-yl)-benzenesulfonamide according to Procedure J: $^1$H NMR (DMSO-d$_6$): δ 11.2 (d, 1H), 10.9 (s, 1H), 9.3 (s, 1H), 8.1 (d, 1H), 7.8 (m, 3H), 7.6 (d, 2H), 7.1 (d, 1H); ESI–MS m/z 469 (M–H)$^-$.

EXAMPLE 81

N-Acetyl-4-[(7-oxo-6,7-dihydro-1-thia-3,6-diaza-as-indacen-4-ylidenemethyl)-amino]-benzenesulfonamide (Z-isomer)

The title compound was prepared in 26% yield from 8-ethoxymethylene-6,8-dihydro-1-thia-3,6-diaza-as-indacen-7-one and N-acetyl-4-aminobenzenesulfonamide according to Procedure J: $^1$H NMR (DMSO-d$_6$): δ 12.0 (s, 1H), 11.2 (d, 1H), 10.9 (s, 1H), 8.1 (d, 1H), 7.9 (m, 3H), 7.6 (d, 2H), 7.1 (d, 1H), 2.0(s, 3H); ESI–MS m/z 413 (M–H)$^-$.

EXAMPLE 82

N-Benzoyl-4-[(7-oxo-6,7-dihydro-1-thia-3,6-diaza-as-indacen-8-ylidenemethyl)-amino]-benzenesulfonamide (Z-isomer)

The title compound was prepared in 25% yield from 8-ethoxymethylene-6,8-dihydro-1-thia-3,6-diaza-as-indacen-7-one and N-benzoyl-4-aminobenzenesulfonamide according to Procedure J: $^1$H NMR (DMSO-d$_6$): δ 12.5 (br s, 1H), 11.2 (d, 1H), 10.9 (s, 1H), 9.3 (s, 1H), 8.1 (d, 1H), 8.0 (d, 2H), 7.9 (t, 3H), 7.65 (t, 3H), 7.5 (t, 2H), 7.2 (d, 1H); ESI–MS m/z 475 (M–H)$^-$.

EXAMPLE 83

N-Methyl-4-[N'-(7-oxo-6,7-dihydro-1-thia-3,6-diaza-as-indacen-8-ylidene)-hydrazino]benzenesulfonamide (Z-isomer)

6H-1-Thia-3,6-diaza-as-indacene-7,8-ione was prepared from 6-aminobenzothiazole according to Procedure A: $^1$H NMR (DMSO-d$_6$): δ 7.10 (d, J=8.4 Hz, 1H), 8.31 (d, J=8.5 Hz, 1H), 9.35 (s, 1H), 11.19 (s, 1H); ESI–MS m/z 204 (M)$^-$. The title compound was prepared from 6H-1-thia-3,6-diaza-as-indacene-7,8-dione and 4-sulfonamidophenylhydrazine hydrochloride according to Procedure G: mp>260° C.; $^1$H NMR (DMSO-d$_6$): δ 2.39 (d, J=5.1 Hz, 3H), 7.12 (d, J=8.4 Hz, 1H), 7.32 (q, J=5.1 Hz, 1H), 7.63 (d, J=8.8 Hz, 2H), 7.76 (d, J=8.7 Hz, 2H), 7.99 (d, J=8.6 Hz, 1H), 9.30 (s, 1H), 11.26 (s, 1H), 12.69 (s, 1H); APCI–MS m/z 387 (M)$^-$. Anal. Calcd for $C_{16}H_{13}N_5O_3S_2$.0.33 H$_2$O: C, 48.85; H, 3.50; N, 17.80; S, 16.30. Found: C, 48.89; H, 3.40; N, 17.67; S, 16.23.

EXAMPLE 84

N-[2-(2-Hydroxy-ethoxy)-ethyl-N-methyl-4-[(7-oxo-6,7-dihydro-1-thia-3,6-diaza-as-indacen-8-ylidenemethyl)-amino]-benzenesulfonamide (Z-isomer)

To a solution of 3.3 g (31 mmol) of 2-(2-aminoethoxy) ethanol in 30 mL of MeOH was added 7.0 g (30 mmol) of N-acetylsulfanilyl chloride, followed by 3.3 g (33 mmol) of TEA. The reaction mixture was stirred for 30 min at rt and then acidified with 5 mL (60 mmol) of concentrated HCl and stirred at reflux for 75 min. After cooling, the mixture was diluted with 40 mL of water and made basic with solid NaHCO$_3$. MeOH was removed on a rotary evaporator, and the residual aqueous solution was extracted with four 50-mL portions of EtOAc. The combined extracts were dried over Na$_2$CO$_3$, and the solvent was removed on a rotary evaporator to give 4-amino-N-(2-(2-hydroxyethoxy)ethyl)-benzenesulfonamide as a viscous oil (7.5 g, 96%): $^1$H NMR (DMSO-d$_6$): δ 2.77 (q, J=6.0 Hz, 2H), 3.30 (t, J=4.9 Hz, 2H), 3.31 (t, J=6.5 Hz, 2H), 3.41 (q, J=5.2 Hz, 2H), 4.54 (t, J=5.5 Hz, 1H), 5.89 (s, 2H), 6.57 (d, J=8.7 Hz, 2H), 7.10 (t, J=7.37 (d, J=8.6 Hz, 2H); ESI–MS m/s 259 (M−H)$^-$. To a solution of 0.63 g (2.4 mmol) of 4-amino-N-(2-(2-hydroxyethoxy)ethyl)-benzenesulfonamide in 10 mL of THF was added 0.10 g (2.5 mmol) of 60% sodium hydride. The mixture was stirred for 1 h at rt, 1 mL of DMSO and ~0.2 mL (~3 mmol) of methy iodide were added to the resulting suspension. The reaction mixture was stirred 2 h at rt and then poured into 15 mL of half saturated NaCl solution and extracted with 30 mL of EtOAc. The organic solution was dried with MgSO$_4$ and concentrated on a rotary evaporator. The residue was chromatographed on silica gel with EtOAc to give 4-amino-N-(2-(2-hydroxyethoxy)ethyl)-N-methyl-benzenesulfonamide as an oil (0.43 g, 65%): $^1$H NMR (DMSO-d$_6$): δ 2.59 (s, 3H), 2.96 (t, J=5.9 Hz, 2H), 3.36 (t, J=5.2 Hz, 2H), 3.43 (t, J=5.2 Hz, 2H), 3.47 (t, J=5.9 Hz, 2H), 4.55 (t, J=5.4 Hz, 1H), 5.99 (s, 2H), 6.59 (d, J=8.7 Hz, 2H), 7.34 (d, 8.8 Hz, 2H); APCI–MS m/z 297 (M+Na)$^+$. The title compound was prepared from 4-amino-N-(2-(2-hydroxyethoxy)ethyl)-N-methyl-benzenesulfonamide and 8-ethoxymethylene-6,8-dihydro-1-thia-3,6-diaza-as-indacen-7-one according to Procedure J: mp 165° C.; $^1$H NMR (DMSO-d$_6$): δ 2.71 (s, 3H), 3.11 (t, J=5.6 Hz, 2H), 3.37 (t, J=5.0 Hz, 2H), 3.44 (dt, J=5.1, 5.0 Hz, 2H), 3.52 (t, J=5.6 Hz, 2H), 4.56 (br t, J=5.2 Hz, 1H), 7.10 (d, J=8.4 Hz, 1H), 7.61 (d, J=8.7 Hz, 2H), 7.75 (d, J=8.7 Hz, 2H), 7.81 (d, J=8.5 Hz, 1H), 8.06 (d, J=12.0 Hz, 1H), 9.25 (s, 1H), 10.91 (s, 1H), 11.16 (d, J=12.0 Hz, 1H); APCI–MS m/z 474 M$^-$. Anal. Calcd for C$_{21}$H$_{22}$N$_4$O$_5$S$_2$.H$_2$O: C, 51.21; H, 4.91; N, 11.37. Found: C, 51.18; H, 4.88; N, 11.33.

EXAMPLE 85

N-(2-{2-[2-(2-Methoxy-ethoxy)ethoxy]-ethoxy}-ethyl)-4-[(7-oxo-6,7-dihydro-1-thia-3,6-diaza-as-indacen-8-ylidenemethyl)-amino]-benzenesulfonamide (Z-isomer)

A solution of 2.3 g (6.3 mmol) of toluene-4-sulfonic acid 2-{2-[2-(2-methoxy-ethoxy)-ethoxy]-ethoxy}ethyl ester and ~4 mL (~60 mmol) of ammonium hydroxide in 10 mL of ethanol was stirred overnight at ~60° C. The solvent was removed on a rotary evaporator, and the residue was sequentially redissolved in ethanol and concentrated several times. The residue was then dissolved in ethanol, treated with ~1.5 mL of TEA and concentrated on a rotary evaporator. This residue was dissolved in 10 mL of THF, and 1.4 g (6.0 mmol) of 4-N-acetylsulfanilyl chloride and 1 mL (7 mmol) of TEA were added. The reaction mixture was stirred 1.5 h at rt and then 30 min at reflux. The solution was concentrated onto silica gel and chromatographed with an EtOAc to 5% MeOH/EtOAc gradient to give 4-N-(2-{2-[2-(2-methoxy-ethoxy)-ethoxy]-ethoxy}-ethyl)sulfonamidophenyl]acetamide as an oil (1.92 g, 79%): $^1$H NMR (DMSO-d$_6$): δ 2.05 (s, 3H), 2.83 (q, J=5.9 Hz, 2H), 3.19 (s, 3H), 3.30–3.48 (m, 14H), 7.52 (t, J=5.8 Hz, 1H), 7.68 (d, J=9.0 Hz, 2H), 7.72 (d, J=8.8 Hz, 2H), 10.27 (s, 1H); APCI–MS m/z 403 (M−H)$^-$. A solution of 1.9 g (4.7 mmol) of N-[4-(2-{2-[2-(2-methoxy-ethoxy)ethoxy]-ethoxy}-ethylsulfamoyl)-phenyl]-acetamide and 0.45 g (4.7 mmol) of methanesulfonic acid in 15 mL of ethanol was stirred at ~70° C. for 1 d. Excess TEA was added and the solvent was removed on a rotary evaporator. The residue was applied to a short column of silica gel and eluted with EtOAc to give 4-N-2-{2-[2-(2-methoxyethoxy)ethoxy]ethoxy}ethyl)-sulfonamidoaniline as an oil (1.2 g, 70%): $^1$H NMR (DMSO-d$_6$): δ 2.76 (q, J=6.0 Hz, 2H), 3.20 (s, 3H), 3.32 (t, J=6.2 Hz, 2H), 3.37–3.48 (m, 12H), 5.88 (s, 2H), 6.56 (d, J=8.6 Hz, 2H), 7.11 (t, J=6.0 Hz, 1H), 7.37 (d, J=8.7 Hz, 2H); APCI–MS m/z 361 (M−H)$^-$. The title compound was prepared from 4-(N-(2-{2-[2-(2-methoxyethoxy)ethoxy]ethoxy}ethyl)sulfonamidoaniline and 8-ethoxymethylene-6,8-dihydro-1-thia-3,6-diaza-as-indacen-7-one according to Procedure J: mp 158–159° C.; $^1$H NMR (DMSO-d$_6$): δ 2.87 (dt, J=5.6, 5.6 Hz, 2H), 3.17 (s, 3H), 3.33–3.38 (m, 4H), 3.38–3.47 (m, 10H), 7.10 (d, J=8.3 Hz, 1H), 7.58 (d, J=8.7 Hz, 2H), 7.63 (t, J=5.7 Hz, 1H), 7.77 (d, J=8.7 Hz, 2H), 7.81 (d, J=8.5 Hz 1H), 8.06 (br d, J=8.9 Hz, 1H), 9.25 (s, 1H), 10.91 (s, 1H), 11.16 (br d, J=10.8 Hz, 1H); APCI–MS m/z 561 (M−H)$^-$. Anal. Calcd for C$_{25}$H$_{30}$N$_4$O$_7$S$_2$.0.33 H$_2$O: C, 52.81; H, 5.43; N, 9.85. Found: C, 52.81; H, 5.29; N, 9.82.

EXAMPLE 86

4-[N'-5,6-Dimethyl-2-oxo-1,2-dihydro-indol-3-ylidene)-hydrazino]-benzenesulfonamide (Z isomer)

The title compound was prepared from 5,6-dimethyl-1H-indole-2,3-dione and 4-sulfonamidophenylhydrazine hydrochloride according to Procedure G in 32% yield: $^1$H NMR (DMSO-d$_6$): δ 2.22 (s, 3H), 2.24 (s, 3H), 6.72 (s, 1H), 7.23 (s, 2H), 7.36 (s, 1H), 7.52 (d, J=8.8 Hz, 2H), 7.77 (d, J=8.8 Hz, 2H), 10.93 (s, 1H), 12.71 (s, 1H), APCI–MS m/z 343 (M−H)$^-$. Anal. Calcd for C$_{16}$H$_{16}$N$_4$O$_3$S: C, 55.80, H, 4.68; N, 16.27; S, 9.31. Found C, 55.78, H, 4.74; N, 16.37; S, 9.22.

EXAMPLE 87

N-{6-Hydroxy-3-[(4-methylsulfamoylmethyl-phenyl)-hydrazono]-2-oxo-2,3-dihydro-1H-indol-5-yl}-acetamide (Z isomer)

Condensation of N-(6-hydroxy-2,3-dioxo-2,3-dihydro-1H-indol-4-yl)acetamide and 4-hydrazino-N-methyl-benzylsulfonamide hydrochloride according to Procedure G gave the title compound in 4% yield: $^1$H NMR (DMSO-d$_6$): δ 2.04 (s, 3H), 2.51 (d, J=4.8 Hz, 3H), 4.24 (s, 2H), 6.45 (s, 1H), 6.84 (t, J=4.8 Hz), 1H), 7.30 (s, 4H), 7.82 (s, 1H), 9.12 (s, 1H), 10.20 (s, 1H), 10.77 (s, 1H), 12.50 (s, 1H); APCI–MS m/z 416 (M−H)$^-$.

EXAMPLE 88

4-[N'-(6-Chloro-5-methoxy-2-oxo-1,2-dihydroindol-3-ylidene)-hydrazino]benzene-sulfonamide (Z-isomer)

The title compound was prepared from 6-chloro-5-methoxy-1H-indole-2,3-dione (Pajouhesh et al., Journal of Pharmaceutical Sciences 1983, 72, 318–21) and 4-sulfonamido-phenylhydrazine hydrochloride according to Procedure G: mp>250° C.; $^1$H NMR (DMSO-d$_6$): δ 3.88 (s, 3H), 6.93 (s, 1H), 7.25 (s, 2H), 7.35 (s, 1H), 7.59 (d, J=8.8 Hz, 2H), 7.76 (d, J=8.8 Hz, 2H), 10.97 (s, 1H), 12.78 (s, 1H);

APCI–MS: m/z 379 (M–H)⁻. Anal. Calcd for $C_{15}H_{13}N_4O_4ClS$: C, 47.31; H, 3.44; N, 14.71; Cl, 9.31 S, 8.42. Found: C, 47.57; H, 3.71; N, 14.93; Cl, 9.11 S, 8.17.

EXAMPLE 89

4-[N'-(5-Hydroxy-isopropyl-2-oxo-1,2-dihydro-indol-3-ylidene)-hydrazino]-benzenesulfonamide (Z-isomer)

5-Hydroxy-6-isopropyl-1H-indole-2,3-dione was prepared from 3-isopropyl-4-hydroxyaniline according to Procedure A: $^1$H NMR (DMSO-d$_6$): δ 1.12 (d, J=6.8 Hz, 6H), 3.21 (septet, J=6.9 Hz, 1H), 6.62 (s, 1H), 6.82 (s, 1H), 9.51 (s, 1H), 10.61 (s, 1H); ESI–MS m/z 204 (M–H)⁻. The title compound was prepared from 5-hydroxy-6-isopropyl-1H-indole-2,3-dione and 4-sulfonamidophenylhydrazine hydrochloride according to Procedure G: mp>250° C.; $^1$H NMR (DMSO-d$_6$): δ 1.12 (d, J=7.0 Hz, 6H), 3.21 (septet, J=6.8 Hz, 1H), 6.62 (s, 1H), 6.97 (s, 1H), 7.21 (s, 2H), 7.45 (d, J=8.9 Hz, 2H), 7.75 (d, J=8.7 Hz, 2H), 9.11 (s, 1H), 10.70 (s, 1H), 12.74 (s, 1H); ESI–MS m/z 373 (M–H)⁻. Anal. Calcd for $C_{17}H_{18}N_4O_4S$: C, 54.53; H, 4.85; N, 14.96; S, 8.56. Found: C, 54.37; H, 4.95; N, 14.84; S, 8.48.

EXAMPLE 90

4-[N'-(2-Methyl-6-oxo-5,6-dihydro-3-oxa-1,5-diaza-s-indacen-7-ylidene)-hydrazino]benzenesulfonamide (Z isomer)

N-(6-Hydroxy-2,3-dioxo-2,3-dihydro-1H-indol-4-yl)acetamide was prepared from 6-amino-2-methylbenzoxazole (Heleyova, et al., Collection of Czechoslovakian Chemical Communications 1996, 61, 371–80) according to Procedure A in 12% overall yield. Condensation of N-(6-hydroxy-2,3-dioxo-2,3-dihydro-1H-indol-4-yl)acetamide and 4-sulfonamidophenylhydrazine hydrochloride according to Procedure G gave the title compound in 6% yield: $^1$H NMR (DMSO-d$_6$): δ 2.55 (s, 3H), 7.13 (s, 1H), 7.23 (s, 2H), 7.57 (d, J=8.8 Hz, 2H), 7.76 (d, J=8.8 Hz, 2H), 7.78 (s, 1H), 11.12 (s, 1H), 12.67 (s, 1H); APCI–MS m/z 370 (M–H)⁻. Anal. Calcd for $C_{16}H_{15}N_5O_4S$: C, 51.75, H, 3.53; N, 18.86; S, 8.86. Found C, 51.50. H, 3.61; N, 18.69; S, 8.49.

EXAMPLE 91

4-[N'-(5-Acetyl-2-oxo-2,5,6,7-tetrahydro-1H-pyrrolo[2,3-f]indol-3-ylidene)-hydrazino]-benzenesulfonamide (Z-isomer)

5-Acetyl-1,5,6,7-tetrahydro-pyrrolo[2,3-f]indole-2,3-dione was prepared from 1-acetyl-5-aminoindoline according to Procedure A in 90% yield: mp>250° C.; $^1$H NMR (DMSO-d$_6$): δ 2.11 (s,3H), 3.16 (t, J=8.4 Hz, 2H), 4.06 (t, J=8.4 Hz, 2H), 6.78 (s, 1H), 8.02 (s, 1H), 10.87 (s, 1H); APCI–MS: m/z 229 (M–H)⁻. Anal. Calcd for $C_{12}H_{10}N_2O_3 \cdot 0.3\ H_2O$: C, 61.17; H, 4.53; N, 11.89. Found: C, 60.91; H, 4.62; N, 12.10. The title compound was prepared from 5-acetyl-1,5,6,7-tetrahydro-pyrrolo[2,3-f]indole-2,3-dione and 4-sulfonamidophenylhydrazine hydrochloride according to Procedure G in 53% yield: mp>250° C.; $^1$H NMR (DMSO-d$_6$):d2.13 (s,3H), 3.13 (t, J=8.4 Hz, 2H), 4.06 (t, J=8.4 Hz, 2H), 6.79 (s, 1H), 7.22 (s, 2H), 7.48 (d, J=8.7 Hz, 2H), 7.76 (d, J=8.7 Hz, 2H), 8.24 (s, 1H), 10.96 (s, 1H), 12.78 (s, 1H); APCI–MS: m/z 422 (M+Na)⁺. Anal. Calcd for $C_{18}H_{17}N_5O_4S$: C, 54.13; H, 4.29; N, 17.53; S, 8.03. Found: C, 53.85; H, 4.23; N, 17.28; S, 7.89.

EXAMPLE 92

4-[N'-(6-Oxo-5,6-dihydro-[1,3]-dioxolo[4,5-f]indol-7-ylidene)-hydrazino]-benzenesulfonamide (Z-isomer)

The title compound was prepared from 5H-[1,3]dioxolo[4,5-f]indole-6,7-dione (Lackey and Stembach, Synthesis 1993, 993–7) and 4-sulfonamidophenylhydrazine hydrochloride in 55% yield as an orange crystalline solid following Procedure G: mp>220° C.; $^1$H NMR (DMSO-d$_6$): δ 12.63 (s, 1H), 10.89 (s, 1H), 7.73 (d, J=7 Hz, 2H), 7.50 (d, J=7 Hz, 2H), 7.22 (s, 2H), 7.13 (s, 1H), 6.56 (s, 1H), 6.00 (s, 2H), Anal. Calcd for $C_{15}H_{12}N_4O_5S$: C, 50.00; H, 3.36; N, 15.55. Found: C, 50.08; H, 3.35; N, 15.49.

EXAMPLE 93

4-[N'-(2-Oxo-2,5,6,7-tetrahydro-1H-pyrrolo[2,3-f]indol-3-ylidene)-hydrazino]-benzenesulfonamide hydrobromide (Z-isomer)

A solution of 0.10 g (0.44 mmol) of 5-acetyl-1,5,6,7-tetrahydro-pyrrolo[2,3-f]indole-2,3-dione in 3 mL of conc. HBr was heated to 100° C. for 18 h. The mixture was cooled to ambient temperature, diluted with 10 mL of water and filtered. The filtrate was concentrated in vacuo and added to a solution of 0.05 g (0.2 mmol) 4-sulfonamidophenylhydrazine hydrochloride in 5 mL of EtOH, The mixture was heated to 80° C. for 1 h and cooled to ambient tempurature. The resulting solid was collected by vacuum filtration, washed with water and dried in a vacuum oven at 70° C. to afford the title compound as a tan solid (0.026 g, 17%): mp>250° C.; $^1$H NMR (DMSO-d$_6$): δ 3.17 (t, J=7.8 Hz, 2H), 3.69 (t, J=7.8 Hz, 2H), 6.96 (s, 1H), 7.25 (s, 2H), 7.52 (s, 1H), 7.57 (d, J=8.8 Hz, 2H), 7.77 (d, J=8.8 Hz, 2H), 10.65 (bs, 2H), 11.24 (s, 1H), 12.73 (s, 1H); APCI–MS: m/z 356 (M–H)⁻. Anal. Calcd for $C_{16}H_{15}N_5O_3S \cdot 0.9\ HBr \cdot 0.5\ H_2O$: C, 43.75; H, 3.88; N, 15.94; S, 7.30. Found: C, 44.01; H, 4.14; N, 15.70; S, 7.12.

EXAMPLE 94

C-{4-[N'-(4,6-Dichloro-5-methoxy-2-oxo-1,2-dihydro-indol-3-ylidene)-hydrazino]-phenyl}-N-methyl-benzenesulfonamide (Z-isomer)

4,6-Dichloro-5-methoxy-1H-indole-2,3-dione was prepared from 3,5-dichloro-4,6-hydroxyaniline according to Procedure A in 91% yield: $^1$H NMR (DMSO-d$_6$): δ 3.81 (s, 3H), 6.98 (s, 1H), 11.26 (s, 1H); APCI–MS m/z 244/246/248 (M–H)⁻. Condensation of 4,6-dichloro-5-methoxy-1H-indole-2,3-dione with 4-hydrazino-N-methyl-benzylsulfonamide according to Procedure G gave the title compound in 59% yield: $^1$H NMR (DMSO-d$_6$): δ 2.58 (d, J=4.7 Hz, 3H), 3.84 (s, 3H), 4.33 (s, 2H), 6.93 (q, J=4.7 Hz, 1H), 6.99 (s, 1H), 7.41 (d, J=8.5 Hz, 2H), 7.51 (d, J=8.5 Hz, 2H), 11.31 (s, 1H), 12.99 (s, 1H); APCI–MS m/z 441/443 (M–H)⁻. Anal. Calcd for $C_{17}H_{16}Cl_2N_4O_4S$: C, 46.06; H, 3.64; Cl, 15.99; N, 12.64; S, 7.23. Found C, 45.80; H, 3.55; Cl, 16.20; N, 12.57; S, 7.11.

EXAMPLE 95

4-[N'-(4-Chloro-5-hydroxy-6-methyl-2-oxo-1,2-dihydro-indol-3-ylidene)-hydrazino]-benzenesulfonamide (Z-isomer)

4-Chloro-5-hydroxy-6-methyl-1H-indole-2,3-dione was prepared from 3-chloro-4-hydroxy-5-methyl aniline according to Procedure A and employing flash chromatography (hexanes:EtOAc 1:1) to isolate the desired isomer: $^1$H NMR (DMSO d$_6$): δ 2.35 (s, 3H), 6.67 (s, 1H), 9.17 (s, 1H), 10.81 (s, 1H); APCI–MS: m/z 210 (M–H)⁻. Anal. Calcd for $C_9H_6NO_3Cl$: C, 51.08; H, 2.85; N, 6.62; Cl, 16.75. Found: C, 51.20; H, 2.90; N, 6.67; Cl, 16.85. The title compound was prepared from 4-chloro-5-hydroxy-6-methyl-1H- indole-2,3-dione and 4-sulfonamidophenylhydrazine hydrochloride according to Procedure G in 95% yield: mp>250° C.; $^1$H NMR (DMSO-d$_6$): δ 2.26 (s, 3H), 6.69 (s, 1H), 7.28 (s, 1H), 7.57 (d, J=8.8 Hz, 2H), 7.82 (d, J=8.8 Hz, 2H), 8.84 (s, 1H), 11.02 (s, 1H), 13.00 (s, 1H); APCI–MS: m/z 379 (M–H)$^-$. Anal. Calcd for C$_{15}$H$_{13}$N$_4$O$_4$ClS: C, 47.31; H, 3.44; N, 14.71; Cl, 9.31; S, 8.42. Found: C, 47.20; H, 3.47; N, 14.64; Cl, 9.41; S, 8.32.

EXAMPLE 96

4-[N'-(5-Hydroxy -4,6-dimethyl-2-oxo-1,2-dihydro-indol-3-ylidene)-hydrazino]-benzenesulfonamide (Z-isomer)

5-Hydroxy-4,6-dimethyl-1H-indole-2,3-dione was prepared from 4-hydroxy-3,5-dimethylaniline according to Procedure A. The title compound was prepared from 5-hydroxy-4,6-dimethyl-1H-indole-2,3-dione and 4-sulfonamidophenylhydrazine hydrochloride according to Procedure G: mp>250° C.; $^1$H NMR (DMSO-d$_6$): δ 2.18 (s, 3H), 2.47 (s, 3H), 6.50 (s, 1H), 7.22 (s, 2H), 7.44 (d, J=8.7 Hz, 2H), 7.77 (d, J=8.7 Hz, 2H), 7.99 (s, 1H), 10.78(s, 1H), 12.98 (s, 1H); APCI–MS: m/z 359 (M–H)$^-$. Anal. Calcd for C$_{16}$H$_{16}$N$_4$O$_4$S.0.25 H$_2$O: C, 52.67; H, 4.56; N, 15.35; S, 8.79. Found: C, 52.69; H, 4.47; N, 15.33; S, 8.87.

EXAMPLE 97

3-(1H-Indazol-5-yl-amino-ethylene)-1,3-dihydro-indol-2-one (Z-isomer)

The title compound was prepared in 68% yield from 3-hydroxymethylene-1,3-dihydro-indol-2-one and 5-aminoindazole according to Procedure J: $^1$H NMR (DMSO-d$_6$): δ 13.1 (s, 1H), 10.8 (d, 1H), 10.4 (s, 1H), 8.6 (d, 1H), 8.0 (s, 1H), 7.8 (s, 1H), 7.6 (m, 2H), 7.4 (m, 1H), 7.0 (m, 2H), 6.8 (d, 1H); C$_{16}$H$_{12}$N$_4$O$_2$: ESI–MS m/z 275 (M–H)$^-$.

EXAMPLE 98

3-(1H-Indazol-6-ylimino-methylene)-1,3-dihydro-indol-2-one (Z-isomer)

The title compound was prepared in 79% yield from 3-hydroxymethylene-1,3-dihydro-indol-2-one and 6-aminoindazole according to Procedure J: $^1$H NMR (DMSO-d$_6$): δ 13.02 (s, 1H), 10.86 (d, 1H), 10.51 (s, 1H), 8.7 (d, 1H) ) 8.0 (s, 1H), 7.74 (d, 1H), 7.63 (d, 1H) 7.51 (s, 1H), 7.15 (dd, 1H), 7.02 (m, 1H), 6.94 (m, 1H), 6.85 (d, 1H); ESI–MS m/z 275 (M–H)$^-$.

EXAMPLE 99

See Procedure G

EXAMPLE 100

N-Methyl-4-[(5-oxazol-5-yl-2-oxo-1,2-dihydro-indol-3-ylidenemethyl)-amino]-phenylmethanesulfonamide (Z-isomer)

The title compound was prepared in 56% yield from ethoxymethylene-5-oxazol-5-yl-1,3-dihydro-indol-2-one and N-methyl-4-aminophenylmethanesulfonamide hydrochloride according to Procedure J: $^1$H NMR (DMSO-d$_6$): δ 10.72 (d,1H), 10.67 (s, 1H), 8.71 (d, 1H), 8.37 (s, 1H), 7.43–7.34 (m, 7H), 6.89 (m, 2H), 4.28 (s, 2H), 2.54 (s, 3H); APCI–MS m/z 409 (MH)$^-$.

EXAMPLE 101

8-(3H-Benzotriazol-5-ylaminomethylene)-6,8-dihydro-1-thia-3,6-diaza-as-indacene-7-one (Z-isomer)

The title compound was prepared in 54% yield from 8-ethoxymethylene-6,8-dihydro-1-thia-3,6-diaza-as-indacen-7-one and 5-aminobenzotriazole according to Procedure J: $^1$H NMR (DMSO-d$_6$): δ 11.18 (d,1H), 10.9 (s, 1H), 9.23 (s, 1H), 8.12 (d, 1H), 7.96 (s, 1H), 7.78 (d, 1H), 7.48 (s, 1H), 7.1 (d, 1H); APCI–MS m/z 333 (M–H)$^-$.

EXAMPLE 102

4-[N'-2-Oxo-2,3-dihydropyrrolo[3,2-f]quinolin-1-ylidene)hydrazino]-benzenesulfonamide (Z-isomer)

The title compound was prepared in 24% yield from 3-H-pyrrolo[3,2-f]quinoline-1,2-dione and 4-hydrazinobenzene sulfonamide hydrochloride according to Procedure G: $^1$H NMR (DMSO-d$_6$) δ 13.12 (s, 1H), 11.64 (s, 1H), 9.32 (d, 1H), 9.01 (d, 1H), 8.13 (d, 1H), 7.9 (m, 1H), 7.83 (d, 2H), 7.69 (d, 2H), 7.62 (s, 1H), 7.33 (s, 2H). APCI–MS m/z 368 (MH)$^+$.

EXAMPLE 103

2-Oxo-3-(4-sulfamoyl-phenylamino-methylene)-2,3-dihydro-1H-indole-5-carboxylic acid isobutyl ester (Z-isomer)

3-Methylthio-2-oxo-2,3-dihydro-1H-indole-5-carboxylic acid isobutyl ester was prepared in 59% yield from isobutyl 4-aminobenzoate according to Procedure D: $^1$H NMR (DMSO-d$_6$): δ 0.93 (d, J=6.6 Hz, 6H), 1.93 (s, 3H), 1.98 (septet, J=6.6 Hz, 1H), 4.02 (m, 2H), 4.62 (s, 1H), 6.92 (d, J=8.2 Hz, 1H), 7.79 (s, J=1H), 7.86 (d, J=8.2 Hz, 1H), 10.91 (s, 1H); ESI–MS m/z 302 (M+23)$^-$. Zinc reduction of 3-methylthio-2oxo-2,3-dihydro-1H-indole-5-carboxylic acid isobutyl ester according to Procedure δ provided 2-oxo-2,3-dihydro-1H-indole-5-carboxylic acid isobutyl ester in 99% yield: $^1$H NMR (DMSO-d$_6$): δ 0.93 (d, J=6.6 Hz, 6H), 1.97 (septet, J=6.6 Hz, 1H), 3.53 (s, 2H), 3.99 (d, J=6.6 Hz, 2H), 6.88 (d, J=8.2 Hz, 1H), 7.75 (s, J=1H), 7.82 (d, J=8.2 Hz, 1H), 10.72 (s, 1H); ESI–MS m/z 256 (M+23)$^+$. Conversion of 2-oxo-2,3-dihydro-1H-indole-5-carboxylic acid isobutyl ester to 3-[(dimethylamino)methylene]-2-oxo-2,3-dihydro-1H-indole-5-carboxylic acid isobutyl ester (mixture of E and Z isomers) was accomplished in 75% yield according to Procedure G: $^1$H NMR (DMSO-d$_6$): δ 0.94 Z (d, J=8.8 Hz, 6H), 0.94 E (d, J=8.8 Hz, 6H), 1.94–2.01 Z and E (m, 2H), 3.30 Z (s, 6H), 3.32 E (s, 6H), 3.97–3.99 Z and E (m, 4H), 6.75 Z (d, J=8.2 Hz, 1H), 6.83 E (d, J=8.2 Hz, 1H), 7.47 E (s, 1H), 7.53 Z (d, J=8.2 Hz, 1H), 7.59 E (d, J=8.2 Hz, 1H), 7.73 Z (s, 1H), 7.88 Z (s, 1H), 7.98 E (s, 1H), 10.34 Z (bs, 1H), 10.44 E (bs, 1H); ESI–MS m/z 289 (M+1)$^+$. The title compound was prepared in 66% yield from 3-[(dimethylamino)methylene]-2-oxo-2,3-dihydro-1H-indole-5-carboxylic acid isobutyl ester and 4-aminobenzenesulfonamide hydrochloride according to Procedure J: $^1$H NMR (DMSO-d$_6$): δ 0.96 (d, J=6.6 Hz. 6H), 2.01 (septet, J=6.6 Hz, 1H), 4.04 (d, J=6.6 Hz, 2H), 6.93 (d, J=8.2 Hz, 1H), 7.26 (s, 2H), 7.60 (d, J=8.7 Hz, 2H), 7.71 (dd, J=1.6, 8.2 Hz, 1H), 7.76 (d, J=8.7 Hz, 2H), 8.27 (s, 1H), 8.86 (d, J=12.5 Hz, 1H), 10.83 (d, J=12.5 Hz, 1H), 10.95 (s, 1H); APCI–MS m/z 414 (M–H)$^-$. Anal. Calcd for C$_{20}$H$_{21}$N$_3$O$_5$S: C, 57.82; H, 5.09; N, 10.11; S, 7.72. Found C, 57.91; H, 5.16; N, 10.02; S, 7.65.

EXAMPLE 104

4-[(7Oxo-6,7-dihydro-1-thia-3,6diaza-as-indacen-8-ylidenemethyl)amino]-N-pyridinyl-4-yl-methyl benzenesulfonamide (Z-isomer)

To a 250 ml round bottom flask was added 50 ml of dry pyridine, 4-(aminomethyl)pyridine (10.4 g, 50.0 mmol) and a magnetic stir bar. The mixture was stirred and cooled to 0° C. under nitrogen followed by the addition of N-acetylsulfanilyl chloride (12.8 g, 55.0 mmol). The resultant mixture was stirred at 0° C. under nitrogen for 5 min. and the reaction was allowed to warm to rt and stirred for 16 h. The reaction mixture was concentrated to a thick residue and poured onto about 500 g of ice and water. The residue in the flask was rinsed into the ice and water with 25 ml of MeOH to precipitate the N-acetyl sulfanilamide. The resultant precipitate was filtered, washed with excess water and dried under vacuum at 50° C. The solid was suspended in 75 ml of 1N hydrochloric acid and heated to 100° C. until all starting material had been consumed. The reaction mixture was cooled and neutralized with ammonium hydroxide. The precipatate was filtered and dried under vacuum at 50° C. to yield 5.78 g, 43.9% of 4-amino-N-(4-aminomethylpyridinyl)-benzenesulfonamide: $^1$H NMR (DMSO-$d_6$): δ 8.42 (d, 2H), 7.76 (t, 1H), 7.39 (d, 2H), 7.22 (d, 2H), 6.56 (d, 2H), 5.91 (s, 2H), 3.89 (d, 2H); APCI–MS m/z 264 (MH)$^+$. The title compound was prepared in 33% yield from 8-ethoxymethylene-6,8-dihydro-1-thia-3,6diaza-as-indacen-7-one and 4-amino-N-4-aminomethylpyridinyl)-benzenesulfonamide according to Procedure J: $^1$H NMR (DMSO-$d_6$): δ 11.15 (d, 1H), 10.9 (s, 1H), 9.24 (s, 1H), 8.44 (d, 2H), 8.24 (m, 1H), 8.05 (d, 1H), 7.81 (d, 1H), 7.76 (m, 2H), 7.56 (d, 2H), 7.24 (d, 2H), 7.1 (d, 1H), 4.01 (d, 2H); APCI–MS m/z 464 (MH)$^+$.

Pharmaceutical Formulation and Doses

The compounds of the present invention can be administered in such oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.1 to 100 mg/kg of body weight per day, and particularly 1 to 10 mg/kg of body weight per day. Oral dosage units will generally be administered in the range of from 1 to about 250 mg and more preferably from about 25 to 250 mg. The daily dosage for a 70 kg mammal will generally be in the range of about 70 mg to 7 grams of a compound of formula I or II.

While the dosage to be administered is based on the usual conditions such as the physical condition of the patient, age, body weight, past medical history, route of administrations, severity of the conditions and the like, it is generally preferred for oral administration to administer to a human. In some cases, a lower dose is sufficient and, in some cases, a higher dose or more doses may be necessary. Topical application similarly may be once or more than once per day depending upon the usual medical considerations. Advantageously, compounds of the present invention may be administered in a single daily dose, or the total daily dosage may be administered in divided doses of two, three or four times daily. The compounds of the invention can be prepared in a range of concentrations for topical use of 0.5 to 5 mg/ml of suitable solvent. A preferred volume for application to the scalp is 2 ml, resulting in an effective dosage delivered to the patient of 1 to 10 mg. For treatment of chemotherapy-induced alopecia, administration 1 to 2 times prior to chemotherapy administration would be preferred, with additional applications administered as needed. A similar regimen can be pursued for treatment of alopecia induced by radiation therapy. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging. adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, steaylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.01 to 99.5%, more particularly, 0.5 to 90% of a compound of the formula (II) in combination with a pharmaceutically acceptable carrier.

Parenteral administration can be effected by utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous oleaginous medium and sterilizing the suspension or solution.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ester as for example flavored aqueous solution, while elixirs are prepared through myristyl palmitate or mixtures thereof.

Topical formulations of the present invention may be presented as, for instance, ointments. creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The preferred pharmaceutical compositions are those in a form suitable for oral administration, such as tablets and liquids and the like and topical formulations.

Biological Data

The compounds of the present invention have valuable pharmacologic properties. Different compounds from this class are particularly effective at inhibiting the CDK1 and CDK2 enzymes at concentrations which range from 0.0001 to 1 $\mu$M and additionally show specificity relative to other kinases. Substrate phosphorylation assays were carried out as follows:

CDK1 and CDK2

Cyclin dependent protein kinase assays utilized the peptides Biotin-aminohexyl-AAKAKKTPKKAKK and Biotin-aminohexyl-ARRPMSPKKKA-NH$_2$ as phosphoryl group acceptors. CDK1 and CDK2 were both expressed utilizing a baculovirus expression system and were partially purified to comprise 20–80% of total protein, with no detectable competing reactions present. Typically, assays were performed by incubating either enzyme (0.2–10 nM), with and without inhibitor, one of the two peptide substrates (1–10 nM), [$\gamma$-$^{32}$P]ATP (1–20 nM), and 10–20 mM Mg$^{2+}$ for periods of time generally within the range 10–120 min.

Reactions were terminated with 0.2–2 volumes of either 20% acetic acid or 50–100 mM EDTA buffered to pH 7 (substrate consumption<20%). The buffer employed in enzyme assays was either 30 mM HEPES 7.4 containing 0.15 M NaCl and 5% DMSO, the buffer 50 mM MOPS 7.0 containing 0.15 M NaCl and 5% DMSO, or the buffer 100 mM HEPES pH 7.5 containing 0.1 mg /mL BSA and 5% DMSO. Inhibitors were diluted in 100% DMSO prior to addition into the assay. Detection of peptide phosphorylation was accomplished by scintillation counting following either collection of peptide onto phosphocellulose filters (for reactions stopped with acetic acid), collection of peptide in wells of 96 well plates coated with Streptavidin (Pierce) (reactions were stopped with EDTA), or addition of Avidin coated Scintillant impregnated beads (Scintillation Proximity Assays from Amersham, reactions were stopped with EDTA). Counts detected by any of these methodologies minus the appropriate background (assays with additional 40 mM EDTA or lacking peptide substrate) were assumed to be proportional to the reaction initial rates, and IC50s were determined by a least squares fit to the equation CPM= $V_{max}*(1-([I]/(K+[I])))+nsb$, or $pIC_{50}$s were determined by a fit to the equation CPM=nsb+$(V_{max}-nsb)/(1+(x/10^x-pIC50))$, where nsb are the background counts.

UL97

UL97 was produced as a GST fusion protein from a baculovirus vector expressed in sf9 cells as described by He (He, et al., Journal of Virology 1997, 71, 405–11). UL97 was assayed as a protein kinase using $^{32}P$ transfer from ATP to histone $H_2B$ with detection of radiolabeled histone bound to phosphocellulose. Assay mixes for testing inhibitors of UL97 activity contained 2 mM $[\gamma^{32}P]$-ATP, 15 mM histone $H_2B$, 50 mM sodiumCHES, pH 9.5, 1 M NaCl, 2 mM dithiothreitol and 10 mM $MgCl_2$. Inhibitors were dissolved in diluted DMSO to give a final DMSO concentration in the reaction of 1% DMSO. After incubation at 20° C., the reactions were terminated by addition of 10 volumes of 75 mM phosphoric acid, 30 mM ATP, 1 mM EDTA, then were spotted onto phosphocellulose filters and washed four times with 75 mM phosphoric acid. Radioactivity was determined by liquid scintillation counting.

Src/Lck

The peptide substrates used in Src and Lck assays were biotin-aminohexyl-EEIYGEF-$NH_2$ (Src) and biotin-aminohexyl-EAIYGVLFAKKKK-$NH_2$ (Lck). The src and lck proteins were purified to homogeneity from a baculovirus expression system and preactivated before adding to assay mixtures. The maximum activation was achieved by incubating concentrated enzyme (10–30 mM) on ice for 40 min in the presence of 1 mM ATP and 10 mM $MgCl_2$ in 100 mM HEPES, pH 7.5. The activated enzyme was diluted to 2 nM into a 50-mL reaction mixture containing 100 mM HEPES, pH 7.5. 5 mM ATP, 10 mM $MgCl_2$, 2 mM peptide, 0.05 mg/mL BSA, and an inhibitor at varying concentrations and with or without 8 mCi/mL $[\gamma^{-33}P]$ATP dependent upon the method of analysis for the extent of reaction. The controls were reactions in the presence (negative controls) or absence (positive controls) of 50 mM EDTA. Reactions were allowed to proceed for 30 min at room temperature and quenched with addition of EDTA to 50 mM in 220 mL. The extent of reactions was analyzed in one of the two ways: an Elisa-based and a radioactive isotope-based. The quenched samples (200 mL) were transferred to a neutravidin coated plate (Perice) and incubated at room temperature for 40 min to allow biotinylated peptide to bind to neutravidin. The unbound peptide and the rest of the solution was washed away using a plate washer. In the Elisa format, a 200 mL HRP-PY20 anti phosphotyrosine antibody conjugate solution was added. After incubation for about 30 min, the plated was washed to remove unbound antibody-HRP conjugate. An Elisa substrate, K-blue (Neogen), was added and the Elisa reaction quenched with Red-stop (Neogen) after 15 min. The plate was read at $A_{625}$ in a plate reader. In the isotope-based format, the reactions had been performed in the presence of $[\gamma^{-33}P]$ATP. 200 mL Scintiverce DB was added to each well of the plate with bound biotin-peptide. The plate was sealed and counted in a micro-b-counter (Wallac). $IC_{50}$ values were obtained by fitting raw data to $A_{625}$ (cpm)=$V_{max}*(1-([1]/(IC_{50}+[1])))+b$, where b is background.

VEGFR-2

The peptide substrate used in the VEGFR-2 assay was biotin-aminohexyl-EEEEYFELVAKKKK-$NH_2$. The kinase domain of the enzyme was purified to homogeneity from a baculovirus expression system. The enzyme was preactivated on ice for 15 min in the presence of 100 µM ATP and 20 mM $MgCl_2$, and stored at −80° C. until needed for assay. The activated enzyme was diluted to 0.4 nM into a 60 µl reaction containing 100 mM HEPES, pH 7.5, 5 µM ATP, 10 mM $MgCl_2$, 5 µM peptide, 0.1 mM DTT, 0.05 mg/ml BSA, and an inhibitor at varying concentrations. The controls were reactions in the presence (negative controls) or absence (positive controls) of 50 mM EDTA. Reactions were incubated for 30 min at room temperature, and then quenched by the addition of EDTA to 60 mM in 210 µl. The quenched samples (190 µl) were transferred to a neutravidin-coated plate (Pierce) and incubated at room temperature for 40 min to allow biotinylated peptide to bind to the neutravidin. The unbound components of the reaction were removed by washing with a plate washer, then 200 µl HRP-PY20 anti-phosphotyrosine antibody conjugate was added to each well. After incubation for 40 min, the plate was washed to remove any unbound antibody. A HRP substrate, K-blue (Neogen) was added and the reaction was quenched with Red Stop (Neogen) after 20 min. The absorbance of the wells was read at $A_{650}$ in a plate reader. $IC_{50}$ values were obtained by fitting raw data to $A_{650}=V_{max}*(1-[1]/IC_{50}+[1])))+b$, where b is background.

The results shown in Table 2 summarise representative data: Table 2 illustrates the inhibitory activity of compounds of the present invention against several different kinases (CDK2, CDK1, cSrc, Lck, UL97, and VEGFR2).

TABLE 2

Kinase inhibition data of representative compounds

| Compound | CDK2 | CDK1 | cSrc | Lck | UL97 | VEGFR2 |
|---|---|---|---|---|---|---|
| Example 72 | +++ | ++ | + | + | +++ | ++ |
| Example 99 | ++ | + | + | + | ++++ | + |
| Example 68 | ++++ | ++ | | + | +++ | |
| Example 77 | ++++ | ++++ | | | ++++ | |
| Example 36 | ++++ | ++++ | + | + | +++ | + |
| Example 101 | +++ | ++ | | | | |
| Example 35 | ++++ | +++ | | | | |
| Example 27 | ++++ | +++ | | | | |
| Example 11 | ++++ | +++ | | | | |
| Example 103 | ++++ | +++ | | | | |
| Example 76 | +++ | + | + | + | | + |
| Example 104 | ++++ | +++ | | | | |

Key ($IC_{50}$, nM)
1–10: ++++
11–50: +++
51–100: ++
>100: +

As may be expected in light of the specific inhibitory activity of these compounds against several kinases involved in growth regulation, the compounds of this invention have antiproliferative properties which can be directly demonstrated in several cell proliferation assays. The results shown in Table 3 summarise some of these data for three different cell proliferation assays: MTT, FACS and G1-S progression. These assays are described below.

MTT Assay

Compounds are tested for their ability to inhibit cell proliferation and cell viability. The metabolic conversion of 3-(4,5-dimethylthiazol-2-yl)-2,5-diphenyltetrazolium bromide (MTT, Sigma #M2128) to a reduced form is a commonly used measure of cellular viability. Following is the procedure:

Cells are maintained in 75 cm$^2$ tissue culture flasks until ready for use. The cells are grown and plated for the assay in Dulbecco's modified Eagle's media (DMEM) containing 10% fetal bovine serum. For example, the following cell lines can be used: a) human foreskin fibroblasts (HFF); b) HT29 (human colon carcinoma cell line); c)MDA-MB-468 (human breast carcinoma cell line); d) RKO (human colon adenocarcinoma cell line); e) SW620 (human colon carcinoma cell line); f) A549 (human lung carcinoma cell line); and g) MIA PACA (human pancreatic carcinoma cell line). Cells are maintained at 37° C. in 10% $CO_2$, 90% humidified air. Cells are plated in 96-well tissue culture plates at the densities listed below. 100 μL of cell suspension is added to each well of the 96-well plate except the top row of the plate which contains no cells and serves as a reference for the spectrophotometer.

| cell line | density |
| --- | --- |
| HFF | 2500 cells/well |
| HT29 cell lines | 2500 cells/well |
| MDA-MB-468 cell line | 5000 cells/well |
| RKO cell line | 4000 cells/well |
| SW620 | 4000 cells/well |
| A549 | 5,500 cells/well |
| MIA PACA | 3000 cells/well |

Cells are incubated overnight in DMEM containing 10% fetal bovine serum at 37° C. in 10% $CO_2$, 90% humidified air prior to dosing. Cells are dosed in 10 sequential 3-fold dilutions starting at 30 μM depending upon the solubility of the compound. Compounds with solubilities of less than 30 μM are dosed at the highest soluble concentration. Stock solutions of compounds are made in 100% dimethyl sulfoxide (DMSO). Stock solutions are diluted in DMEM containing 100 μg/ml gentamicin and 0.3 to 0.6% DMSO at the twice the highest concentration to be placed on the cells. If compounds have been dissolved in DMSO the final concentration of DMSO on the cells is kept below 0.3%. Three-fold serial dilutions are performed on each compound to prepare 10 concentrations of the compound for dosing. 100 μl of diluted compound is added to the 100 μl of media currently on the dish. For each concentration of compound, 2–4 replicate wells are prepared.

Cells are returned to incubator and allowed to proliferate in the presence of compound for 72 h before addition of MTT. MTT is prepared in phosphate buffered saline (Irvine Scientific #9240) at a concentration of 2 mg/ml. 50 μl per well of MTT solution is added to the 200 μl of media to yield a final concentration of 0.4 mg/ml and plates are returned to the incubator for 4 h. After 4 h incubation the media, compound and MTT mixture is aspirated from the plates and 100 μl of 100% DMSO is added to each well in addition to 25 μl of Sorenson's Buffer (0.1M glycine, 0.1M NaCl, pH 10.5). Quantitation of metabolic reduction of MTT in each plate is performed by reading optical density at 570 nm wavelength on a Molecular Devices UVmax microplate reader. Growth inhibition curves and 50% inhibitory concentrations are determined using Microsoft Excel.

FACS Assay

The antiproliferative activity of the compounds of the present invention against a variety of normal or tumour cell lines can also be demonstrated by flow cytometry. These assays allow determination of both cell death and changes in cell cycle profile in cells following treatment of the compound. The assay is performed as follows:

1. Cells are incubated in DMEM to which 10% FCS has been added in a humidified incubator at 37° C. and 5% by volume of $CO_2$ in air. The cells are innoculated in 6-well plates at a density of 0.5–5×10$^5$ cells per well.
2. The test compound is added in serial dilutions 24–36 h after plating in 0.5% DMSO. The plates are then incubated a further 72 h in the presence of the compound. During this time, cells in control cultures undergo at least three cell divisions.
3. After incubation, the media is collected and cells are harvested by trypsinization. The cells and media are pooled and pelleted by centrifugation.
4. The cell pellet is fixed in a final volume of 3 mL of 50% ice cold MeOH and incubated for a minimum of 30 min at −20° C.
5. The cells are pelleted by centrifugation and resuspended in 0.5 mL PBS containing 1%FCS, 10 mg/mL Propidium Iodide (PI) and 5 mg/mL RNase A and incubated 30 min at 37° C. in the dark.
6. The samples are analysed by flow cytometry using the relative incorporation of PI as a measure of DNA content of each cell. The % Dead cells is recorded as % of events with less than 2N DNA. The $IC_{50}$ values for the compound are determined as the concentration of compound which results in 50% cell death relative to the control cultures. The compounds of the present invention give $IC_{50}$ values from 0.1 to >25 mmol/L. The compounds of the present invention additionally display $IC_{50}$ values for cell killing of 5- to 30-fold lower in several tumour cell lines, including the RKO and SW620 colon tumours, MDA MB468 breast tumour, H460 lung tumour and MES/.SA ovarian tumour cell lines, as compared to normal epithelial or fibroblast cell lines and therefore discriminate between normal cell lines and tumour derived cell lines for toxicity.

G1-S Progression Assay

This assay is designed to determine the ability of compounds to inhibit progression of cells from G1 into S-phase. CDK2 has been shown to be required for progression into S-phase in normal fibroblastic cells and therefore inhibition of this activity will prevent progression from G1-S. This assay therefore provides a rapid assessment of activity consistent with the inhibition of CDK2 in a cell-based format. The protocol is as follows:

(1) Grow human diploid fibroblasts (HDF-3) in 100 mm tissue culture dish to confluency. (2) Plate 6–7×10$^3$ cells/ well in a 96 well plate in 100 μl of DMEM. (3) After 16–17 h add various dilutions of test compounds (0.045–100 μM). Dilute compound in DMEM containing DMSO and add 100 µl to each well so that the DMSO conc. is 0.6–0.8% in 200 µl final volume. (4) Two h after addition of compound, add 20 ul of 100 µM BrdU (final conc. 10 µM) Make 100 µM solution in DMEM from 10 mM stock solution. (5) After 4 h, add 200 µl PBS to each well and remove the contents of the wells by inverting the plate and soaking on to the paper towel. Repeat the washing step three times, with 400 ul PBS each time. (6) Fix the cells and denature the DNA by adding 200 µl fixation/denaturation solution to each well for 30–40 min.

ranging from 0.05–10 µM. This inhibition of G1-S progression is consistent with these compounds acting as inhibitors of CDK2.

Results of these cell-based assays with representitive compounds are summarized in Table 3. HDF are normal diploid fibroblast cells. RKO are colon adenocarcinoma cells and MES/SA are ovarian carcinoma cells.

TABLE 3

Cell-based activities of representative compounds

| Compound | G1/S Chkpt | FACS | | | MTT | | |
|---|---|---|---|---|---|---|---|
| | | HDF | RKO | MES/SA | HDF | RKO | MDA MB468 |
| Example 72 | ++ | + | ++ | + | + | ++ | + |
| Example 99 | ++ | + | ++++ | + | +++ | ++++ | ++++ |
| Example 68 | ++ | + | ++ | | + | + | + |
| Example 77 | ++ | + | ++ | +++ | + | ++ | + |
| Example 36 | +++ | + | +++ | ++++ | ++ | +++ | +++ |
| Example 101 | + | + | + | | + | | ++ |
| Example 35 | + | + | ++ | + | + | ++ | + |
| Example 27 | ++ | + | ++ | | ++ | ++ | ++ |
| Example 11 | ++ | + | ++ | | | | |
| Example 103 | ++ | | | | ++ | ++ | ++ |
| Example 76 | ++ | + | ++ | ++ | + | + | + |
| Example 104 | ++ | | | | ++ | ++ | ++ |

Key (IC$_{50}$, µM)
0.1–0.5: ++++
0.6–1.0: +++
1.1–5.0: ++
>5.0: +

(7) Remove the fixation/denaturation solution by tapping the plate on the paper towel and add 75 ul of anti BrdU peroxidase antibody to each well. (dilute the antibody to 0.1 U/mL from 15 U/mL stock in PBS containing 1% BSA, Fraction V). Incubate the plate O/N at 4° C. (8) Remove the antibody solution and wash wells four times with 400 µl of PBS. Let the wash solution stay for 3–4 min during each wash. (9) Drain the wells and add 100 µl of chemiluminiscence Elisa reagent (Prepare the reagent 15–20 min before use to bring it to rt by mixing 100 parts of reagent A with 1 part of reagent B). (10) Read the plate in a luminometer. Take 2–3 readings within 6–7 min. Perform the following controls:

| Well contents | Blank | Background control |
|---|---|---|
| culture media | 200 µl | 100 µl |
| cells | — | 100 µl |
| BrdU | 20 µl | — |
| AntiBrdU-POD | 75 µl | 75 µl |

Reagents

Deoxybromouridine (BrdU), anti BrdU peroxidase antibodies, fixation/denaturation solution, chemiluminiscence reagent and BSA Fraction V, were obtained from Boehringer Mannheim. The 96-well white plate with clear bottom were purchased from Corning Costar Corporation. Dulbecco's Modified Eagle Medium containing high glucose, L-glutamine and pyridoxine HCl was obtained from GIBCO BRL.

The compounds of the present invention prevent progression of normal fibroblasts into S-phase with IC$_{50}$ values

UTILITY OF INVENTION

Inhibitors of members of the CDK family of kinases find utility as agents in the treatment of a wide variety of disorders which have a proliferative component or which involve regulation of cyclin dependent kinase function. These include cancers, restenosis, psoriasis, and actinic keratosis.

The tumour inhibitory activity of the compounds of the present invention can be demonstrated in vivo. The tumour inhibiting activity is determined using Swiss Nu/Nu female mice in which the human RKO colon adenocarcinoma has been implanted subcutaneously. In this assay, the compounds induce a marked reduction in the average tumour volume compared to vehicle treated controls.

The present invention demonstrates methodologies by which the onset of cell death in normal proliferating cells induced by chemotherapeutic drugs may be prevented by the prior treatment with inhibitors of cyclin dependent kinases. This may be useful to decrease the severity of chemotherapy-induced side effects due to killing of normal cells. These side effects may include, but are not limited to alopecia, mucocitis (nausea and vomiting, diahrea, oral lesions), neutropenia and thrombocytopenia. Inhibitors of cyclin dependent kinases CDK2 and CDK4 prevent the progression of normal cells into both S-phase (DNA synthesis) or M-phase (mitosis), reducing their susceptibility to incur damage by certain chemotherapeutic drugs which act in those phases of the cell cycle.

When the compounds of the present invention are used in conjunction with chemotherapeutic agents, they reduce the severity of chemotherapy-induced side effects. The protective effects of these compounds can be demonstrated in tissue culture using normal diploid fibroblasts. Cells are plated 36 h prior to the administration of the compounds of the present invention, which are dosed at or above the $IC_{50}$ concentrations determined by the G1 checkpoint assay. Cells are then treated with cytotoxic compounds anywhere from 0 to 24 h after treatment with the compounds of the present invention. Cells are incubated with the combination of the cytotoxic and the compound of the present invention from 3 to 72 h. Cytotoxic drugs include, but are not limited to taxanes, vinca alkyloids, anthracyclins, etoposide, mitoxantrone, topoisomerase I inhibitors, and Ara C. Cell death may be recorded by morphological observation, or by assessment by MTT or FACS analysis The compounds of the present invention reduce the amount of cell death when used in combination with cytotoxics, as compared to the cytotoxic alone.

The chemoprotective activity of these agents has additionally been demonstrated in vivo. Protection from chemotherapy-induced alopecia is determined in 7 day old Sprague-Dawley rat pups. The treatment is carried out by administering the compounds topically to the head of the animal in doses from 0.01 to 10 mg/kg 2 h before and 2 h after the administration of a single dose of 6 mg/kg etoposide intraperitoneally. Six days after dosing, animals are scored visually for hair loss using a grading scale from 1 (complete hair loss) to 4 (no apparent hair loss). In this assay, the prior treatment of the animal with the compound of this invention results in a marked reduction in the severity of alopecia compared to vehicle treated controls. Under the above described conditions of treatment, the compounds of the present invention also protect against other toxicities of etoposide. Animals treated with etoposide alone show a dramatic lack of weight gain compared to untreated animals. Animals treated with the compounds of the present invention in combination with etoposide, in the schedule indicated above, gain weight normally and even exceed the body weight of control, untreated animals.

The compounds of the present invention additionally show an additive or synergistic effect on cell kill when dosed in combination with cytotoxic drugs in tumour cells (but not normal cells). This can be demonstrated by pretreating normal fibroblasts or RKO colon carcinoma cells with the compounds of the present invention (at concentrations that equals the IC50 in the G1 checkpoint assay) for 4 h prior to the administration of cytotoxic drug. Cytotoxic drugs include, but are not limited to taxanes, vinca alkyloids, anthracyclins, etoposide, mitoxantrone, topoisomerase I inhibitors, and Ara C. This synergistic effect may also be shown in vivo. Neonatal Sprague-Dawley rats bearing WARD syngeneic tumours are dosed with a combination of etoposide with the compound of the present invention as described above for the protection experiments. Animals dosed in such a manner show an increased antitumour effect as compared to animals dosed with etoposide alone. The compounds of the present invention may therefore be administered systemically to animals in combination with cell-cycle specific cytotoxic drugs to both increase the antitumour effect of the cytotoxic as well as reduce the severity of side effects of the cytotoxic drug. This will allow the dose of cytotoxic to be escalated to further improve antitumor activity without increasing the host toxicity of the cytotoxic.

The compounds of the present invention may also be used in combination with radiation treatment to show similar protection of normal cells from the effects of radiation and may be used as radiosensitizers to increase the tumour killing by radiation therapy.

The compounds of the present invention which are inhibitory for CDK4 or CDK6 activity will selectively inhibit cell cycle progression in cells which retain a functional retinoblastoma protein. Thus, it will be expected that inhibition of CDK4 will systemically protect normal dividing cells, including the GI and oral mucosa, hematopoietic cells and cells in the hair follicle, but be unable to protect tumour cells with loss of RB function, either by deletion or mutation. This implies that compounds which inhibit CDK4 will be useful as systemically administered cytoprotectant drugs in patients with tumours which have lost Rb, with no protective effect on the tumour itself. Such compounds could be expected to allow for increased dosing frequency and dose escalation of the cytotoxic regimens in these patients, improving the outcome of the patient.

The compounds from the present invention will also have utility in the treatment of viral infections. The antiviral activity of these compounds can be demonstrated in cytomegalovirus (CMV) and human papillomavirus (HPV) replication assays. The $IC_{50}$ for inhibition of CMV replication ranges from 0.05 to 5 μM.

The assay for CMV replication is performed as follows:
1. Growth of human fibroblast cells:

MRC-5 human lung fibroblasts (passage #27–30) were were cultured in minimal essential medium with added 8% v/v fetal calf serum, 2 mM L-glutamine, 100 units/mL penicillin G, and 100 μg/mL streptomycin sulfate, (MEM 8-1-1). Incubation was at 37° C. in air plus 5% $CO_2$. Cells were inoculated into 96-well plates at ~7×$10^3$ cells/well and incubated a further 3 days to confluence (~2×$10^4$ cells/well).
2. Infection of cells:

Medium is removed from peach well down to 20 μl and 150 pfu of HCMV (Strain AD169) suspended in 25 μl of medium MEM 2-1-1 (same as MEM 8-1-1 above, but with 2% v/v fetal calf serum) is added. (MOI ~0.013). Plates are centrifuged at 1500 rpm for 10 min at 25° C. and incubated 90 min at 37° C. 180 μl of medium MEM 2-1-1 containing compounds is added to give a range of final concentrations from 0.01 to 100 mM. Multiple plates are set up for each combination with one mock-infected plate for estimation of cytotoxicity. Plates are then incubated at 37° C. in air plus 5% $CO_2$ for six days (two rounds of viral replication). Cytotoxicity is estimated microscopically on the mock-infected plates, and the infected plates were harvested by decanting the medium from the wells.
3. Preparation, blotting and quantitative hybridization of DNA:

Cells are lysed by adding 50 μl of 0.1 M Tris Cl (pH 8), 50 mM EDTA, 0.2% SDS, and 0.1 mg/mL proteinase K to each well and incubating 1 h at 55° C. The lysates were diluted with 150 μl of water and extracted by mixing with 65 μl phenol saturated with 0.01 M Tris Cl (pH 8) and 1 mM EDTA. The plates were centrifuged at 2200 rpm for 15 min. Next, 50 μl of the aqueous layer was transfered to a new 96-well plate and mixed with 50 μl of 0.5 N NaOH. After incubation at 95° C. for 15 min, the samples were made to 1.5 M Ammonium acetate, 0.15 M Ammonium $H_2$ phosphate, 5 mM EDTA, pH 6.5 (APE buffer), and blotted onto BRL Supported Nitrocellulose (cat # 1465MH) membranes under vacuum Each well was washed with 200 μl APE buffer. The samples were crosslinked to the membrane with UV light.
4. Quantitative DNA-DNA hybridization:

The hybridization probe was prepared from cosmids pC7S31 & pCS37 (Sullivan, et al., Antimicrobial Agents & Chemotherapy 1993, 37, 19–25). These contain the HCMV AD169 sequences from nucleotides 102,000 to 143,300 and 51,600 to 92,900, respectively. The probe is a 1:1 mixture of the two cosmids labeled with α-[$^{32}$P]-dCTP Prehybridization of the membranes is carried out in 6×SSPE, 1% Ficoll, 1% polyvinylpyrrolidine, 1% BSA, 0.5% SDS, and 50 μg /mL salmon sperm DNA at 45° C. for 2 to 12 h. The prehybdridization solution was replaced with hybridization solution (6×SSPE, 0.5% SDS, 50 μg/mL salmon sperm DNA) containing 1×10⁶ cpm/mL of each heat-denatured probe. Hybridization was for 16 h at 65° C. The membranes were then washed as follows: 6×SSPE with 0.5% SDS, room temperature, 2× for 2 min; 1×SSPE with 0.5% SDS, 65° C., 2× for 15 min; 0.1×SSPE with 0.5% SDS, 65° C., once for 1 h. The membranes were blotted dry and wrapped in Saran wrap for quantitation by PhosphorImager. The counts of the drug dilution wells were compared to the counts of untreated control wells to produce a response curve and were used to calculate the $IC_{50}$ values. These $IC_{50}$ values were calculated by weighted linear regression according to the Hill equation.

The compounds of the present invention may also be used for the treament of other conditions mentioned in connection with modulators of CDK activity. In particular for the treatment of diseases that respond to inhibition of CDK activity, including protection of cells from infection by other viruses and treatment of Alzheimers. Furthermore, these compounds will have utility in the specific inhibition of non-human CDK activities, such as the *Aspergillus fumigatus* cdc2 homologue and will therefore be useful in the treatment of fungal or other eukaryotic infections.

The compounds of the present invention also inhibit other kinases. In particular, these compounds show affinity for the Src tyrosine kinase. The Src tyrosine kinase participates in a variety of fundamental processes within the cell, including signal transduction from cell-surface receptors, apoptosis and cell division. Compounds which are able to inhibit the src TK find utility as tumour inhibitory and antiinflammatory agents. These compounds are also useful for the prevention of osteoporosis and bone building by inhibition of src in osteoclasts (Tanaka, et al., Nature 1996, 383, 528–31). In addition, the compounds of this invention are suitable for other utilities mentioned in connection with Src modulators, and they can be used in particular for the treatment of diseases that respond to the inhibition of the Src tyrosine kinase.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for cancer conditions, or for other indications for the compounds of the invention as indicated above. Likewise, the specific pharmacologic responses observed may vary according to and depending upon the particular active compound selected or whether there are present certain pharmaceutical carriers, as well as the type of formulation and mode of administration employed, and such expected variations or differences in the results are contemplated in accordance with the objects and practices of the present invenion. It is intended, therefore, that the invention be limited only by the scope of the claims which follow and that such claims be interpreted as broadly as is reasonable.

We claim:
1. A compound of formula (I):

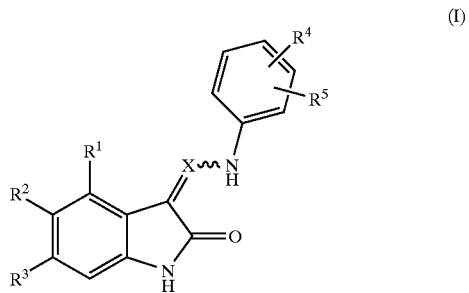

wherein
X is N, CH or CCH₃;
R¹ is hydrogen, nitro, carboxamide, isopropyl, hydroxymethyl, pyridin-4-ylethyl, ethoxycarbonyl, iodo, isobutyl, 2-methyl-propenyl, 2-methyl-1-butenyl, 2-methyl-2-butenyl, 2-methylbutyl, cyclobutyl-methyl, cyclobutylidenemethyl, 4-hydroxyphenyl-ethyl, 4-hydroxyphenyl-vinyl, phenoxy, isopropoxy, pyrazol-3-yl, methyl or chloro;
R² is hydrogen, oxazol-5-yl, pentafluorophenoxycarbonyl, nitro, hydroxy, methoxy, methyl, triazol-1-yl, sulfonate, carboxamide, methoxycarbonyl, bromo, iodo, aminosulfonyl, methylsulfonyl, methylaminosulfonyl, methyloxime, phenyl, N,N-dimethylaminocarbonyl, N-furan-2-ylmethylaminocarbonyl, N-(N-morpholino) ethylaminocarbonyl, N-(1,5-dimethoxybenzyl) aminocarbonyl, N-(imidazol-1-yl)ethylaminocarbonyl, N-(imidazol-1-yl)propylaminocarbonyl, N-(methoxyethyl)aminocarbonyl, N-(hydroxyethyl) aminocarbonyl, N-(hydroxypropyl)aminocarbonyl, N-(3-hydroxy-2,2-dimethylpropyl)aminocarbonyl, N-(pyrid-3-ylmethyl)aminocarbonyl, quaternary ammonium, methylcarbonylamino or isobutoxycarbonyl;
R³ is hydrogen, bromo, chloro, methyl, ethyl, isopropyl, hydroxy, hydroxymethyl, phenoxy, or ethoxy;
R⁴ is in the para-position of the phenyl ring relative to the NH group, and is selected from aminosulfonyl, N-methylaminosulfonyl, methylsulfonyl, N,N-dimethylaminosulfonyl, aminosulfonylamino, N-hydroxyethoxyethylaminosulfonyl, N-hydroxyethylaminosulfonyl, N-(3-hydroxy-2,2-dimethyl-propyl)aminosulfonyl-methyl, N-methylaminosulfonyl-methyl, indazol-6-ylaminosulfonyl, thiazol-2-ylaminosulfonyl, N-aminoiminomethyl-aminosulfonyl, N-pyrid-2-ylaminosulfonyl, aminosulfonyl-methyl, N-allylaminosulfonyl-methyl, methylsulfonylmethyl, N-(3-hydroxy-2,2-dimethyl-propyl)aminosulfonyl, N-(3-trifluoromethylphenyl)aminosulfonyl, N-pyrimidin-2-ylaminosulfonyl, N-(5-methyl-thiadiazol-2-yl)aminosulfonyl, N-methylcarbonylaminosulfonyl, N-phenylcarbonylaminosulfonyl, N-hydroxyethoxyethyl-N-methylaminosulfonyl, N-methoxyethoxyethoxyethyl-aminosulfonyl and N-(pyridin-4-yl-methyl)aminosulfonyl;
R⁵ is hydrogen;
with the proviso that R¹, R² and R³ cannot simultaneously each represent hydrogen;

and the pharmaceutically acceptable salts, biohydrolyzable esters, biohydrolyzable amides, biohydrolyzable carbamates, solvates, hydrates, affinity reagents or prodrugs thereof in either crystalline or amorphous form.

2. A compound as claimed in claim 1 selected from the group consisting of:

4-[N'-(4-Nitro-2-oxo-1,2-dihydro-indol-3-ylidene)-hydrazino]-benzenesulfonamide;
4-[N'-(4-Isopropyl-2-oxo-1,2-dihydro-indol-3-ylidene)-hydrazino]-benzenesulfonamide;
4-[(4-Hydroxymethyl-2-oxo-1,2-dihydro-indol-3-ylidenemethyl)-amino]-N-methyl-benzenesulfonamide;
4-{N'-[2-Oxo-4-(2-pyridin-4-yl-ethyl)-1,2-dihydro-indol-3-ylidene]-hydrazino}-benzenesulfonamide;
2-Oxo-3-(4-sulfamoyl-phenylamino-methylene)-2,3-dihydro-1H-indole-4-carboxylic acid ethyl ester;
4-[N'-(4-Iodo-2-oxo-1,2-dihydro-indol-3-ylidene)-hydrazino]-benzenesulfonamide;
4-[N'-(4-Isobutyl-2-oxo-1,2-dihydro-indol-3-ylidene)-hydrazino]-benzenesulfonamide;
4-{N'-[4-(2-Methyl-propenyl)-2-oxo-1,2-dihydro-indol-3-ylidene]-hydrazino}-benzenesulfonamide;
4-{N'-[4-(2-Methyl-1-butenyl)-2-oxo-1,2-dihydro-indol-3-ylidene]-hydrazino}-benzenesulfonamide;
4-{N'-[4-(2-Methyl-2-butenyl)-2-oxo-1,2-dihydro-indol-3-ylidene]-hydrazino}-benzenesulfonamide;
4-{N'-[4-(2-methylbutyl)-2-oxo-1,2-dihydro-indol-3-ylidene]-hydrazino}-benzenesulfonamide;
4-[N'-(4-Cyclobutylmethyl-2-oxo-1,2-dihydro-indol-3-ylidene)-hydrazino]-benzenesulfonamide;
4-[N'-(4-Cyclobutylidenemethyl-2-oxo-1,2-dihydro-indol-3-ylidene)-hydrazino]-benzenesulfonamide;
4-(N'-{4-[2-(4-Hydroxyphenyl)-ethyl]-2-oxo-1,2-dihydro-indol-3-ylidene}-hydrazino)-benznensulfonamide;
4-(N'-{4-[2-(4-Hydroxyphenyl)-vinyl]-2-oxo-1,2-dihydro-indol-3-ylidene}-hydrazino)-benznensulfonamide;
4-[N'-(2-Oxo-4-phenoxy-1,2-dihydro-indol-3-ylidene)-hydrazino]-benzenesulfonamide;
4-[N'-(4-Isopropoxy-2-oxo-1,2-dihydro-indol-3-ylidene)-hydrazino]-benzenesulfonamide;
4-{N'-[2-Oxo-4-(1H-pyrazol-3-yl)-1,2-dihydro-indol-3-ylidene]-hydrazino}-benzenesulfonamide;
4-[(5-Oxazol-5-yl-2-oxo-1,2-dihydro-indol-3-ylidenemethyl)-amino]benzenesulfonamide;
2-Oxo-3-[(4-sulfamoyl-phenyl)-hydrazone]-2,3-dihydro-1H-indole-5-carboxylic acid 2,3,4,5,6-pentafluorophenyl ester;
4-[N'-(5-Nitro-2-oxo-1,2-dihydro-indol-3-ylidene)-hydrazino]-benzenesulfonamide;
4-[N'-(5-Hydroxy-2-oxo-1,2-dihydro-indol-3-ylidene)-hydrazino]-benzenesulfonamide;
4-[N'-(5-Methyl-2-oxo-1,2-dihydro-indol-3-ylidene)-hydrazino]-benzenesulfonamide;
N-Methyl-4-[N'-(2-oxo-5-[1,2,4]triazol-1-yl-1,2-dihydro-indol-3-ylidene)-hydrazino]-benzenesulfonamide;
2-Oxo-3-[(4-sulfamoyl-phenyl)-hydrazono]-2,3-dihydro-1H-indole-5-sulfonic acid sodium salt;
3-[(4-Methylsulfamoyl-phenyl)-hydrazono]-2-oxo-2,3-dihydro-1H-indole-5-carboxylic acid amide;
2-Oxo-3-(4-sulfamoyl-phenylamino-methylene)-2,3-dihydro-1H-indole-5-carboxylic acid methyl ester;
5-Bromo-3-[(4-Methylsulfonyl-phenyl)-hydrazono]-1,3-dihydro-indol-2-one;
2-Oxo-3-[(4-sulfamoyl-phenyl)-hydrazono]-2,3-dihydro-1H-indole-5-sulfonic acid amide;
4-[N'-(5-Methylsulfonyl-2-oxo-1,2-dihydro-indol-3-ylidene)-hydrazino]-benzenesulfonamide;
3-[(4-Methylsulfamoyl-phenyl)-hydrazono]-2-oxo-2,3-dihydro-1H-indole-5-sulfonic acid methylamide;
4-{N'-[5-(1-Hydroxyimino-ethyl)-2-oxo-1,2-dihydro-indol-3-ylidene]-hydrazino}-N-methyl-benzenesulfonamide;
4-[1-(5-Oxazol-5-yl-2-oxo-1,2-dihydro-indol-3-ylidene)-ethylamino]-benzenesulfonamide;
N,N-Dimethyl-4-[(5-oxazol-5-yl-2-oxo-1,2-dihydro-indol-3-ylidenemethyl)-amino]-benzenesulfonamide;
4-[1-(5-Oxazol-5-yl-2-oxo-1,2-dihydro-indol-3-ylidene)-hydrazino]-benzenesulfonamide;
4-[(2-Oxo-5-phenyl-1,2-dihydro-indol-3-ylidenemethyl)-amino]-benzenesulfonamide;
2-Oxo-3[(4-sulfamoyl-phenyl)-hydrazono]-2,3-dihydro-1H-indole-5-carboxylic acid dimethylamide;
2-Oxo-3-[(4-sulfamoyl-phenyl)-hydrazono]-2,3-dihydro-1H-indol-5-carboxylic acid(furan-2-ylmethyl)-amide;
2-Oxo-3-[(4-sulfamoyl-phenyl)-hydrazono]-2,3-dihydro-1H-indol-5-carboxylic acid-2,6-dimethoxy-benzylamide;
2-Oxo-3[(4-sulfamoyl-phenyl)-hydrazono]-2,3-dihydro-1H-indole-5-carboxylic acid(2-morpholin-4-yl-ethyl)-amide;
2-Oxo-3-[(4-sulfamoyl-phenyl)-hydrazono]-2,3-dihydro-1H-indole-5-carboxylic acid(2-imidazol-1-yl-ethyl)-amide;
2-Oxo-3-[(4-sulfamoyl-phenyl)-hydrazono]-2,3-dihydro-1H-indole-5-carboxylic acid(3-imidazol-1-yl-propyl)-amide;
2-Oxo-3-[(4-sulfamoyl-phenyl)-hydrazono]-2,3-dihydro-1H-indole-5-carboxylic acid(2-methoxyethyl)-amide;
2-Oxo-3-[(4-sulfamoyl-phenyl)-hydrazono]-2,3-dihydro-1H-indole-5-carboxylic acid(2-hydroxyethyl)-amide;
2-Oxo-3-[(4-sulfamoyl-phenyl)-hydrazono]-2,3-dihydro-1H-indole-5-carboxylic acid(3-hydroxypropyl)-amide;
2-Oxo-3-[(4-sulfamoyl-phenyl)-hydrazono]-2,3-dihydro-1H-indole-5-carboxylic acid(3-hydroxy-2,2-dimethylpropyl)-amide;
2-Oxo-3-[(4-sulfamoyl-phenyl)-hydrazono]-2,3-dihydro-1H-indole-5-carboxylic acid(pyridin-3-ylmethyl)-amide;
2-Oxo-3-[(4-sulfamoyl-phenyl)-hydrazono]-2,3-dihydro-1H-indole-5-carboxylic acid(pyridin-4-ylmethyl)-amide;
4-[N'-(5-Methoxy-2-oxo-1,2-dihydro-indol-3-ylidene)-hydrazino]-benzenesulfonamide;
4-[N'-(5-Amino-2-oxo-1,2-dihydro-indol-3-ylidene)-hydrazino]-benzenesulfonamide hydrochloride;
4-[N'-(6-Ethyl-2-oxo-1,2-dihydro-indol-3-ylidene)-hydrazino]-benzenesulfonamide;
N-{4-[(2-Oxo-1,2-dihydro-indol-3-ylidenemethyl)-amino]-phenyl}sulfamide;
4-[(6-Hydroxymethyl-2-oxo-1,2-dihydro-indol-3-ylidenemethyl)-amino]-benzenesulfonamide;
4-[N'-(6-Bromo-2-oxo-1,2-dihydro-indol-3-ylidene)-hydrazino]-benzenesulfonamide;
4-[N'-(2-Oxo-6-phenoxy-1,2-dihydro-indol-3-ylidene)-hydrazino]-benzenesulfonamide;
4-[N'-(6-Ethoxy-2-oxo-1,2-dihydro-indol-3-ylidene)-hydrazino]-benzenesulfonamide;
N-Methyl-4-[N'-(4-methyl-5-nitro-2-oxo-1,2-dihydro-indol-3-ylidene)-hydrazino]-benzenesulfonamide;
4-[N'-(5,6-Dimethyl-2-oxo-1,2-dihydro-indol-3-ylidene)-hydrazino]-benzenesulfonamide;
N-{6-Hydroxy-3-[(4-methylsulfamoylmethyl-phenyl)-hydrazono]-2-oxo-2,3-dihydro-1H-indol-5-yl}-acetamide;
4-[N'-(6-Chloro-5-methoxy-2-oxo-1,2-dihydro-indol-3-ylidene)-hydrazino]benzene-sulfonamide;
4-[N'-(5-Hydroxy-6-isopropyl-2-oxo-1,2-dihydro-indol-3-ylidene)-hydrazino]-benzenesulfonamide;

C-{4-[N'-(4,6-Dichloro-5-methoxy-2-oxo-1,2-dihydro-indol-3-ylidene)-hydrazino]-phenyl}-N-methyl-methanesulfonamide;

4-[N'-(4-Chloro-5-hydroxy-6-methyl-2-oxo-1,2-dihydro-indol-3-ylidene)-hydrazino]-benzenesulfonamide;

4-[N'-(5-Hydroxy-4,6-dimethyl-2-oxo-1,2-dihydro-indol-3-ylidene)-hydrazino]-benzenesulfonamide;

4-[N'-(5-Hydroxy-4,6-dimethyl-2-oxo-1,2-dihydro-indol-3-ylidene)-hydrazino]-phenyl}-N-methyl-methanesulfonamide;

2-Oxo-3-(4-sulfamoyl-phenylamino-methylene)-2,3-dihydro-1H-indole-5-carboxylic acid isobutyl ester;

and the pharmaceutically acceptable salts, biohydrolyzable esters, biohydrolyzable amides, biohydrolyzable carbamates, solvates, hydrates, affinity reagents or prodrugs thereof in either crystalline or amorphous form.

3. A compound as claimed in claim 1, selected from the group consisting of:

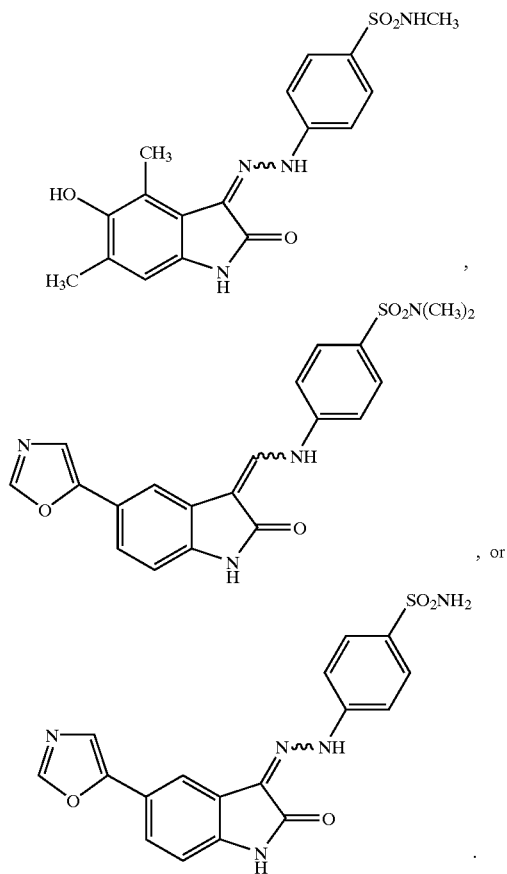

4. A compound as claimed in claim 1, wherein said compound is in the E geometric isomer form.

5. A compound as claimed in claim 1, wherein said compound is in the Z geometric isomer form.

6. A compound as claimed in claim 1, wherein said compound is a mixture of the Z geometric isomer form and the E geometric isomer form.

7. A compound as claimed in claim 1, having at least one chiral center and which compound is dextrorotatory.

8. A compound as claimed in claim 1, having at least one chiral center and which compound is levorotatory.

9. A compound as claimed in claim 1, having at least one chiral center and which compound is a mixture of dextrorotatory and levorotatory forms.

10. A pharmaceutical composition comprising a pharmaceutically acceptable carrier and a pharmacologically effective amount of a compound as claimed in claim 1.

11. A topical pharmaceutical composition comprising a pharmaceutically acceptable carrier and a pharmacologically effective amount of a compound as claimed in claim 1.

12. A method of treating a disease mediated by a cyclin dependent kinase, said method comprising the step of administering to a mammal in need thereof a pharmacologically effective amount of a compound as claimed in claim 1.

13. A method of treating a disease mediated by CDK2, said method comprising the step of administering to a mammal in need thereof a pharmacologically effective amount of a compound as claimed in claim 1.

14. A method of treating a disease mediated by CDK4, said method comprising the step of administering to a mammal in need thereof a pharmacologically effective amount of a compound as claimed in claim 1.

15. A method of inhibiting tumor growth, comprising the step of administering to a mammal in need thereof a pharmacologically effective amount of a compound as claimed in claim 1.

16. A method of treating chemotherapy-induced alopecia, comprising the step of administering to a patient in need thereof a pharmacologically effective amount of a compound as claimed in claim 1.

17. A method as claimed in claim 16, in which said compound is administered in a topical pharmaceutical preparation.

* * * * *